US009624223B2

(12) United States Patent
Nagase et al.

(10) Patent No.: US 9,624,223 B2
(45) Date of Patent: Apr. 18, 2017

(54) MORPHINAN DERIVATIVE

(71) Applicants: THE KITASATO INSTITUTE, Tokyo (JP); NIPPON CHEMIPHAR CO., LTD., Tokyo (JP)

(72) Inventors: Hiroshi Nagase, Ibaraki (JP); Hideaki Fujii, Kanagawa (JP); Eriko Nakata, Saitama (JP); Yoshikazu Watanabe, Tokyo (JP); Daisuke Saito, Tokyo (JP); Toshihiro Takahashi, Saitama (JP)

(73) Assignees: THE KITASATO INSTITUTE, Tokyo (JP); NIPPON CHEMIPHAR CO., LTD., Tokyo (JP)

( * ) Notice: Subject to any disclaimer, the term of this patent is extended or adjusted under 35 U.S.C. 154(b) by 0 days.

(21) Appl. No.: 14/772,188

(22) PCT Filed: Oct. 15, 2013

(86) PCT No.: PCT/JP2013/077886
§ 371 (c)(1),
(2) Date: Dec. 15, 2015

(87) PCT Pub. No.: WO2014/136305
PCT Pub. Date: Sep. 12, 2014

(65) Prior Publication Data
US 2016/0122349 A1 May 5, 2016

(30) Foreign Application Priority Data

Mar. 8, 2013 (JP) ................................. 2013-047325

(51) Int. Cl.
*C07D 471/08* (2006.01)
*C07D 491/20* (2006.01)
*C07D 471/10* (2006.01)

(52) U.S. Cl.
CPC ......... *C07D 471/08* (2013.01); *C07D 471/10* (2013.01); *C07D 491/20* (2013.01)

(58) Field of Classification Search
CPC .. C07D 471/08; C07D 471/10; C07D 491/20; A61K 31/04
See application file for complete search history.

(56) References Cited

U.S. PATENT DOCUMENTS

| 5,981,540 | A | 11/1999 | Dondio et al. |
| 6,136,817 | A | 10/2000 | Schmidhammer |
| 6,365,594 | B1 | 4/2002 | Dondio et al. |
| 8,637,539 | B2 | 1/2014 | Nagase et al. |
| 8,950,203 | B2* | 2/2015 | Giertz ................... F25B 13/00 62/160 |
| 8,952,030 | B2 | 2/2015 | Nagase et al. |
| 2006/0094741 | A1 | 5/2006 | Nagase et al. |

FOREIGN PATENT DOCUMENTS

| WO | 95/31463 A1 | 11/1995 |
| WO | 96/02545 A1 | 2/1996 |
| WO | 97/25331 A1 | 7/1997 |
| WO | 01/14382 A1 | 3/2001 |
| WO | 01/14383 A1 | 3/2001 |
| WO | 2008/001859 A1 | 1/2008 |
| WO | 2012/102360 A1 | 8/2012 |

(Continued)

OTHER PUBLICATIONS

T. J. Hudzik et al., "Preclinical Pharmacology of AZD2327: A Highly Selective Agonist of the δ-Opioid Receptor", Journal of Pharmacology and Experimental Therapeutics, vol. 138, pp. 195-204, 2011.

Pierre-Eric Lutz et al., "Opioid receptors: distinct roles in mood disorders", Trends in Neurosciences, 2013, vol. 36, No. 3, pp. 195-206.

Akiyoshi Saitoh et al., "The novel δ opioid receptor agonist KNT-127 produces antidepressant-like and antinociceptive affects in mice without producing convulsions", Behavioural Brain Research, 2011, vol. 223, pp. 271-279.

(Continued)

*Primary Examiner* — D M Seaman
(74) *Attorney, Agent, or Firm* — Greenblum & Bernstein, P.L.C.

(57) ABSTRACT

The present invention relates to a morphinan derivative represented by the following general formula (I), wherein $R^1$ represents hydrogen, $C_{1-6}$ alkyl, $C_{6-10}$ aryl, etc., $R^2$ and $R^3$, which are the same or different, represent hydrogen, hydroxy, etc., $R^4$ and $R^5$ represent hydrogen, $C_{1-6}$ alkyl, etc., $R^6$ represents hydrogen, hydroxy, $C_{1-6}$ alkyl, etc., X represents O or $CH_2$, Y represents C=O, C(=O)O, etc., and m and n, which are the same or different, represent an integer of 0 to 2 (m and n are not 0 at the same time), a tautomer or stereoisomer of the compound, or a pharmaceutically acceptable salt thereof, or a solvate thereof, as well as an analgesic, antianxiety drug, etc. containing the same as an active ingredient.

22 Claims, No Drawings

(56) References Cited

FOREIGN PATENT DOCUMENTS

WO    2013/035833 A1    3/2013

OTHER PUBLICATIONS

Akiyoshi Saitoh et al., "The novel δ opioid receptor agonist KNT-127 produces distinct anxiolytic-like effects in rats without producing the adverse effects associated with benzodiazepines", Neuropharmacology, 2013, vol. 67, pp. 485-493.

Akiyoshi Saitoh et al., "Antidepressant-like Effects of δ Opioid Receptor Agonists in Animal Models", Current Neuropharmacology, 2012, vol. 10, pp. 231-238.

Kohei Hayashida et al., "Rearrangement of 4,5α-epoxymorphinan derivatives with carbamoylepoxy rings provide novel oxazatricyclodecane structures", Tetrahedron, 2011, vol. 67, pp. 6682-6688.

International Search Report and Written Opinion issued with respect to application No. PCT/JP2013/077886, dated Nov. 12, 2013.

International Preliminary Report on Patentability issued with respect to application No. PCT/JP2013/077886, dated Sep. 8, 2015.

European Search Report issued with respect to application No. 13877360.1, mail date is Aug. 11, 2016.

\* cited by examiner

MORPHINAN DERIVATIVE

TECHNICAL FIELD

The present invention relates to a morphinan derivative having an opioid δ receptor agonistic activity.

BACKGROUND ART

Three types of opioid receptors, i.e., μ, δ, and κ receptors, are known, and morphine showing potent affinity to the μ receptor has been used as an analgesic for a long time. Although morphine has potent analgesic effect, it is known that morphine causes adverse events such as formation of dependence, respiratory depression, and constipation via the μ receptor.

It is further known that, although the δ receptor also has an analgesic action, δ receptor agonists are not involved in the adverse events observed for morphine.

Therefore, it is considered that a δ receptor-selective agonist may have a potential as an analgesic superior to morphine, and for this reason, researches concerning creation of such an analgesic have been actively conducted. It is also reported that a δ receptor agonist may serve as an antianxiety drug or antidepressant (Non-patent documents 1, 2, 3, 4, and 5).

However, any δ receptor agonist has not been approved yet as a therapeutic or prophylactic agent.

Patent document 1 describes that the compound represented by the following formula (A):

[Formula 1]

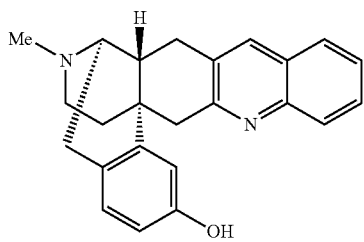

has an opioid δ receptor agonistic activity.

Further, in Non-patent document 6, the inventors of the present invention made reports concerning the compound represented by the following formula (B).

[Formula 2]

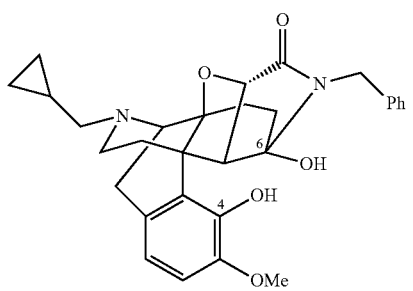

However, this compound has higher affinity to the μ receptor than the δ receptor.

The inventors of the present invention recently also found that the compound represented by the following formula (C):

[Formula 3]

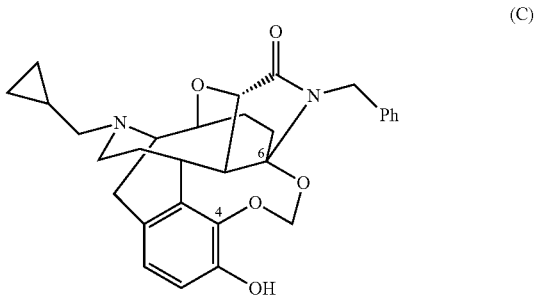

in which the morphinan structure is cyclized at the 4- and 6-positions via a methylenedioxy structure, has a δ agonist activity, and filed a patent application therefor (Patent document 2).

BACKGROUND ART REFERENCES

Patent Documents

Patent document 1: WO2008/001859
Patent document 2: WO2012/102360

Non-Patent Documents

Non-patent document 1: J. Pharmacol. Exp. Ther., 2011, 338, 195
Non-patent document 2: Trends in Neurosciences, 2013, 36, 195
Non-patent document 3: Behavioural Brain Research, 2011, 223, 271
Non-patent document 4: Neuropharmacology, 2013, 67, 485
Non-patent document 5: Current Neuropharmacology, 2012, 10, 231
Non-patent document 6: Tetrahedron, 2011, 67, 6682

SUMMARY OF THE INVENTION

Object to be Achieved by the Invention

It is desired to provide a compound that shows superior opioid δ agonistic activity and opioid δ selectivity, and reduced adverse drug reaction.

Means for Achieving the Object

To achieve the aforementioned object, the inventors of the present invention conducted various researches on a morphinan derivative represented by the general formula (I) mentioned below, a tautomer or stereoisomer of the compound, or a pharmaceutically acceptable salt thereof, or a solvate thereof, as well as on an analgesic, antianxiety drug, and antidepressant comprising said substance as an active ingredient.

The inventors of the present invention presented the following compound (D) in Non-patent document 7 (38th Symposium for Progress of Reaction and Synthesis, Nov. 5 and 6, 2012 (presented on November 6 in Tokyo)) and Non-patent document 8 (30th Medicinal Chemistry Symposium, Nov. 28 to 30, 2012 (presented on November 28 in Tokyo)).

[Formula 4]

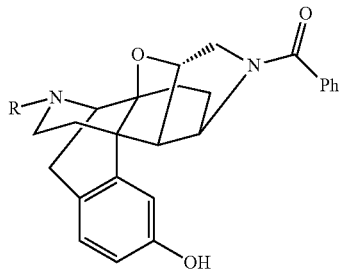

(D)

(wherein R is methyl, isobutyl, allyl, or cyclopropylmethyl.) The aforementioned compound (D) is definitely structurally different from the compounds of the present invention represented by the general formula (I) mentioned below. Specifically, while the R moiety of the aforementioned compound (D) is limited to an unsubstituted alkyl group, an unsubstituted cycloalkylalkyl group, or an unsubstituted alkenyl group, the moiety corresponding to R in the compounds of the present invention represented by general formula (I) mentioned below is selected from various aminoalkyl groups including cyclic amino groups. In addition, X of the compounds of the present invention represented by the general formula (I) mentioned below is an oxygen atom or $CH_2$, whereas, in the compound represented by the aforementioned general formula (D), the moiety corresponding to X is oxygen atom. Furthermore, while the moiety of the compound represented by the aforementioned general formula (D) corresponding to Y—$R^1$ of the compounds of the present invention represented by the general formula (I) mentioned below (substituent on the nitrogen atom of the 5-membered ring containing nitrogen) is limited to benzoyl group, said moiety is not limited to benzoyl group in the compounds of the present invention represented by the general formula (I) mentioned below.

After the publication of Non-patent documents 7 and 8 mentioned above and the priority date of this application, a patent application by the inventors of the present invention concerning morphinan derivatives including the compounds represented by the aforementioned general formula (D) was published (Patent document 3: WO2013/035833), and the inventors of the present invention also disclosed said compounds in literatures (Non-patent document 9, International Narcotic Research Conference, 2013, Abstracts, Jul. 14, 2013; Non-patent document 10, Opioid peptide symposium, Sep. 6, 2013), but these literatures do not describe the aminoalkyl group of the compounds of the present invention represented by the general formula (I) mentioned below as a moiety corresponding to the substituent R in the compound represented by the aforementioned general formula (D).

As a result of various researches, the inventors of the present invention found that the morphinan derivatives represented by the following general formula (I), tautomers and stereoisomers of the compounds, pharmaceutically acceptable salts thereof, and solvates thereof had superior opioid δ agonistic activity and opioid δ selectivity, and accomplished the present invention.

The present invention thus relates to a compound represented by the following general formula (I):

[Formula 5]

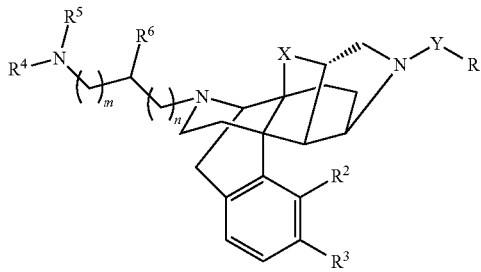

(I)

(wherein $R^1$ represents hydrogen, $C_{1-6}$ alkyl, $C_{1-6}$ cycloalkyl, $C_{6-10}$ aryl, heteroaryl (containing 1 to 4 heteroatoms selected from N, O and S as a ring-constituting atom), aralkyl (the aryl moiety has 6 to 10 carbon atoms, and the alkylene moiety has 1 to 5 carbon atoms), heteroarylalkyl (the heteroaryl contains 1 to 4 heteroatoms selected from N, O and S as a ring-constituting atom, and the alkylene moiety has 1 to 5 carbon atoms), cycloalkylalkyl (the cycloalkyl moiety has 3 to 6 carbon atoms, and the alkylene moiety has 1 to 5 carbon atoms), $C_{2-6}$ alkenyl, arylalkenyl (the aryl moiety has 6 to 10 carbon atoms, and the alkenyl moiety has 2 to 6 carbon atoms), heteroarylalkenyl (the heteroaryl contains 1 to 4 heteroatoms selected from N, O and S as a ring-constituting atom, and the alkenyl moiety has 2 to 6 carbon atoms), cycloalkylalkenyl (the cycloalkyl moiety has 3 to 6 carbon atoms, and the alkenyl moiety has 2 to 6 carbon atoms), $C_{4-6}$ cycloalkenyl, cycloalkenylalkyl (the cycloalkenyl moiety has 4 to 6 carbon atoms, and the alkylene moiety has 1 to 5 carbon atoms), or cycloalkenylalkenyl (the cycloalkenyl moiety has 4 to 6 carbon atoms, and the alkenyl moiety has 2 to 6 carbon atoms), $R^2$ and $R^3$, which are the same or different, represent hydrogen, hydroxy, cyano, carbamoyl, $C_{1-6}$ alkoxy, $C_{6-10}$ aryloxy, or $C_{1-6}$ alkanoyloxy, $R^4$ and $R^5$, which are the same or different, represent hydrogen, $C_{1-6}$ alkyl, $C_{3-6}$ cycloalkyl, $C_{6-10}$ aryl, cycloalkylalkyl (the cycloalkyl moiety has 3 to 6 carbon atoms, and the alkylene moiety has 1 to 5 carbon atoms), aralkyl (the aryl moiety has 6 to 10 carbon atoms, and the alkylene moiety has 1 to 5 carbon atoms), or heteroarylalkyl (the heteroaryl contains 1 to 4 heteroatoms selected from N, O and S as a ring-constituting atom, and the alkylene moiety has 1 to 5 carbon atoms), or $R^5$ and $R^4$ may combine together to form a 4- to 7-membered ring (which may contain a heteroatom selected from N, O and S as a ring-constituting atom other than the N atom to which $R^5$ binds) together with the nitrogen atom to which $R^5$ binds, $R^6$ represents hydrogen, hydroxy, $C_{1-6}$ alkyl, $C_{3-6}$ cycloalkyl, $C_{6-10}$ aryl, cycloalkylalkyl (the cycloalkyl moiety has 3 to 6 carbon atoms, and the alkylene moiety has 1 to 5 carbon atoms), aralkyl (the aryl moiety has 6 to 10 carbon atoms, and the alkylene moiety has 1 to 5 carbon atoms), or heteroarylalkyl (the heteroaryl contains 1 to 4 heteroatoms selected from N, O and S as a ring-constituting atom, and the alkylene moiety has 1 to 5 carbon atoms), or $R^6$ and $R^5$ may combine together to form a 4- to 7-membered ring (which may contain a heteroatom selected from N, O and S as a ring-constituting atom other than the N atom to which $R^5$ binds) together with the nitrogen atom to which $R^5$ binds, X represents O or $CH_2$, Y represents C=O, C(=O)O, C(=O)$NR^7$, $SO_2$, or an atomic bond, wherein $R^7$ represents hydrogen, $C_{1-6}$ alkyl, aralkyl (the aryl moiety has 6 to 10 carbon atoms, and the alkylene moiety has 1 to 5 carbon atoms), heteroarylalkyl (the heteroaryl contains 1 to 4 heteroatoms selected from N, O and S as a ring-constituting atom, and the alkylene moiety has 1 to 5 carbon atoms), or cycloalkylalkyl (the cycloalkyl moiety has 3 to 6 carbon atoms, and the alkylene moiety has 1 to 5 carbon atoms), or the N atom to which $R^7$ binds and $R^1$ may combine together to form a 4- to 7-membered ring (which may contain a heteroatom selected from N, O and S as a ring-constituting atom other than the N atom to which $R^7$ binds), and m and n, which are the same or different, represent an integer of 0 to 2 (m and n are not 0 at the same time), wherein the $C_{1-6}$ alkyl regarding $R^1$, $R^4$, $R^5$ and $R^6$, the 4- to 7-membered ring formed by $R^5$ and $R^6$, and the 4- to 7-membered ring formed by $R^5$ and $R^4$ may be substituted with hydroxy group, and the aryl moiety of the $C_{6-10}$ aryl and the aralkyl (the aryl moiety has 6 to 10 carbon atoms, and the alkylene moiety has 1 to 5 carbon atoms) regarding $R^1$, and the heteroaryl moiety of the heteroaryl (containing 1 to 4 heteroatoms selected from N, O and S as a ring-constituting atom) and the heteroarylalkyl (the heteroaryl contains 1 to 4 heteroatoms selected from N, O and S as a ring-constituting atom, and the alkylene moiety has 1 to 5 carbon atoms) regarding $R^1$ may be substituted with at least one substituent selected from $C_{1-6}$ alkyl, $C_{1-6}$ alkoxy, $C_{1-6}$ alkanoyloxy, hydroxy, alkoxycarbonyl (the alkoxy moiety has 1 to 6 carbon atoms), carbamoyl, alkylcarbamoyl (the alkyl moiety has 1 to 6 carbon atoms), dialkylcarbamoyl (each alkyl moiety has 1 to 6 carbon atoms), halogen, nitro, cyano, $C_{1-6}$ alkyl substituted with 1 to 3 halogens, $C_{1-6}$ alkoxy substituted with 1 to 3 halogens, phenyl, heteroaryl (containing 1 to 4 heteroatoms selected from N, O and S as a ring-constituting atom), phenoxy, phenylalkyl (the alkylene moiety has 1 to 3 carbon atoms), methylenedioxy, and $NR^8R^9$, wherein $R^8$ and $R^9$ independently represent hydrogen, $C_{1-6}$ alkyl, $C_{2-6}$ alkenyl, $C_{3-6}$ cycloalkyl, $C_{1-6}$ alkanoyl, or alkoxycarbonyl (the alkoxy moiety has 1 to 6 carbon atoms), or $R^8$ and $R^9$ may form, together with the N atom to which they bind, a 4- to 7-membered ring which may further contain a heteroatom selected from N, O and S), a tautomer or stereoisomer of the compound, or a pharmaceutically acceptable salt thereof, or a solvate thereof.

The present invention also relates to a medicament comprising the morphinan derivative represented by the aforementioned general formula (I), a tautomer or stereoisomer of the compound, or a pharmaceutically acceptable salt thereof, or a solvate thereof.

The present invention also relates to a pharmaceutical composition containing the morphinan derivative represented by the aforementioned general formula (I), a tautomer or stereoisomer of the compound, or a pharmaceutically acceptable salt thereof, or a solvate thereof as an active ingredient.

The present invention also relates to an analgesic comprising the morphinan derivative represented by the aforementioned general formula (I), a tautomer or stereoisomer of the compound, or a pharmaceutically acceptable salt thereof, or a solvate thereof as an active ingredient.

The present invention also relates to an antianxiety drug comprising the morphinan derivative represented by the aforementioned general formula (I), a tautomer or stereoisomer of the compound, or a pharmaceutically acceptable salt thereof, or a solvate thereof as an active ingredient.

The present invention further relates to an antidepressant comprising a morphinan derivative represented by the aforementioned general formula (I), a tautomer or stereoisomer of the compound, or a pharmaceutically acceptable salt thereof, or a solvate thereof as an active ingredient.

MODES FOR CARRYING OUT THE INVENTION

Hereafter, the present invention will be explained in more detail.

Preferred embodiments of the morphinan derivative represented by the aforementioned general formula (I), a tautomer or stereoisomer of the compound, or a pharmaceutically acceptable salt thereof, or a solvate thereof include the followings.

(1) The morphinan derivative represented by the aforementioned general formula (I), a tautomer or stereoisomer of the compound, or a pharmaceutically acceptable salt thereof, or a solvate thereof, wherein:

$R^1$ represents hydrogen, $C_{1-6}$ alkyl, $C_{3-6}$ cycloalkyl, $C_{6-10}$ aryl, heteroaryl (containing 1 to 4 heteroatoms selected from N, O and S as a ring-constituting atom), aralkyl (the aryl moiety has 6 to 10 carbon atoms, and the alkylene moiety has 1 to 5 carbon atoms), heteroarylalkyl (the heteroaryl contains 1 to 4 heteroatoms selected from N, O and S as a ring-constituting atom, and the alkylene moiety has 1 to 5 carbon atoms), cycloalkylalkyl (the cycloalkyl moiety has 3 to 6 carbon atoms, and the alkylene moiety has 1 to 5 carbon atoms), $C_{2-6}$ alkenyl, arylalkenyl (the aryl moiety has 6 to 10 carbon atoms, and the alkenyl moiety has 2 to 6 carbon atoms), heteroarylalkenyl (the heteroaryl contains 1 to 4 heteroatoms selected from N, O and S as a ring-constituting atom, and the alkenyl moiety has 2 to 6 carbon atoms), cycloalkylalkenyl (the cycloalkyl moiety has 3 to 6 carbon atoms, and the alkenyl moiety has 2 to 6 carbon atoms), $C_{4-6}$ cycloalkenyl, cycloalkenylalkyl (the cycloalkenyl moiety has 4 to 6 carbon atoms, and the alkylene moiety has 1 to 5 carbon atoms), or cycloalkenylalkenyl (the cycloalkenyl moiety has 4 to 6 carbon atoms, and the alkenyl moiety has 2 to 6 carbon atoms), $R^2$ and $R^3$, which are the same or different, represent hydrogen, hydroxy, cyano, carbamoyl, $C_{1-6}$ alkoxy, $C_{6-10}$ aryloxy, or $C_{1-6}$ alkanoyloxy, $R^4$, $R^5$ and $R^6$, which are the same or different, represent hydrogen, $C_{1-6}$ alkyl, $C_{3-6}$ cycloalkyl, $C_{6-10}$ aryl, cycloalkylalkyl (the cycloalkyl moiety has 3 to 6 carbon atoms, and the alkylene moiety has 1 to 5 carbon atoms), aralkyl (the aryl moiety has 6 to 10 carbon atoms, and the alkylene moiety has 1 to 5 carbon atoms), or heteroarylalkyl (the heteroaryl contains 1 to 4 heteroatoms selected from N, O and S as a ring-constituting atom, and the alkylene moiety has 1 to 5 carbon atoms), or $R^5$ and $R^4$ or $R^6$ may combine together to form a 4- to 7-membered ring (which may contain a heteroatom selected from N, O and S as a ring-constituting atom other than the N atom to which $R^5$ binds) together with the nitrogen atom to which $R^5$ binds, X represents O or $CH_2$, Y represents C=O, C(=O)O, C(=O)$NR^7$, $SO_2$, or an atomic bond, wherein $R^7$ represents hydrogen, $C_{1-6}$ alkyl, aralkyl (the aryl moiety has 6 to 10 carbon atoms, and the alkylene moiety has 1 to 5 carbon atoms), heteroarylalkyl (the heteroaryl contains 1 to 4 heteroatoms selected from N, O and S as a ring-constituting atom, and the alkylene moiety has 1 to 5 carbon atoms), cycloalkylalkyl (the cycloalkyl moiety has 3 to 6 carbon atoms, and the alkylene moiety has 1 to 5 carbon atoms), or the N atom to which $R^7$ binds and $R^1$ may combine together to form a 4- to 7-membered ring (which may contain a heteroatom selected from N, O and S as a ring-constituting atom other than the N atom to which $R^7$ binds), and m and n, which are the same or different, represent an integer of 0 to 2 (m and n are not 0 at the same time), wherein the $C_{1-6}$ alkyl regarding $R^1$, $R^4$, $R^5$ and $R^6$, the 4- to 7-membered ring formed by $R^5$ and $R^6$, and the 4- to 7-membered ring formed by $R^5$ and $R^4$ may be substituted with hydroxy group, and the aryl moiety of the $C_{6-10}$ aryl and the aralkyl (the aryl moiety has 6 to 10 carbon atoms, and the alkylene moiety has 1 to 5 carbon atoms) regarding $R^1$, and the heteroaryl moiety of the heteroaryl (containing 1 to 4 heteroatoms selected from N, O and S as a ring-constituting atom) and the heteroarylalkyl (the heteroaryl contains 1 to 4 heteroatoms selected from N, O and S as a ring-constituting atom, and the alkylene moiety has 1 to 5 carbon atoms) regarding $R^1$ may be substituted with at least one substituent selected from $C_{1-6}$ alkyl, $C_{1-6}$ alkoxy, $C_{1-6}$ alkanoyloxy, hydroxy, alkoxycarbonyl (the alkoxy moiety has 1 to 6 carbon atoms), carbamoyl, alkylcarbamoyl (the alkyl moiety has 1 to 6 carbon atoms), dialkylcarbamoyl (each alkyl moiety has 1 to 6 carbon atoms), halogen, nitro, cyano, $C_{1-6}$ alkyl substituted with 1 to 3 halogens, $C_{1-6}$ alkoxy substituted with 1 to 3 halogens, phenyl, heteroaryl (containing 1 to 4 heteroatoms selected from N, O and S as a ring-constituting atom), phenoxy, phenylalkyl (the alkylene moiety has 1 to 3 carbon atoms), methylenedioxy, and $NR^8R^9$, wherein $R^8$ and $R^9$ independently represent hydrogen, $C_{1-6}$ alkyl, $C_{2-6}$ alkenyl, $C_{3-6}$ cycloalkyl, $C_{1-6}$ alkanoyl, or alkoxycarbonyl (the alkoxy moiety has 1 to 6 carbon atoms), or $R^8$ and $R^9$ may form, together with the N atom to which they bind, a 4- to 7-membered ring which may further contain a heteroatom selected from N, O and S.

(2) The morphinan derivative represented by the aforementioned general formula (I), or the morphinan derivative, a tautomer or stereoisomer of the compound, or a pharmaceutically acceptable salt thereof, or a solvate thereof according to (1) mentioned above, wherein X is $CH_2$.

(3) The morphinan derivative represented by the aforementioned general formula (I), or the morphinan derivative, a tautomer or stereoisomer of the compound, or a pharmaceutically acceptable salt thereof, or a solvate thereof according to (1) or (2) mentioned above, wherein $R^4$, $R^5$ and $R^6$, which are the same or different, are hydrogen, $C_{1-6}$ alkyl, or cycloalkylalkyl (the cycloalkyl moiety has 3 to 6 carbon atoms, and the alkylene moiety has 1 to 5 carbon atoms).

(4) The morphinan derivative represented by the aforementioned general formula (I), or the morphinan derivative, a tautomer or stereoisomer of the compound, or a pharmaceutically acceptable salt thereof, or a solvate thereof according to (1) or (2) mentioned above, wherein $R^5$ and $R^4$ or $R^6$ combine together to form a 4- to 7-membered ring (which may contain a heteroatom selected from N, O and S as a ring-constituting atom other than the N atom to which $R^5$ binds) together with the N atom to which $R^5$ binds.

(5) The morphinan derivative represented by the aforementioned general formula (I), or the morphinan derivative, a tautomer or stereoisomer of the compound, or a pharmaceutically acceptable salt thereof, or a solvate thereof according to (1) or (2) mentioned above, wherein $R^5$ and $R^6$ combine together to form a 4- to 7-membered ring (which may contain a heteroatom selected from N, O and S as a ring-constituting atom other than the N atom to which $R^5$ binds) together with the N atom to which $R^5$ binds.

(6) The morphinan derivative represented by the aforementioned general formula (I), or the morphinan derivative, a tautomer or stereoisomer of the compound, or a pharmaceutically acceptable salt thereof, or a solvate thereof according to any one of (1) to (5) mentioned above, wherein the sum of m and n is an integer of 1 to 3.

(7) The morphinan derivative represented by the aforementioned general formula (I), or the morphinan derivative, a tautomer or stereoisomer of the compound, or a pharmaceutically acceptable salt thereof, or a solvate thereof according to any one of (1) to (5) mentioned above, wherein n is 1.

(8) The morphinan derivative represented by the aforementioned general formula (I), or the morphinan derivative, a tautomer or stereoisomer of the compound, or a pharmaceutically acceptable salt thereof, or a solvate thereof according to (2), (6), or (7) mentioned above, wherein $R^6$ is hydroxy group.

(9) The morphinan derivative represented by the aforementioned general formula (I), or the morphinan derivative, a tautomer or stereoisomer of the compound, or a pharmaceutically acceptable salt thereof, or a solvate thereof according to (1), (2), (6), or (7) mentioned above, wherein $R^6$ is $C_{1-6}$ alkyl substituted with hydroxy group.

(10) The morphinan derivative represented by the aforementioned general formula (I), or the morphinan derivative, a tautomer or stereoisomer of the compound, or a pharmaceutically acceptable salt thereof, or a solvate thereof according to any one of (1) to (9) mentioned above, wherein Y is C=O, C(=O)$NR^7$, or an atomic bond.

(11) The morphinan derivative represented by the aforementioned general formula (I), or the morphinan derivative, a tautomer or stereoisomer of the compound, or a pharmaceutically acceptable salt thereof, or a solvate thereof according to any one of (1) to (10) mentioned above, wherein $R^1$ is aryl or heteroaryl which may have a substituent.

(12) The morphinan derivative represented by the aforementioned general formula (I), or the morphinan derivative, a tautomer or stereoisomer of the compound, or a pharmaceutically acceptable salt thereof, or a solvate thereof according to any one of (1) to (11) mentioned above, wherein $R^2$ is hydrogen, and $R^3$ is hydrogen, hydroxy, carbamoyl, $C_{1-6}$ alkoxy, or $C_{1-6}$ alkanoyloxy.

(13) The morphinan derivative represented by the aforementioned general formula (I), or the morphinan derivative, a tautomer or stereoisomer of the compound, or a pharmaceutically acceptable salt thereof, or a solvate thereof according to any one of (1) to (11) mentioned above, wherein $R^2$ is hydrogen, and $R^3$ is hydroxy.

(14) The morphinan derivative represented by the aforementioned general formula (I), or the morphinan derivative, a tautomer or stereoisomer of the compound, or a pharmaceutically acceptable salt thereof, or a solvate thereof according to any one of (1) to (13) mentioned above, wherein the salt is an acid addition salt.

In the present invention:

Examples of the $C_{1-10}$ alkyl include methyl, ethyl, propyl, i-propyl, butyl, t-butyl, pentyl, neopentyl, hexyl, and the like.

Examples of the $C_{1-6}$ alkyl substituted with 1 to 3 halogens include 2-chloroethyl, 2-fluoroethyl, 3-fluoropropyl, 2,2-difluoroethyl, trifluoromethyl, 3,3,3-trifluoropropyl, and the like.

Examples of the $C_{2-6}$ alkenyl include 2-propenyl, 3-methyl-2-butenyl, and the like.

Examples of the cycloalkylalkyl (the cycloalkyl moiety has 3 to 6 carbon atoms, and the alkylene moiety has 1 to 5 carbon atoms) include methyl, ethyl, and the like substituted with $C_{3-6}$ cycloalkyl such as cyclopropyl, cyclobutyl, cyclopentyl, and cyclohexyl.

Examples of the aralkyl (the aryl moiety has 6 to 10 carbon atoms, and the alkylene moiety has 1 to 5 carbon atoms) include benzyl group, and phenethyl group.

Examples of the $C_{3-6}$ cycloalkyl include cyclopropyl, cyclobutyl, cyclopentyl, cyclohexyl, and the like.

Examples of the $C_{3-10}$ aryl include phenyl, naphthyl, and the like.

Examples of the heteroaryl (containing 1 to 4 heteroatoms selected from N, O and S as a ring-constituting atom) include monocyclic heteroaryls comprising 5 to 10 ring-constituting atoms such as pyridyl, furyl, imidazolyl, pyrimidinyl, pyrazinyl, and thiazolyl, and bicyclic heteroaryls such as quinolyl, and indolyl.

Examples of the heteroarylalkyl (the heteroaryl contains 1 to 4 heteroatoms selected from N, O and S as a ring-constituting atom, and the alkylene moiety has 1 to 5 carbon atoms) include monocyclic heteroarylalkyls comprising 5 to 10 ring-constituting atoms in the heteroaryl such as (pyridin-2-yl)methyl, (pyridin-3-yl)methyl, (pyridin-4-yl)methyl, 2-(pyridin-2-yl)ethyl, (furan-2-yl)methyl, (furan-3-yl)methyl, (imidazol-2-yl)methyl, (imidazol-4-yl)methyl, (imidazol-5-yl)methyl, (thiazol-2-yl)methyl, (thiazol-4-yl)methyl, (thiazol-5-yl)methyl, (thiophen-2-yl)methyl, and 2-(thiophen-2-yl)ethyl, and bicyclic heteroarylalkyls such as (quinolin-3-yl)methyl, and (indol-3-yl)methyl.

Examples of the arylalkenyl (the aryl moiety has 6 to 10 carbon atoms, and the alkenyl moiety has 2 to 6 carbon atoms) include 2-propenyl, 3-methyl-2-butenyl, and the like substituted with phenyl, naphthyl, or the like.

Examples of the heteroarylalkenyl (the heteroaryl contains 1 to 4 heteroatoms selected from N, O and S as a ring-constituting atom, and the alkenyl moiety has 2 to 6 carbon atoms) include 2-propenyl, 3-methyl-2-butenyl, and the like substituted with pyridyl, furyl, imidazolyl, thiazolyl, or the like.

Examples of the cycloalkylalkenyl (the cycloalkyl moiety has 3 to 6 carbon atoms, and the alkenyl moiety has 2 to 6 carbon atoms) include 2-propenyl, 3-methyl-2-butenyl, and the like substituted with $C_{3-6}$ cycloalkyl such as cyclopropyl, cyclobutyl, cyclopentyl, and cyclohexyl.

Examples of the $C_{4-6}$ cycloalkenyl include cyclobutenyl, cyclopentenyl, and the like.

Examples of the cycloalkenylalkyl (the cycloalkenyl moiety has 4 to 6 carbon atoms, and the alkylene moiety has 1 to 5 carbon atoms) include methyl, ethyl, and the like substituted with cyclobutenyl, cyclopentenyl, or the like.

Examples of the cycloalkenylalkenyl (the cycloalkenyl moiety has 4 to 6 carbon atoms, and the alkenyl moiety has 2 to 6 carbon atoms) include 2-propenyl, and 3-methyl-2-butenyl substituted with cyclobutenyl, cyclopentenyl, or the like.

Examples of the $C_{2-6}$ alkyl substituted with $C_{1-6}$ alkoxy include 2-methoxyethyl, and the like.

Examples of the $C_{1-6}$ alkanoyl include acetyl, propionyl, and the like.

Examples of the $C_{1-6}$ alkoxy include methoxy, ethoxy, propoxy, and the like.

Examples of the $C_{1-6}$ alkanoyloxy include acetoxy, and the like.

Examples of the alkoxycarbonyl (the alkoxy moiety has 1 to 6 carbon atoms) include methoxycarbonyl, ethoxycarbonyl, and the like.

Examples of the halogen include fluorine, chlorine, bromine, and the like.

Examples of the $C_{1-6}$ alkoxy substituted with 1 to 3 halogens include fluoromethoxy, trifluoromethoxy, and the like.

Examples of the phenylalkyl (the alkylene moiety has 1 to 3 carbon atoms) include benzyl, and the like.

Examples of the $C_{3-10}$ aryloxy include phenoxy, and the like.

Examples of the alkylcarbamoyl (the alkyl moiety has 1 to 6 carbon atoms) include ethylcarbamoyl, and the like.

Examples of the dialkylcarbamoyl (each alkyl moiety has 1 to 6 carbon atoms) include diethylcarbamoyl, and the like.

Examples of the 4- to 7-membered ring formed by $R^5$ and $R^4$ or $R^6$ combined together, together with the nitrogen atom to which $R^5$ binds (which may contain a heteroatom selected from N, O and S as a ring-constituting atom other than the N atom to which $R^5$ binds), the 4- to 7-membered ring formed by the N atom to which $R^7$ binds and $R^1$ combined together (which may contain a heteroatom selected from N, O and S as a ring-constituting atom other than the N atom to which $R^7$ binds), and the 4 to 7-membered ring formed by $R^8$ and $R^9$ combined together, together with the N atom to which they bind, which may further contain a heteroatom selected from N, O and S, include azetidine ring, pyrrolidine ring, piperidine ring, piperazine ring, morpholine ring, and the like.

Among the morphinan derivative represented by the aforementioned general formula (I), a tautomer or stereoisomer of the compound, and a pharmaceutically acceptable salt thereof, preferred examples of the pharmacologically acceptable acid include acid addition salts, and examples of acid addition salts include salts with an inorganic acid such as hydrochloride, and sulfate, and salts with an organic acid such as fumarate, oxalate, methanesulfonate, and camphorsulfonate.

Among the morphinan derivative represented by the aforementioned general formula (I), a tautomer or stereoisomer of the compound, a pharmaceutically acceptable salt thereof, and a solvate thereof, examples of the stereoisomer include cis- and trans-isomers, racemates, optically active compounds, and the like.

Among the morphinan derivative represented by the aforementioned general formula (I), a tautomer or stereoisomer of the compound, a pharmaceutically acceptable salt thereof, and a solvate thereof, the solvate is a pharmaceutically acceptable solvate of the compound of the present invention or a salt thereof, and includes hydrate.

Hereafter, methods for preparing the morphinan derivative represented by the aforementioned general formula (I), a tautomer or stereoisomer of the compound, or a pharmaceutically acceptable salt thereof, or a solvate thereof will be shown below.

(Preparation Method 1)

Morphinan derivative represented by the aforementioned general formula (I), wherein $R^2$ is hydrogen, hydroxy, $C_{1-6}$ alkoxy or $C_{6-10}$ aryloxy, $R^3$ is hydrogen, $C_{1-6}$ alkoxy, $C_{6-10}$ aryloxy, cyano, or $CONH_2$, Y is C=O, $SO_2$, C(=O)O or C(=O)$NR^7$, and $R^4$ is hydrogen

[Formula 6]

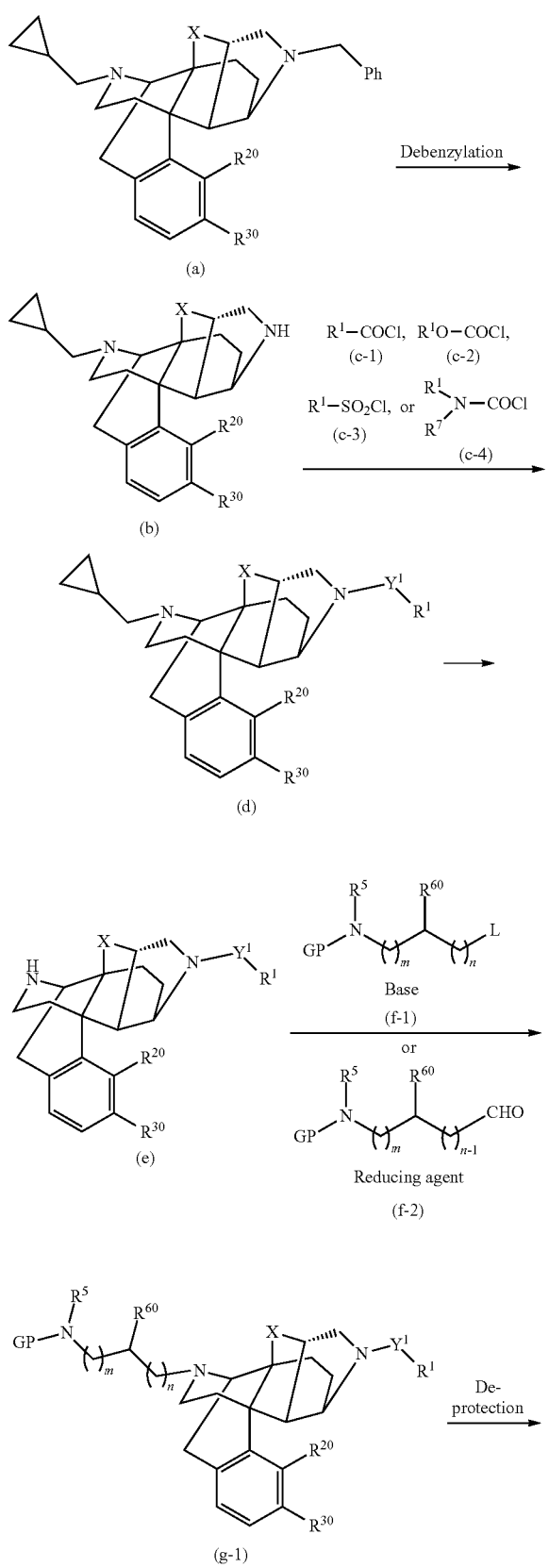

$R^{20}$: Hydrogen, hydroxy, $C_{1-6}$ alkoxy, or $C_{6-10}$ aryloxy
$R^{30}$: Hydrogen, $C_{1-6}$ alkoxy, $C_{6-10}$ aryloxy, cyano, or $CONH_2$
$Y^1$: C=O, $SO_2$, C(=O)O, or C(=O)$NR^7$
PG: Protective group such as t-butoxycarbonyl group
L: Leaving group such as halogen atom and p-toluenesulfonyloxy group
$R^{60}$: The same as $R^6$ mentioned above provided that hydroxy group is excluded.
$R^1$, $R^5$, $R^7$, X, m, and n have the same meanings as those defined above.

First Step

The compound (b) can be obtained by catalytic reduction of the compound (a) (synthesis method will be described later), or the like. As the catalyst for this reaction, palladium/carbon, palladium hydroxide, and the like are used, and as the solvent, ethanol, acetic acid, and the like are used.

Second Step

The compound (d) can be obtained by reacting the compound (b) with the compound (c-1), (c-2), (c-3), or (c-4) in a solvent such as dichloromethane and tetrahydrofuran (THF) in the presence of a base such as triethylamine. When $Y^1$ of the compound (d) is C(=O), a corresponding carboxylic acid may be used instead of the compound (c-1) in the presence of a condensing agent. When $Y^1$ is C(=O)$NHR^1$, an isocyanate ($R^1$—NCO) may be used instead of the compound (c-4).

Third Step

The compound (e) is synthesized from the compound (d) by any of the following methods.

Method a:
Known de-N-alkylation method consisting of a reaction of the compound (d) and a chloroformic acid ester, and a subsequent decarbamation reaction (Bioorg. Med. Chem. Lett., 2010, 20, 6302, etc.)

Method b:
Method of Using Diethyl Azodicarboxylate (Synthetic Communications, 1995, 25, 829, etc.)

Fourth Step

The compound (g-1) is synthesized from the compound (e) by any of the following methods.

Method c:
Method of alkylating the compound (e) by using the compound (f-1) in a solvent such as acetonitrile and N,N-dimethylformamide (DMF) in the presence of a base such as sodium hydrogencarbonate Method d:
Method of Performing a Reductive Amination Reaction Between the Compounds (e) and (f-2)

In this case, as the reducing agent, sodium triacetoxyborohydride, sodium cyanoborohydride, and the like are used, and the solvent is appropriately chosen according to the type of the reducing agent.

Fifth Step

When the protective group of the compound (g-1) is t-butoxycarbonyl group, the compound (g-1) can be converted into the compound (g-2) of the present invention by allowing an acid such as trifluoroacetic acid and hydrochloric acid to act on the compound (g-1).

As the compound (a) as the starting material of the preparation method 1, the compounds (a-1), (a-2), and (a-3) are synthesized from the compound (o) (described in WO2012/102360; Tetrahedron, 2011, 67, 6682) according to the following method.

[Formula 7]

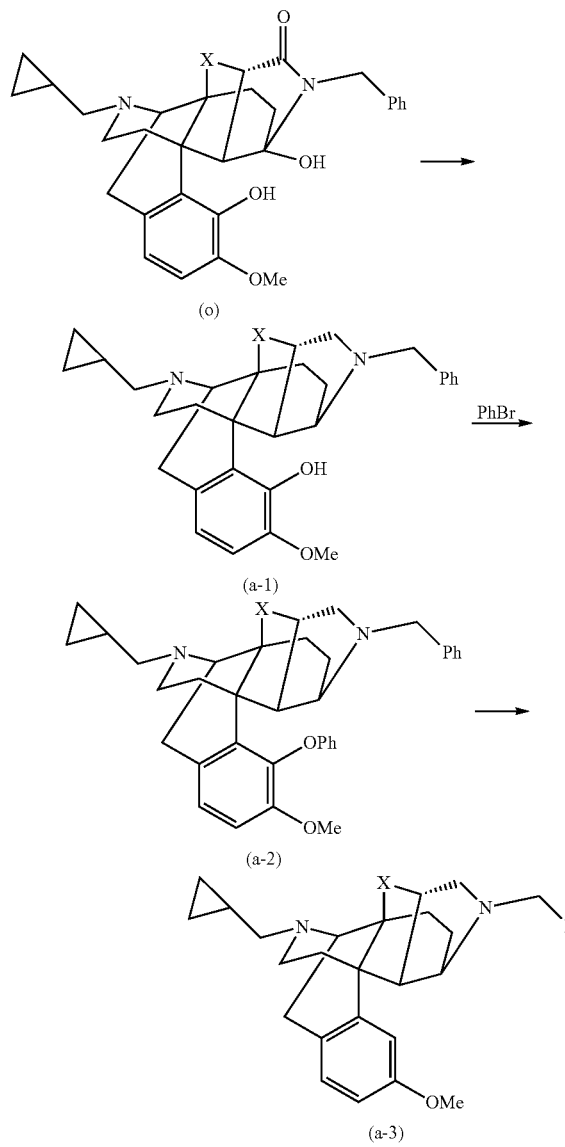

X has the same meaning as defined above.

Compound (a-1)

The compound (a-1) is synthesized by reducing the compound (o) with a borane-THF complex or the like in a solvent such as THF.

Compound (a-2)

The compound (a-2) is synthesized by reacting the compound (a-1) with bromobenzene in a solvent such as pyridine in the presence of a catalyst such as copper powder and a base such as potassium carbonate.

Compound (a-3)

The compound (a-3) is synthesized by the Birch reduction of the compound (a-2). In this reaction, Sodium silica gel Stage I, and ethylenediamine are used as reagents in a solvent such as THF.

The synthesis intermediate of the preparation method 1, the compound (d), wherein $R^{20}$ is hydrogen, and $R^{30}$ is hydrogen, cyano, or $CONH_2$ is synthesized by the following methods.

(1) The compound where $R^{30}$ is cyano, or $CONH_2$ (compounds (d-3) and (d-4))

[Formula 8]

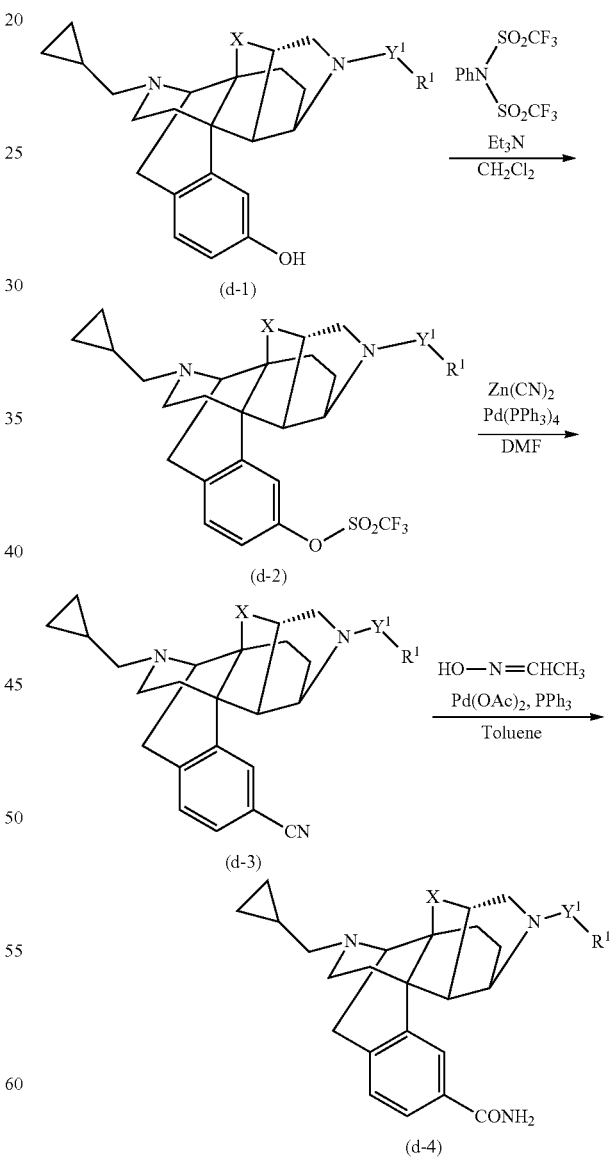

$Y^1$: C=O, $SO_2$, C(=O)O, or C(=O)$NR^7$ $R^1$, $R^7$ and X have the same meanings as those defined above.

As shown in the aforementioned scheme, the compound (d-3) is synthesized from the compound (d-1) (synthesis method will be described later) in two steps (first step, trifluoromethanesulfonylation of hydroxy group; second step, introduction of cyano group in the presence of a palladium catalyst). The compound (d-4) is synthesized by the method described in the aforementioned scheme, or a usual hydrolysis reaction of the compound (d-3).

(2) The Compound Wherein $R^{30}$ is Hydrogen (Compound (d-6))

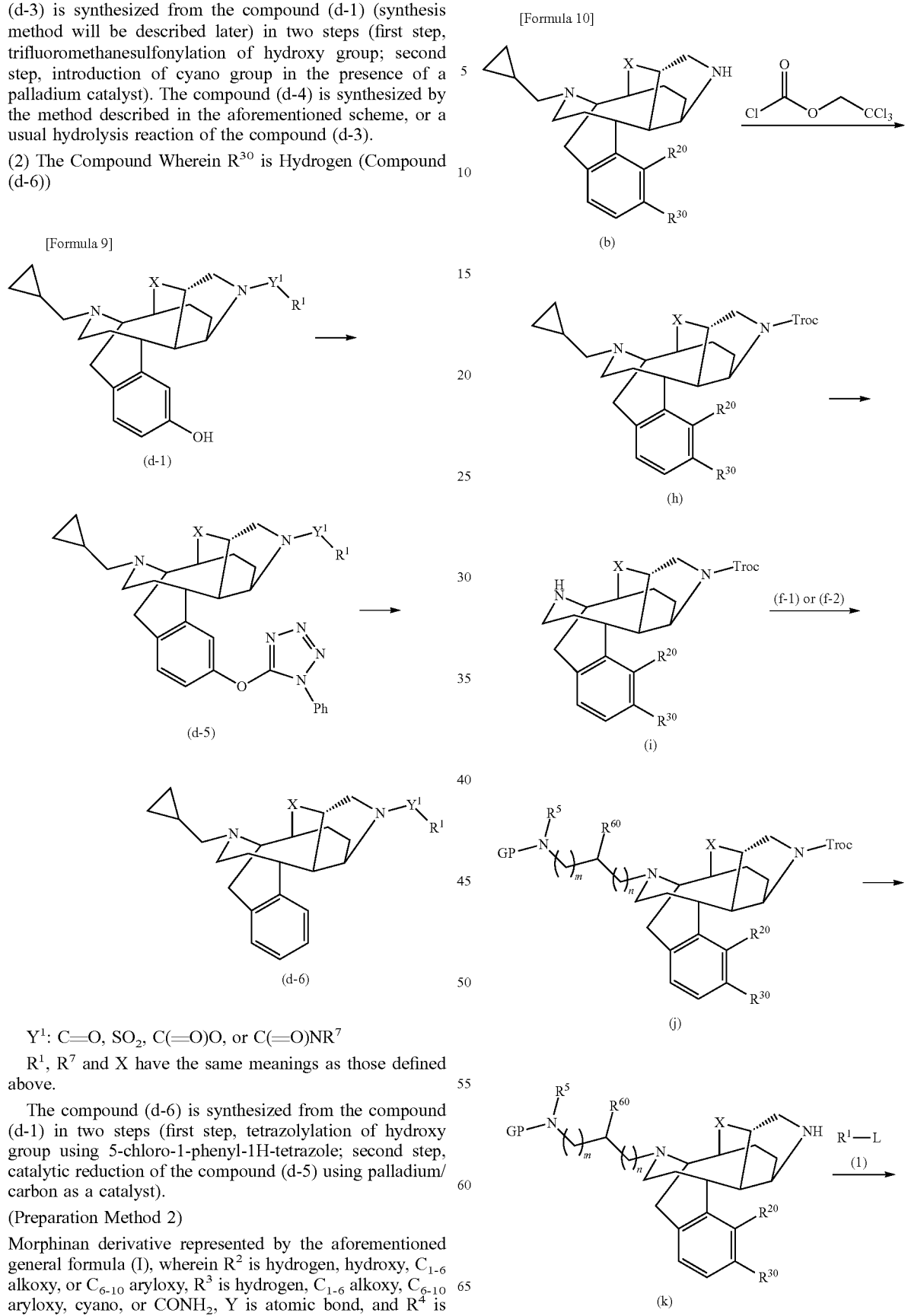

$Y^1$: C=O, SO$_2$, C(=O)O, or C(=O)NR$^7$ $R^1$, $R^7$ and X have the same meanings as those defined above.

The compound (d-6) is synthesized from the compound (d-1) in two steps (first step, tetrazolylation of hydroxy group using 5-chloro-1-phenyl-1H-tetrazole; second step, catalytic reduction of the compound (d-5) using palladium/carbon as a catalyst).

(Preparation Method 2)

Morphinan derivative represented by the aforementioned general formula (I), wherein $R^2$ is hydrogen, hydroxy, $C_{1-6}$ alkoxy, or $C_{6-10}$ aryloxy, $R^3$ is hydrogen, $C_{1-6}$ alkoxy, $C_{6-10}$ aryloxy, cyano, or CONH$_2$, Y is atomic bond, and $R^4$ is hydrogen -continued

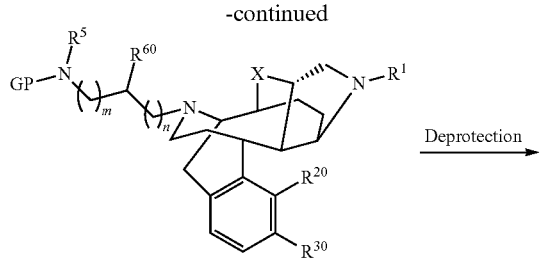

(k)

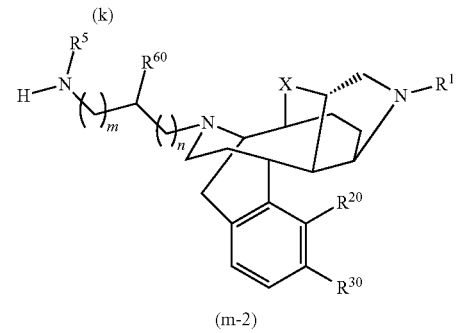

(m-2)

Troc: 2,2,2-Trichloroethoxycarbonyl group
$R^{20}$: Hydrogen, hydroxy, $C_{1-6}$ alkoxy, or $C_{6-10}$ aryloxy
$R^{30}$: Hydrogen, $C_{1-6}$ alkoxy, $C_{6-10}$ aryloxy, cyano, or $CONH_2$
PG: Protective group such as t-butoxycarbonyl group
L: Leaving group such as halogen atom, and p-toluenesulfonyloxy group
$R^{60}$: The same as $R^6$ mentioned above provided that hydroxy group is excluded
$R^1$, $R^5$, X, m, and n have the same meanings as those defined above.

First Step

The compound (h) can be obtained by reacting the compound (b) (described in the preparation method 1) with 2,2,2-trichloroethyl chloroformate in a solvent such as dichloromethane in the presence of a base such as potassium carbonate.

Second and Third Steps

The compound (h) is converted into the compound (i), and then into the compound (j) using the methods described in the preparation method 1, third and fourth steps.

Fourth Step

The compound (k) can be obtained by treating the compound (j) with zinc powder in a solvent such as ethanol and acetic acid.

Fifth Step

When the reagent (1) is an alkyl halide or halogenated heteroaryl, the compound (m-1) can be obtained by reacting the compound (k) with the reagent (1) in a solvent such as acetonitrile and DMF in the presence of a base such as sodium hydrogencarbonate.

When the reagent (1) is aryl halide or halogenated heteroaryl, the compound (m-1) can be obtained by a crossing coupling reaction of the reagent (1) and the compound (k) in the presence of a palladium catalyst.

Sixth Step

When the protective group of the compound (m-1) is t-butoxycarbonyl group, the compound (m-1) can be converted into the compound (m-2) of the present invention by the method described in the preparation method 1, fifth step.

(Preparation Method 3)

Morphinan Derivative Represented by the Aforementioned General Formula (I), Wherein $R^2$ is Hydrogen, $R^3$ is Methoxy or Hydroxy, and $R^4$ is Hydrogen This compound is synthesized by any of the following methods A to E.

(1) Method A (Y is C=O, $SO_2$, C(=O) O, or C(=O)$NR^7$)

[Formula 11]

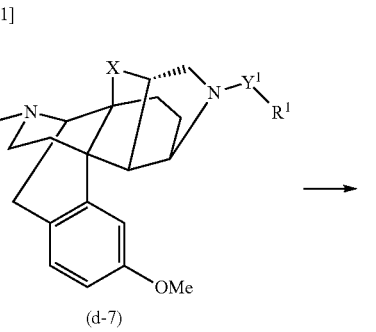

(d-7)

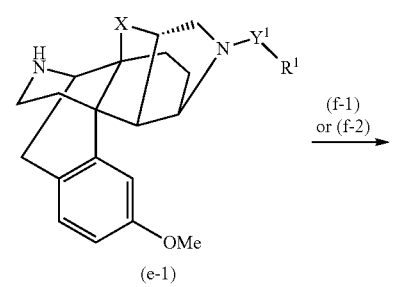

(e-1)

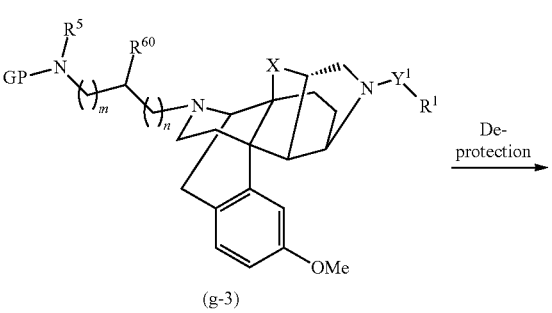

(g-3)

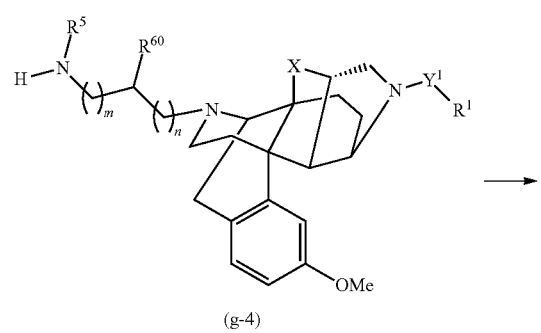

(g-4)

-continued

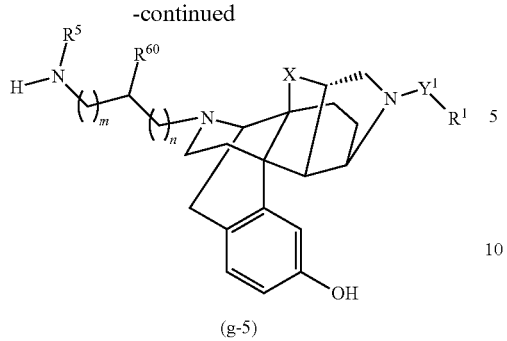

(g-5)

$Y^1$: C=O, SO$_2$, C(=O)O, or C(=O)NR$^7$
PG: Protective group such as t-butoxycarbonyl group
R$^{60}$: The same as R$^6$ mentioned above provided that hydroxy group is excluded
R$^1$, R$^5$, R$^7$, X, m, and n have the same meanings as those defined above First Step The compound (e-1) can be obtained by applying the method described in the preparation method 1, third step to the compound (d-7) (synthesized from the compound (a-3) according to the methods described in the preparation method 1, first and second steps).

Second and Third Steps

The compound (e-1) is converted into the compound (g-3), and then into the compound (g-4) of the present invention using the methods described in the preparation method 1, fourth and fifth steps.

Fourth Step

The compound (g-5) of the present invention represented by the general formula (I) wherein R$^3$ is hydroxy group is synthesized by a method of allowing boron tribromide or the like to act on the compound (g-4) in dichloromethane, or a method of allowing an alkanethiol such as 1-dodecanethiol to act on the compound (g-4) in DMF in the presence of a base such as potassium t-butoxide.

(2) Method B (Y is C=O, SO$_2$, C(=O)O, or C(=O)NR$^7$)

[Formula 12]

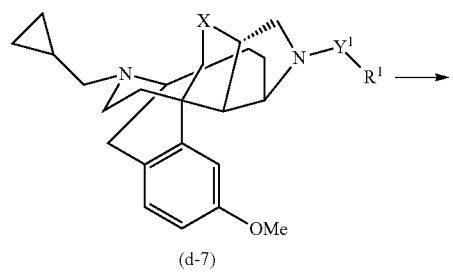

(d-7)

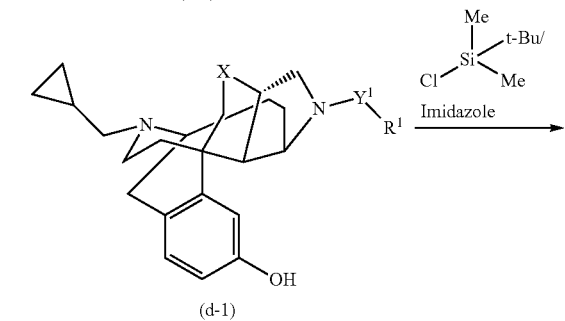

(d-1)

-continued

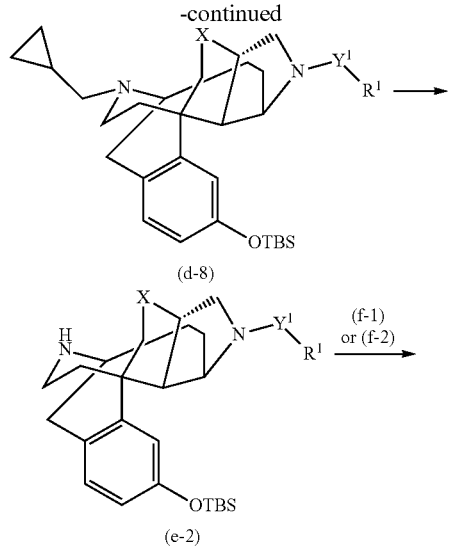

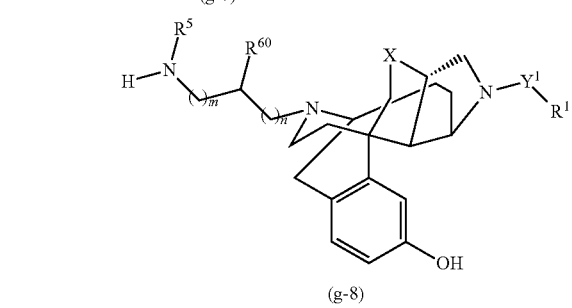

TBS: t-Butyldimethylsilyl group
$Y^1$: C=O, SO$_2$, C(=O)O, or C(=O)NR$^7$
PG: Protective group such as t-butoxycarbonyl group
R$^{60}$: The same as R$^6$ mentioned above provided that hydroxy group is excluded R$^1$, R$^5$, R$^7$, X, m, and n have the same meanings as defined above.

First Step

The compound (d-1) can be obtained by applying the method described in the method A, fourth step to the compound (d-7).

Second Step

The compound (d-8) can be obtained by reacting the compound (d-1) with t-buthyldimethylchlorosilane in a solvent such as DMF in the presence of a base such as imidazole.

Third and Fourth Steps

The compound (d-8) is converted into the compound (e-2), and then into the compound (g-6) by using the methods described in the preparation method 1, third and fourth steps.

Fifth Step

The compound (g-7) can be obtained by treating the compound (g-6) with tetra-n-butylammonium fluoride in a solvent such as THF.

Sixth Step

The compound (g-8) of the present invention can be obtained from the compound (g-7) by using the method described in the preparation method 1, fifth step, or the like.

(3) Method C (Y is Atomic Bond)

[Formula 13]

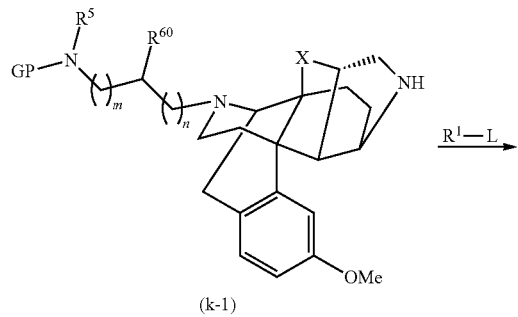

(k-1)

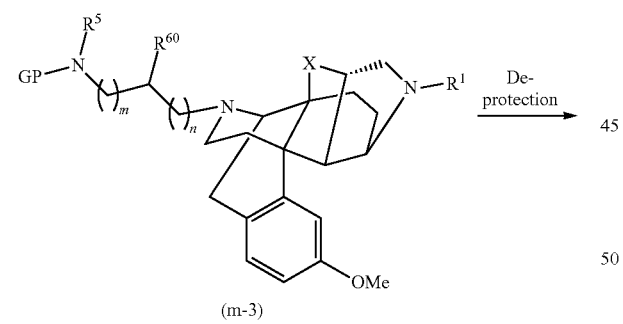

(m-3)

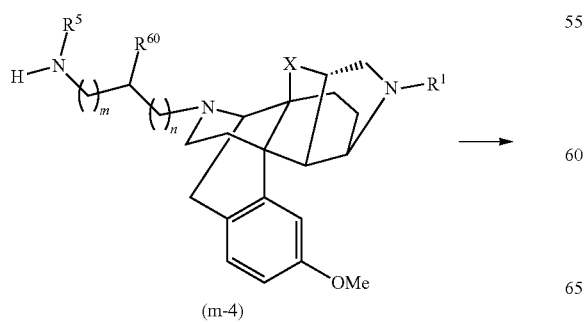

(m-4)

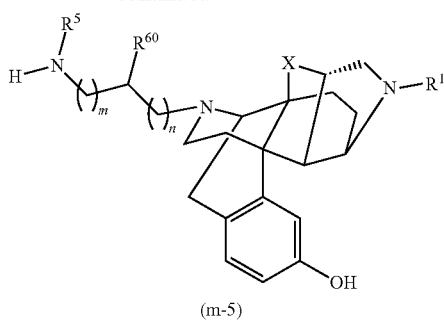

(m-5)

PG: Protective group such as t-butoxycarbonyl group

L: Leaving group such as a halogen atom and p-toluenesulfonyloxy group $R^{60}$: The same as $R^6$ mentioned above provided that hydroxy group is excluded $R^1$, $R^5$, X, m, and n have the same meanings as those defined above.

The steps of the method C are carried out by using the methods already described (for first step, the preparation method 2, fifth step; for second step, preparation method 1, fifth step; and for third step, method A, fourth step).

(4) Method D (Y is C=O, SO$_2$, C(=O)O, C(=O)NR$^7$, or Atomic Bond)

[Formula 14]

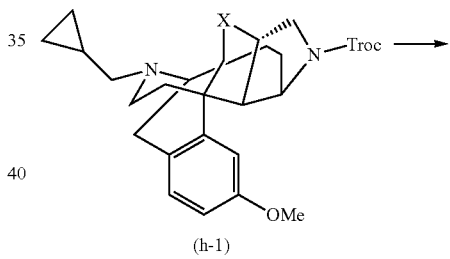

(h-1)

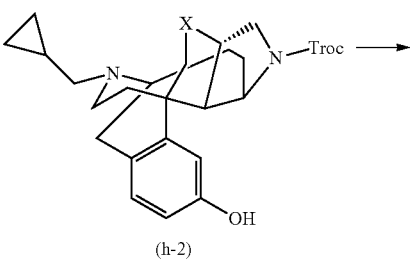

(h-2)

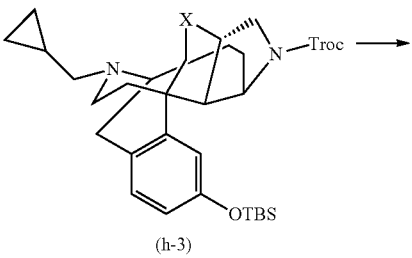

(h-3)

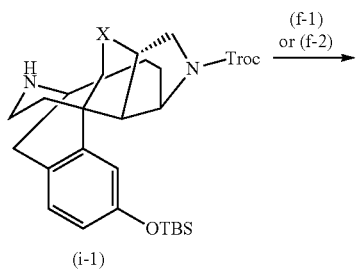

(i-1)

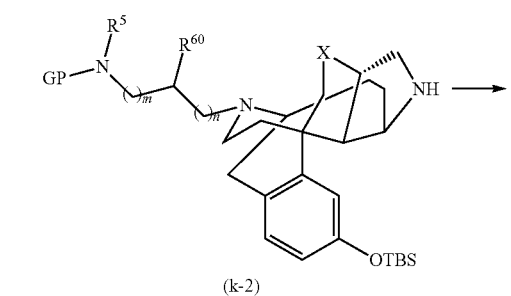

(j-1)

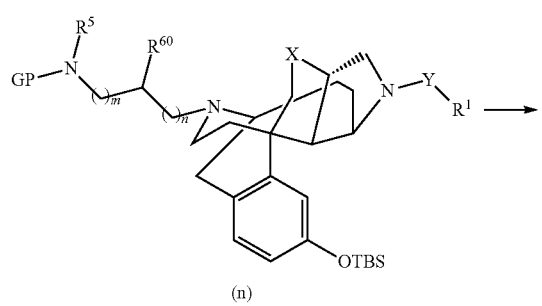

(k-2)

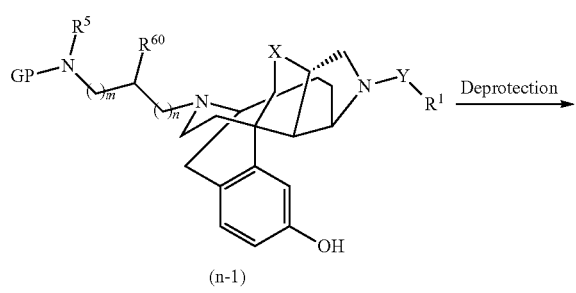

(n)

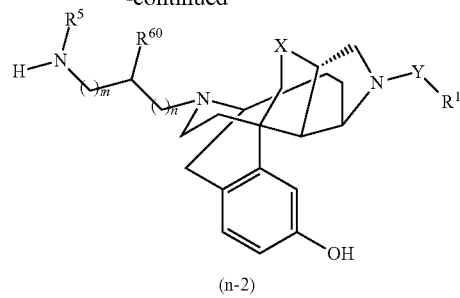

(n-2)

Troc: 2,2,2-Trichloroethoxycarbonyl group
TBS: t-Butyldimethylsilyl group
PG: Protective group such as t-butoxycarbonyl group
$R^{60}$: The same as $R^6$ mentioned above provided that hydroxy group is excluded
$R^1$, $R^5$, X, Y, m, and n have the same meanings as those defined above.

The steps of the method D are performed by a combination of the methods already described (for first step, method A, fourth step; for second step, method B, second step and third step; for third step, preparation method 1, third step; for fourth step, preparation method 1, fourth step; for fifth step, preparation method 2, fourth step; for sixth step, preparation method 1, second step, or preparation method 2, fifth step; for seventh step, method B, fifth step; and for eighth step, preparation method 1, fifth step).

(5) Method E (Y is C=O, SO$_2$, C(=O)O, C(=O N)R$^7$, or atomic bond)

[Formula 15]

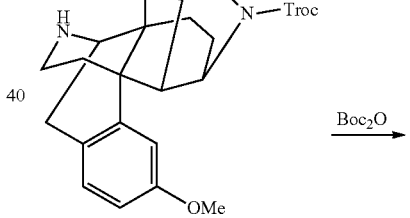

(i-2)

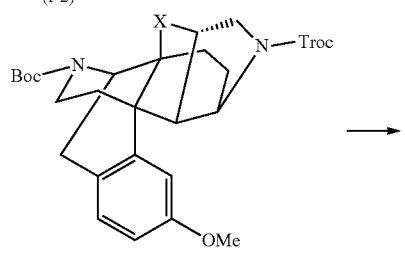

(o)

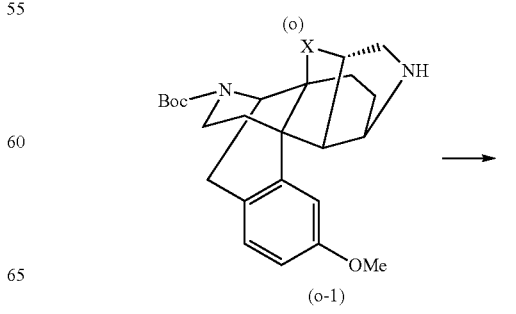

(o-1)

(f-1) or (f-2)

Boc$_2$O (n-1) Deprotection

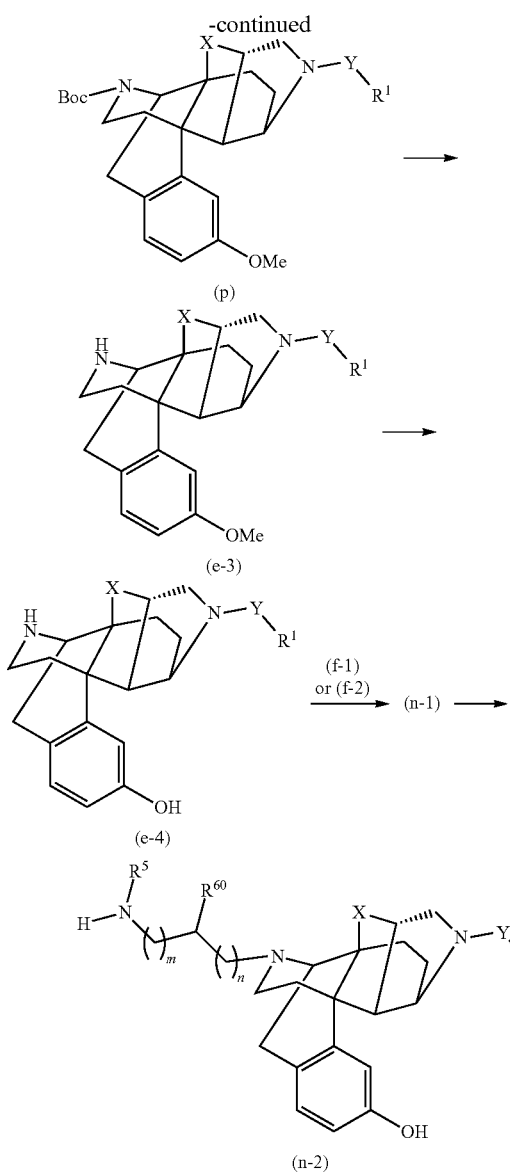

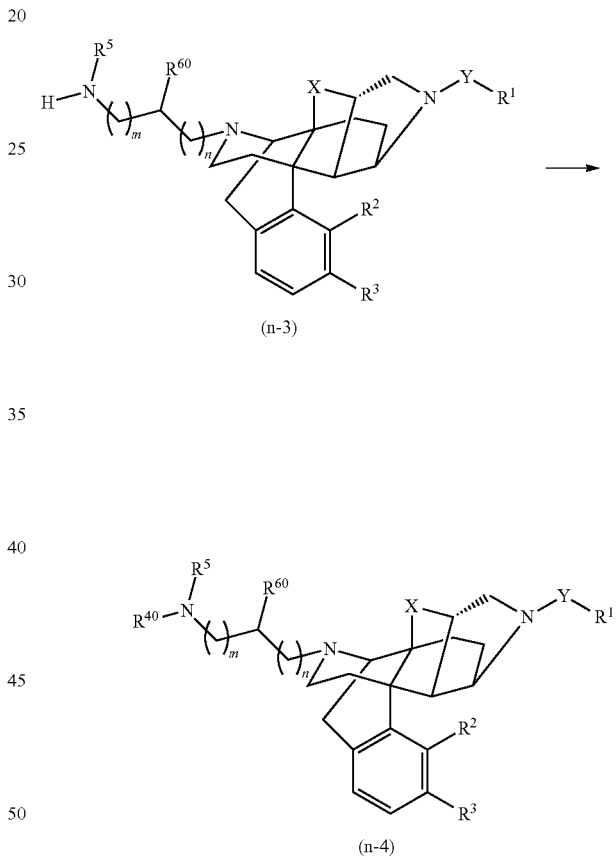

the compound (p). The solvent to be used is appropriately chosen according to the type of the acid, and trifluoroacetic acid may be used as both a reagent and a solvent.

Fifth, Sixth, and Seventh Steps

These steps are performed by the methods of the preparation method 3, method A, fourth step, the preparation method 1, fourth step, and fifth step, respectively.

(Preparation Method 4)

Morphinan Derivative Represented by the Aforementioned General Formula (I), Wherein $R^4$ is the Same as $R^4$ Mentioned Above Provided that Hydrogen is Excluded This compound is synthesized by any of the following methods F to H.

(1) Method F

[Formula 16]

Troc: 2,2,2-Trichloroethoxycarbonyl group
Boc: T-Butoxycarbonyl group
$R^{60}$: The same as $R^6$ mentioned above provided that hydroxy group is excluded
$R^1$, $R^5$, X, Y, m, and n have the same meanings as those defined above.

First Step

The compound (o) can be obtained by reacting the compound (i-2) (synthesized by a combination of the synthesis methods already described) with di-t-butyl dicarbonate in a solvent such as dichloromethane in the presence of a base such as triethylamine.

Second and Third Steps

The compound (o-1) is synthesized by the method described in the preparation method 2, fourth step, and the compound (p) is synthesized by the method described in the preparation method 1, second step, or the preparation method 2, fifth step.

Fourth Step

The compound (e-3) can be obtained by allowing an acid such as trifluoroacetic acid and hydrochloric acid to act on $R^{40}$: The same as $R^4$ mentioned above provided that hydrogen and aryl are excluded
$R^{60}$: The same as $R^6$ mentioned above provided that hydroxy group is excluded
$R^1$, $R^2$, $R^3$, $R^5$, X, Y, m, and n have the same meanings as those defined above.

The compound (n-4) is synthesized by a reductive amination reaction of the compound (n-3) with an aldehyde or ketone. As the reducing agent used for the reaction, sodium triacetoxyborohydride, sodium cyanoborohydride, and the like are used, and the compound (n-3) as the starting material is synthesized by a combination of the synthesis methods already described.

(2) Method G

[Formula 17]

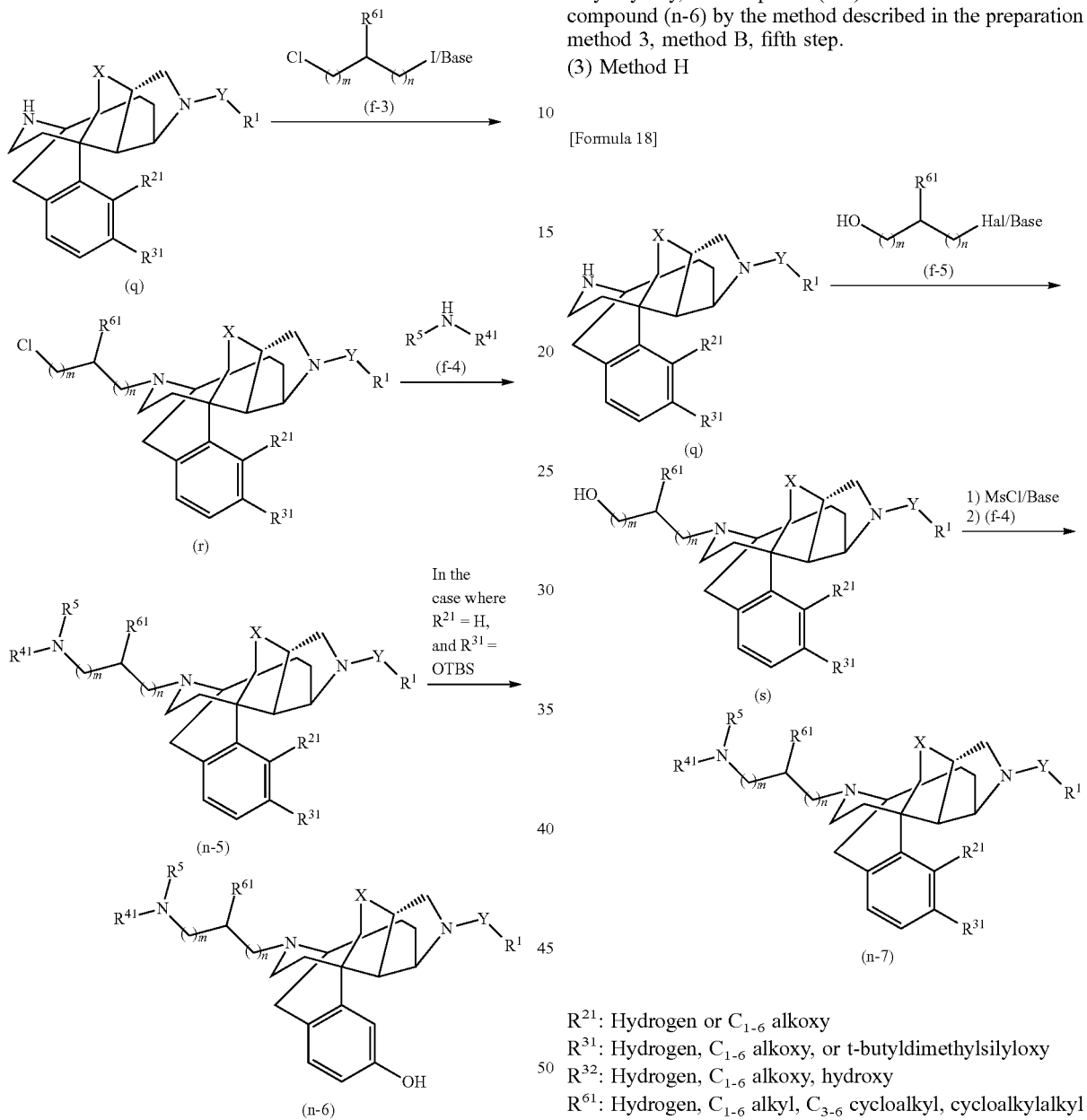

R$^{21}$: Hydrogen or C$_{1-6}$ alkoxy
R$^{31}$: Hydrogen, C$_{1-6}$ alkoxy, or t-butyldimethylsilyloxy
R$^{61}$: Hydrogen, C$_{1-6}$ alkyl, C$_{3-6}$ cycloalkyl, cycloalkylalkyl (the cycloalkyl moiety has 3 to 6 carbon atoms, and the alkylene moiety has 1 to 5 carbon atoms), or C$_{6-10}$ aryl
OTBS: t-Butyldimethylsilyloxy
R$^{41}$: The same as R$^4$ mentioned above provided that hydrogen is excluded
R$^1$, R$^5$, X, Y, m, and n have the same meanings as those defined above.

The compound (n-5) of the present invention can be obtained by an N-alkylation reaction of the compound (q) (synthesized by a combination of the synthesis methods already described) with a dihalogenated compound (f-3), and a reaction of the resulting compound (r) with an amine (f-4). Further, when R$^{21}$ is hydrogen, and R$^{31}$ is t-butyldimethylsilyloxy, the compound (n-5) can be converted into the compound (n-6) by the method described in the preparation method 3, method B, fifth step.

(3) Method H

[Formula 18]

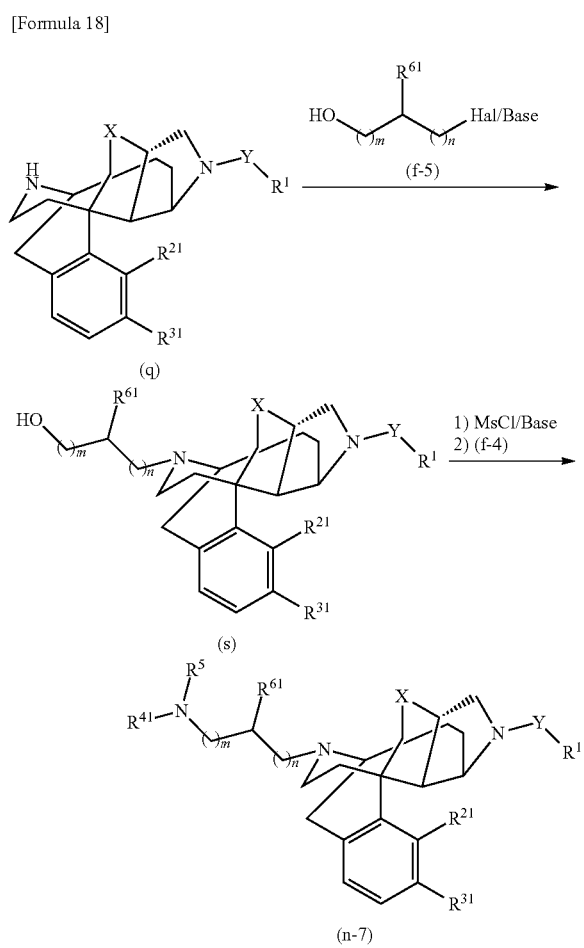

R$^{21}$: Hydrogen or C$_{1-6}$ alkoxy
R$^{31}$: Hydrogen, C$_{1-6}$ alkoxy, or t-butyldimethylsilyloxy
R$^{32}$: Hydrogen, C$_{1-6}$ alkoxy, hydroxy
R$^{61}$: Hydrogen, C$_{1-6}$ alkyl, C$_{3-6}$ cycloalkyl, cycloalkylalkyl (the cycloalkyl moiety has 3 to 6 carbon atoms, and the alkylene moiety has 1 to 5 carbon atoms), or C$_{6-10}$ aryl
Hal: Halogen atom
MsCl: Methanesulfonyl chloride
R$^{41}$: The same as R$^4$ mentioned above provided that hydrogen is excluded
R$^1$, R$^5$, X, Y, m, and n have the same meanings as those defined above.

First Step

The compound (s) can be obtained by a reaction of the compound (q) and a haloalcohol (f-5) in a solvent such as acetonitrile in the presence of a base such as potassium carbonate.

Second Step

The compound (n-7) can be obtained by methanesulfonylating the hydroxy group of the compound (s), and then reacting the resulting product with an amine (f-4). In this step, when $R^{31}$ of the compound (s) is t-butyldimethylsilyloxy, de-t-butyldimethylsilylation simultaneously advances, and the compound (n-7) in which $R^{32}$ is converted into hydroxy group is obtained.

(Preparation Method 5)

Morphinan Derivative Represented by the Aforementioned General Formula (I), Wherein $R^4$ is Hydrogen, $R^6$ is Hydroxy, and n is 1

[Formula 19]

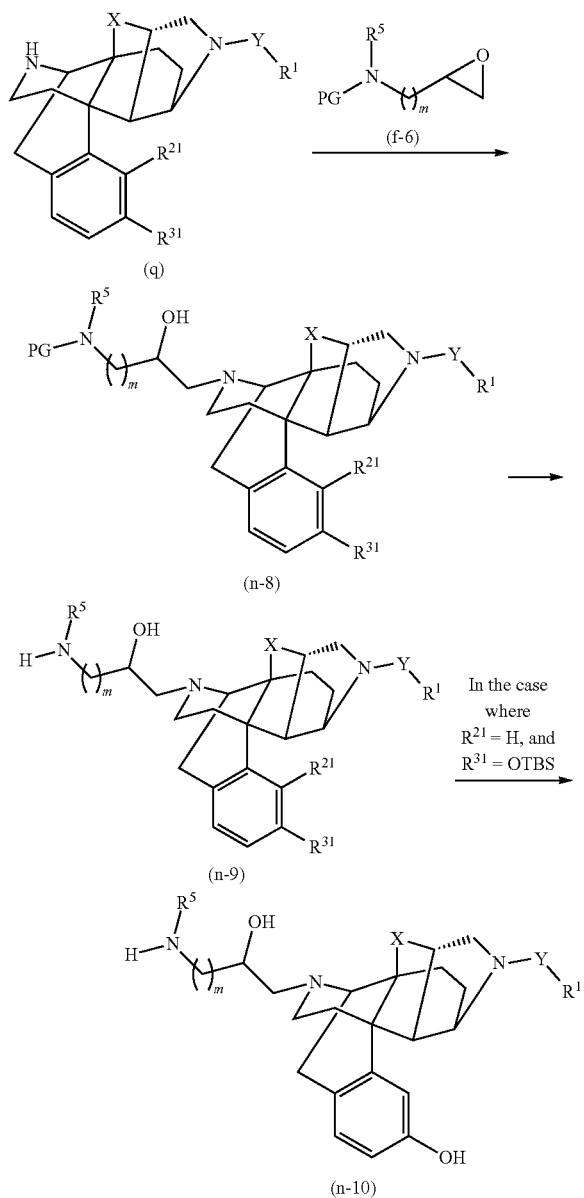

$R^{21}$: Hydrogen, or $C_{1-6}$ alkoxy
$R^{31}$: Hydrogen, $C_{1-6}$ alkoxy, or t-butyldimethylsilyloxy
PG: Protective group such as t-butoxycarbonyl group
OTBS: t-Butyldimethylsilyloxy $R^1$, $R^5$, X, Y, m have the same meanings as those defined above.

First Step

The compound (n-8) can be obtained by a reaction of the compound (q) and an epoxide (f-6) in a solvent such as methanol.

Second and Third Steps

The protective group PG of the compound (n-8) is eliminated by the method described in the preparation method 1, fifth step, or the like, and the compound (n-9) is converted into the compound (n-10) by the method described in the preparation method 3, method B, fifth step.

Other compounds of the general formula (I) can be prepared by a combination of the aforementioned synthesis methods, and the methods described in the examples mentioned later, or the like.

The compound of the aforementioned general formula (I), wherein —CH($R^6$)— is cyclopropene-1,1-diyl is described in Example 16, and the compounds of the aforementioned general formula (I), wherein —CH($R^6$)— is cyclopropene-1,1-diyl, and $R^1$ to $R^5$, m, n, X, and Y have the same meanings as those defined above also fall within the scope of the present invention.

Hereafter, the results of pharmacological experiments will be described.

As shown in Example 37, Table 5 mentioned later, it was revealed that the morphinan derivatives represented by the aforementioned general formula (I), tautomers and stereoisomers of the compounds, pharmaceutically acceptable salts thereof, and solvates thereof had outstanding δ receptor agonistic action in the opioid receptor function test.

Further, as shown in Example 38, Table 6 mentioned later, it was revealed that the morphinan derivatives represented by the following general formula (I), tautomers and stereoisomers of the compounds, pharmaceutically acceptable salts thereof, and solvates thereof showed selective affinity to the opioid δ receptor in the opioid receptor binding test.

Furthermore, as shown in Example 39, Table 7 mentioned later, it was revealed that the morphinan derivatives represented by the following general formula (I), tautomers and stereoisomers of the compounds, pharmaceutically acceptable salts thereof, and solvates thereof showed only weak inhibitory action in the hERG (human ether-a-go-go-related gene) potassium channel inhibition test. This result suggests that the morphinan derivatives represented by the aforementioned general formula (I), tautomers and stereoisomers of the compounds, pharmaceutically acceptable salts thereof, and solvates thereof impose low risks for retarding ventricle repolarization and prolongation of the QT interval in humans.

In addition, in the metabolism stability test using mouse hepatic microsomes, it was revealed that the compounds of the present invention had superior stability.

Therefore, the morphinan derivatives represented by the aforementioned general formula (I), tautomers and stereoisomers of the compounds, pharmaceutically acceptable salts thereof, and solvates thereof can be used for therapeutic treatments of pains in diseases accompanied by an acute pain or chronic pain, or as prophylactic and therapeutic agents for pains of rheumatoid arthritis, osteoarthritis deformans, cancer pain accompanied by severe pain such as osteoncus, diabetic neuropathic pain, postherpetic neuralgia, visceral pains, and the like.

Further, the morphinan derivatives represented by the aforementioned general formula (I), tautomers and stereoisomers of the compounds, pharmaceutically acceptable salts thereof, and solvates thereof can be used as therapeutic agents for neurological diseases accompanied by anxiety such as depression, panic disorders, anxiety disorders, and stress disorders (PTSD, acute stress disorder), and as prophylactic and therapeutic agents for urinary incontinence, myocardial ischemia, hypertension, Parkinson's disease, and other motor dysfunctions.

The morphinan derivatives represented by the aforementioned general formula (I), tautomers and stereoisomers of the compounds, pharmaceutically acceptable salts thereof, and solvates thereof can be administered to a human by an appropriate administration method such as oral administration or parenteral administration. Further, they can also be used together with other analgesics.

Pharmaceutical preparations thereof can be prepared in a dosage form of tablet, granule, powder, capsule, suspension, injection, suppository or the like by methods common in the field of pharmaceuticals.

For preparation of pharmaceutical preparations, for example, in the case of tablet, ordinary excipients, disintegrating agents, binders, lubricants, dyes, and the like are used. Examples of the excipients include lactose, D-mannitol, crystalline cellulose, glucose, and the like. Examples of the disintegrating agents include starch, carboxymethylcellulose calcium (CMC-Ca), and the like. Examples of the lubricants include magnesium stearate, talc, and the like. Examples of the binders include hydroxypropylcellulose (HPC), gelatin, polyvinylpyrrolidone (PVP), and the like. For the preparation of injection, solvents, stabilizers, dissolving aids, suspending agents, emulsifiers, soothing agents, buffering agents, preservatives, and the like are used.

As for the dose of the morphinan derivatives represented by the aforementioned general formula (I), tautomers and stereoisomers of the compounds, pharmaceutically acceptable salts thereof, and solvates thereof as active ingredient, they are usually administered to an adult at a dose of 0.1 μg to 1 g/day, preferably 0.001 to 200 mg/day, in the case of injection, or at a dose of 1 μg to 10 g/day, preferably 0.01 to 2000 mg/day, in the case of oral administration, but the dose may be reduced or increased depending on age, symptoms, and the like.

Hereafter, the present invention will be further explained in more detail with reference to reference examples and examples of the present invention. However, the present invention is not limited to these examples.

Reference Example 1

Synthesis of (1S,3aR,5aS,6R,11bR,11cS)-3-benzyl-14-(cyclopropylmethyl)-10-methoxy-2,3,3a,4,5,6,7,11c-octahydro-1H-6,11b-(epiminoethano)-1,5a-epoxynaphtho[1,2-e]indol-11-ol (1)

[Formula 20]

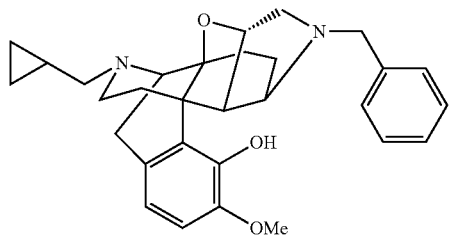

1

Under an argon atmosphere, (1S,3aS,5aS,6R,11bR,11cR)-3-benzyl-14-(cyclopropylmethyl)-3a, 11-dihydroxy-10-methoxy-1,3,3a,4,5,6,7,11c-octahydro-2H-6,11b-(iminoethano)-1,5a-epoxynaphtho[1,2-e]indol-2-one [Compound 4 described in WO2012/102360](10.1 g, 20 mmol) was dissolved in THF (100 mL), the solution was added with a solution of borane-THF complex in THF (1.0 mol/L, 100 mL, 100 mmol), and the mixture was refluxed for 2 hours. The reaction mixture was concentrated under reduced pressure, the residue was added with 6 M hydrochloric acid (200 mL), and the mixture was refluxed for 1 hour. The reaction mixture was cooled to room temperature, then adjusted to pH 11 with potassium carbonate, and extracted three times with chloroform. The organic layers were combined, dried over anhydrous sodium sulfate, and concentrated. The resulting crude product was purified by silica gel column chromatography to give the title compound 1 as white amorphous (8.84 g, 94%).

$^1$H NMR (CDCl$_3$, 400 MHz): δ 0.02-0.16 (m, 2H), 0.42-0.70 (m, 3H), 0.90-1.02 (m, 1H), 1.37-1.47 (m, 1H), 1.51 (dd, J=7.6, 14.8 Hz, 1H), 1.66-1.89 (m, 2H), 1.97-2.12 (m, 2H), 2.22 (dd, J=7.2, 12.8 Hz, 1H), 2.55 (dd, J=5.6, 12.8, 1H), 2.56-2.68 (m, 1H), 2.81-2.93 (m, 2H), 3.05 (d, J=18.4 Hz, 1H), 3.31 (dd, J=6.8, 10.8 Hz, 1H), 3.46-3.59 (m, 2H), 3.60 (d, J=6.4 Hz, 1H), 3.74 (d, J=13.6 Hz, 1H), 3.75 (d, J=13.6 Hz, 1H), 3.79 (s, 3H), 4.91-4.98 (m, 1H), 6.25 (br s, 1H), 6.60 (d, J=8.4 Hz, 1H), 6.64 (d, J=8.4 Hz, 1H), 7.11-7.31 (m, 5H)

Reference Example 2

Synthesis of (1S,3aR,5aS,6R,11bR,11cS)-3-benzyl-14-(cyclopropylmethyl)-10-methoxy-11-phenoxy-2,3,3a,4,5,6,7,11c-octahydro-1H-6,11b-(epiminoethano)-1,5a-epoxynaphtho[1,2-e]indole (2)

[Formula 21]

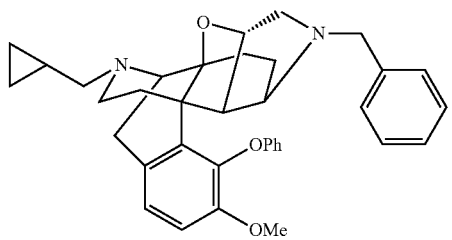

2

Under an argon atmosphere, the compound 1 (8.84 g, 19 mmol) was dissolved in pyridine (100 mL), the solution was added with bromobenzene (98.5 mL, 94 mmol), potassium carbonate (7.76 g, 56 mmol), and copper powder (1.19 g, 19 mmol), and the mixture was refluxed for 16 hours. The reaction mixture was further added with bromobenzene (4.92 g, 47 mmol), potassium carbonate (7.76 g, 56 mmol), and copper powder (1.19 g, 19 mmol), and the mixture was further refluxed for 24 hours. The reaction mixture was cooled to room temperature, and then filtered through Celite, the filtrate was poured into water, and the mixture was extracted three times with chloroform. The organic layers were combined, dried over anhydrous sodium sulfate, and then concentrated. The resulting crude product was purified by silica gel column chromatography to give the title compound 2 as black oil (10.1 g, 98%).

¹H NMR (CDCl₃, 300 MHz): δ 0.00-0.16 (m, 2H), 0.40-0.78 (m, 3H), 0.86-1.02 (m, 1H), 1.04-1.14 (m, 1H), 1.41-1.53 (m, 1H), 1.68-1.93 (m, 3H), 2.06 (dt, J=3.0, 12.3 Hz, 1H), 2.23 (dd, J=7.2, 12.3 Hz, 1H), 2.49-2.61 (m, 2H), 2.83-2.99 (m, 1H), 2.86 (dd, J=2.4, 10.8 Hz, 1H), 3.11 (d, J=18.6 Hz, 1H), 3.15 (dd, J=6.3, 11.1 Hz, 1H), 3.22 (dd, J=6.0, 7.5 Hz, 1H), 3.53-3.63 (m, 2H), 3.66 (d, J=13.5 Hz, 1H), 3.67 (s, 3H), 3.75 (d, J=13.5 Hz, 1H), 4.77-4.86 (m, 1H), 6.76 (d, J=7.8 Hz, 2H), 6.80 (d, J=8.4 Hz, 1H), 6.96 (t, J=7.2 Hz, 1H), 6.99 (d, J=8.1 Hz, 1H), 7.16-7.32 (m, 7H)

Reference Example 3

Synthesis of (1S,3aR,5aS,6R,11bR,11cS)-3-benzyl-14-(cyclopropylmethyl)-10-methoxy-2,3, 3a,4,5,6,7,11c-octahydro-1H-6,11b-(epiminoethano)-1,5a-epoxynaphtho[1,2-e]indole (3)

[Formula 22]

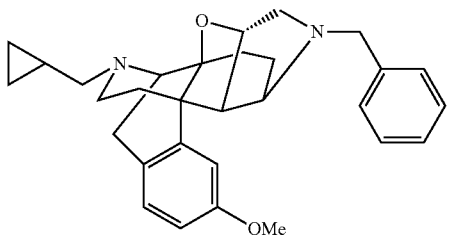

3

Under an argon atmosphere, the compound 2 (91 mg, 0.17 mmol) was dissolved in THF (2 mL), the solution was added with ethylenediamine (333 μL, 6.2 mmol), the mixture was added with Sodium silica gel Stage I five times every 1 hour (900 mg in total). The reaction mixture was stirred at room temperature for 5 hours, and then poured into water under ice cooling, and the mixture was extracted three times with ethyl acetate. The organic layers were combined, washed with saturated brine, dried over anhydrous sodium sulfate, and concentrated. The resulting crude product was purified by silica gel column chromatography to give the title compound 3 as colorless oil (68 mg, 90%).

¹H NMR (CDCl₃, 300 MHz): δ 0.00-0.16 (m, 2H), 0.41-0.59 (m, 3H), 0.87-1.03 (m, 1H), 1.13-1.30 (m, 1H), 1.51 (dd, J=6.9, 15.0 Hz, 1H), 1.62-1.84 (m, 2H), 2.00-2.16 (m, 2H), 2.23 (dd, J=7.2, 12.3 Hz, 1H), 2.54-2.67 (m, 1H), 2.55 (dd, J=5.4, 12.6 Hz, 1H), 2.73-2.87 (m, 2H), 2.97-3.07 (m, 1H), 3.07 (d, J=18.6 Hz, 1H), 3.30 (dd, J=6.9, 10.8 Hz, 1H), 3.47 (t, J=6.6 Hz, 1H), 3.62 (d, J=6.9 Hz, 1H), 3.66 (d, J=13.5 Hz, 1H), 3.75 (s, 3H), 3.78 (d, J=13.5 Hz, 1H), 4.93-5.02 (m, 1H), 6.66-6.74 (m, 2H), 6.88-7.07 (m, 1H), 7.17-7.34 (m, 5H)

Reference Example 4

Synthesis of (1S,3aR,5aS,6R,11bR,11cS)-14-(cyclopropylmethyl)-10-methoxy-2,3,3a,4,5,6,7,11c-octahydro-1H-6,11b-(epiminoethano)-1,5a-epoxynaphtho[1,2-e]indole (4)

[Formula 23]

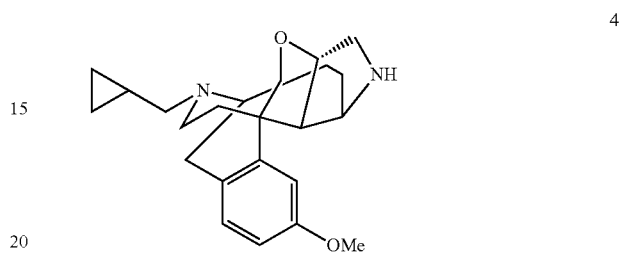

4

The compound 3 (1.83 g, 4.0 mmol) was dissolved in ethanol (20 mL), the solution was added with 10% palladium/carbon (1.12 g), and the mixture was stirred at 40° C. for 15 hours under a hydrogen atmosphere. The reaction mixture was filtered through Celite, and then the filtrate was concentrated. The resulting crude product was purified by silica gel column chromatography to give the title compound 4 as yellow oil (1.27 g, 86%).

¹H NMR (CDCl₃, 300 MHz): δ 0.02-0.16 (m, 2H), 0.42-0.60 (m, 2H), 0.80-1.11 (m, 3H), 1.20-1.35 (m, 1H), 1.76 (dd, J=4.8, 10.8 Hz, 2H), 1.96 (br s, 1H), 2.00-2.20 (m, 2H), 2.25 (dd, J=7.2, 12.3 Hz, 1H), 2.55-2.70 (m, 1H), 2.56 (dd, J=5.4, 12.3 Hz, 1H), 2.74-2.93 (m, 2H), 3.08 (d, J=18.3 Hz, 1H), 3.22 (dd, J=2.4, 12.6 Hz, 1H), 3.38 (dd, J=6.3, 12.6 Hz, 1H), 3.56-3.68 (m, 2H), 3.79 (s, 3H), 4.97 (dt, J=2.1, 6.3 Hz, 1H), 6.66-6.77 (m, 2H), 6.99-7.08 (m, 1H)

Reference Example 5

Synthesis of (1S,3aR,5aS,6R,11bR,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indol-11-ol (5)

[Formula 24]

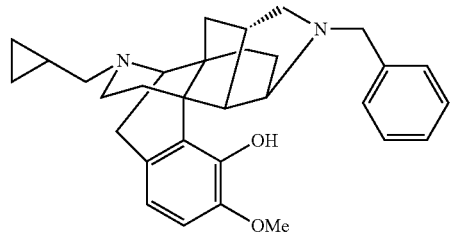

5

According to the method described in Reference Example 1, the title compound 5 was obtained by using (1S,3aS,5aS,6R,11bS,11cS)-3-benzyl-14-(cyclopropylmethyl)-3a, 11-dihydroxy-10-methoxy-1,3,3a,4,5,6,7,11c-octahydro-2H-6,11b-(iminoethano)-1,5a-methanonaphtho[1,2-e]indol-2-one [Compound 38 described in WO2012/102360].

¹H NMR (CDCl₃, 400 MHz): δ 0.03-0.14 (m, 2H), 0.40-0.50 (m, 2H), 0.66-0.86 (m, 2H), 1.08-1.15 (m, 1H), 1.20-1.35 (m, 2H), 1.49-1.75 (m, 3H), 1.84-2.05 (m, 2H), 2.30 (d, J=5.9 Hz, 2H), 2.49-2.59 (m, 1H), 2.60-2.70 (m, 1H), 2.87-3.00 (m, 3H), 3.01-3.15 (m, 2H), 3.20-3.31 (m, 1H), 3.32-3.45 (m, 1H), 3.60-3.80 (m, 2H), 3.84 (s, 3H), 5.63 (br s, 1H), 6.61 (d, J=8.3 Hz, 1H), 6.63 (d, J=8.3 Hz, 1H), 7.16-7.40 (m, 5H)

Reference Example 6

Synthesis of (1S,3aR,5aS,6R,11bR,11cS)-3-benzyl-14-(cyclopropylmethyl)-10-methoxy-11-phenoxy-2,3,3a,4,5,6,7,11c-octahydro-1H-6,11b-(epiminoethano)-1,5a-methanonaphtho[1,2-e]indole (6)

[Formula 25]

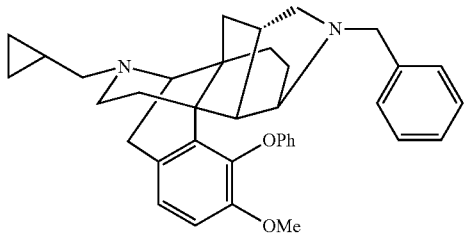

6

According to the method described in Reference Example 2, the title compound 6 was obtained by using the compound 5.

¹H NMR (CDCl₃, 400 MHz): δ 0.03-0.15 (m, 2H), 0.40-0.51 (m, 2H), 0.70-0.85 (m, 2H), 0.96-1.11 (m, 2H), 1.12-1.25 (m, 1H), 1.55-1.78 (m, 3H), 1.99 (dt, J=3.4, 12.2 Hz, 1H), 2.29 (d, J=5.9 Hz, 2H), 2.46 (dd, J=3.9, 11.2 Hz, 1H), 2.58-2.80 (m, 3H), 2.90-3.24 (m, 6H), 3.55-3.75 (m, 2H), 3.67 (s, 3H), 6.73-6.85 (m, 3H), 6.95 (d, J=8.3 Hz, 1H), 6.99 (d, J=8.3 Hz, 1H), 7.15-7.34 (m, 7H)

Reference Example 7

Synthesis of (1S,3aR,5aS,6R,11bR,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indole (7)

[Formula 26]

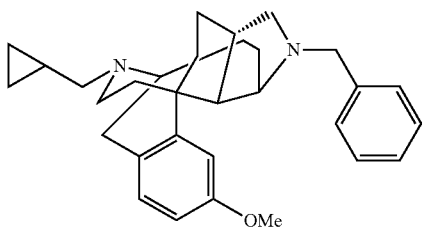

7

According to the method described in Reference Example 3, the title compound 7 was obtained by using the compound 6.

¹H NMR (CDCl₃, 400 MHz): δ 0.04-0.15 (m, 2H), 0.40-0.52 (m, 2H), 0.57-0.70 (m, 1H), 0.75-0.85 (m, 1H), 1.05-1.19 (m, 2H), 1.23-1.33 (m, 1H), 1.46-1.71 (m, 3H), 1.92-2.04 (m, 2H), 2.25-2.40 (m, 2H), 2.50-2.65 (m, 2H), 2.81-3.05 (m, 4H), 3.06-3.18 (m, 2H), 3.22-3.30 (m, 1H), 3.66 (d, J=13.7 Hz, 1H), 3.73 (d, J=13.7 Hz, 1H), 3.75 (s, 3H), 6.65 (dd, J=2.9, 8.3 Hz, 1H), 6.69 (d, J=2.9 Hz, 1H), 7.01 (d, J=8.3 Hz, 1H), 7.18-7.34 (m, 5H)

Reference Example 8

Synthesis of (1S,3aR,5aS,6R,11bR,11cS)-14-(cyclopropylmethyl)-10-methoxy-2,3,3a,4,5,6,7,11c-octahydro-1H-6,11b-(epiminoethano)-1,5a-methanonaphtho[1,2-e]indole (8)

[Formula 27]

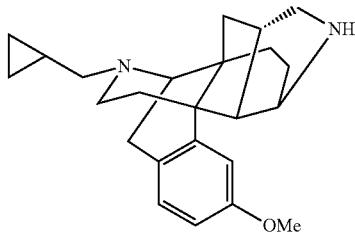

8

According to the method described in Reference Example 4, the title compound 8 was obtained from the compound 7.

¹H NMR (CDCl₃, 400 MHz): δ 0.06-0.14 (m, 2H), 0.44-0.52 (m, 2H), 0.75-0.86 (m, 1H), 0.98-1.10 (m, 3H), 1.15 (d, J=8.8 Hz, 1H), 1.34-1.45 (m, 1H), 1.60-1.72 (m, 1H), 1.86-2.06 (m, 3H), 2.26-2.36 (m, 2H), 2.52-2.60 (m, 1H), 2.70-2.76 (m, 1H), 2.78-3.00 (m, 4H), 3.08 (d, J=5.9 Hz, 1H), 3.10-3.25 (m, 1H), 3.30 (dd, J=7.8, 11.2 Hz, 1H), 3.50-3.58 (m, 1H), 3.77 (s, 3H), 6.66 (dd, J=2.4, 8.3 Hz, 1H), 6.73 (d, J=2.4 Hz, 1H), 7.02 (d, J=8.3 Hz, 1H)

Example 1

Synthesis of [(1S,3aR,5aS,6R,11bR,11cS)-14-(2-aminoethyl)-10-methoxy-1,2,3a,4,5,6,7,11c-octahydro-3H-6,11b-(epiminoethano)-1,5a-methanonaphtho[1,2-e]indol-3-yl](phenyl)methanone (12)

(1) [(1S,3aR,5aS,6R,11bR,11cS)-14-(Cyclopropylmethyl)-10-methoxy-1,2,3a,4,5,6,7,11c-octahydro-3H-6,11b-(epiminoethano)-1,5a-methanonaphtho[1,2-e]indol-3-yl](phenyl)methanone

[Formula 28]

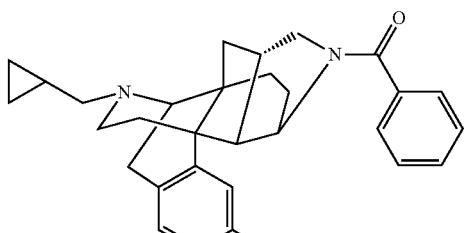

9

Under an argon atmosphere, the compound 8 (300 mg, 0.82 mmol) was dissolved in dichloromethane (8 mL), the solution was added with benzoyl chloride (143 μL, 1.23 mmol) and triethylamine (343 μL, 2.46 mmol), and the mixture was stirred at room temperature for 16 hours. The reaction mixture was poured into saturated aqueous sodium hydrogencarbonate, and the mixture was extracted three times with chloroform. The organic layers were combined, dried over anhydrous sodium sulfate, and concentrated. The resulting crude product was purified by silica gel column chromatography to give the title compound 9 (384 mg, 100%).

(2) [(1S,3aR,5aS,6R,11bR,11cS)-10-Methoxy-1,2,3a,4,5,6,7,11c-octahydro-3H-6,11b-(epiminoethano)-1,5a-methanonaphtho[1,2-e]indol-3-yl](phenyl)methanone

[Formula 29]

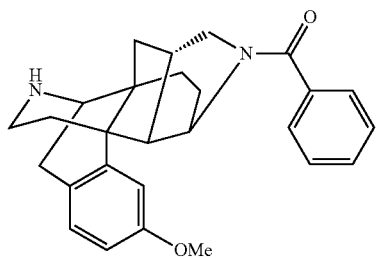

Under an argon atmosphere, the compound 9 (30.0 mg, 0.064 mmol) was dissolved in benzene (2.0 mL), the solution was added with a 2.2 mol/L solution of diethyl azodicarboxylate in toluene (118.0 DL), and the mixture was refluxed for 5 hours by heating. The reaction mixture was left to cool, and then concentrated under reduced pressure, the residue was added with ethanol (2.0 mL) and pyridine hydrochloride (50.0 mg), and the mixture was stirred at room temperature for 17 hours. The reaction mixture was concentrated under reduced pressure, and then the residue was made acidic by adding 2 M hydrochloric acid, and washed three times with diethyl ether. The aqueous layer was made basic with 6% aqueous ammonia, and extracted three times with chloroform. The extract was dried over anhydrous sodium sulfate, and then concentrated under reduced pressure. The resulting crude product was purified by preparative TLC to give the title compound 10 as brown amorphous (14.4 mg, 54%).

$^1$H NMR (CDCl$_3$, 400 MHz): δ 0.75-1.05 (m, 0.7H), 1.06-1.18 (m, 1H), 1.20-1.35 (m, 1H), 1.40-1.70 (m, 2H), 1.70-1.95 (m, 2H), 1.86 (br s, 1H), 2.58-2.76 (m, 2H), 2.80-3.08 (m, 4H), 3.10-3.23 (m, 1.3H), 3.35-3.60 (m, 1.7H), 3.65-3.70 (m, 1H), 3.68 (s, 0.9H), 3.78 (s, 2.1H), 4.17 (t, J=6.3 Hz, 0.3H), 4.28 (dd, J=9.3, 12.7 Hz, 0.3H), 4.80 (t, J=6.3 Hz, 0.7H), 6.53 (d, J=2.0 Hz, 0.3H), 6.64 (dd, J=2.0, 8.3 Hz, 0.3H), 6.70-6.78 (m, 1.4H), 7.01 (d, J=8.3 Hz, 0.3H), 7.06 (d, J=8.3 Hz, 0.7H), 7.31-7.47 (m, 5H)

(3) t-Butyl[2-[(1S,3aR,5aS,6R,11bR,11cS)-3-benzoyl-10-methoxy-2,3,3a,4,5,6,7,11c-octahydro-1H-6,11b-(epiminoethano)-1,5a-methanonaphtho[1,2-e]indol-14-yl]ethyl]carbamate

[Formula 30]

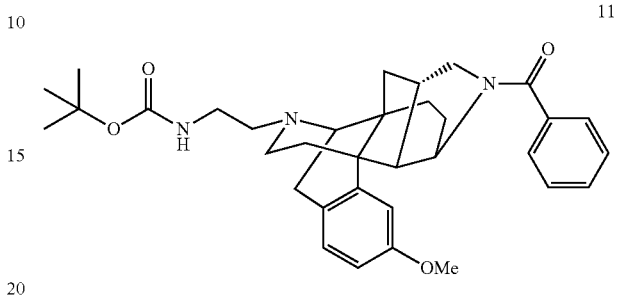

Under an argon atmosphere, the compound 10 (50 mg, 0.12 mmol) was dissolved in acetonitrile (1 mL), the solution was added with 2-(Boc-amino)ethyl bromide (40 mg, 0.18 mmol), potassium carbonate (66 mg, 0.48 mmol), and sodium iodide (54 mg, 0.36 mmol), and the mixture was stirred at 70° C. for 16 hours. The reaction mixture was cooled to room temperature, then diluted with ethyl acetate, and washed with water and saturated brine. The organic layer was dried over anhydrous sodium sulfate, and then concentrated. The resulting crude product was purified by silica gel column chromatography to give the title compound 11 (67 mg, 100%).

$^1$H NMR (CDCl$_3$, 400 MHz): δ 0.75-2.25 (m, 7H), 1.60 (s, 9H), 2.20-2.50 (m, 3H), 2.70-2.85 (m, 2H), 2.85-3.20 (m, 6H), 3.20-3.40 (m, 1H), 3.40-4.00 (m, 2H), 3.69 (s, 0.9H), 3.79 (s, 2.1H), 4.10-4.35 (m, 1H), 4.75-4.85 (m, 1H), 6.51 (d, J=2.4 Hz, 0.3H), 6.63 (dd, J=2.4, 8.3 Hz, 0.3H), 6.67-6.74 (m, 1.4H), 6.99 (d, J=8.3 Hz, 0.3H), 7.05 (d, J=8.3 Hz, 0.7H), 7.20-7.60 (m, 5H)

(4) [(1S,3aR,5aS,6R,11bR,11cS)-14-(2-Aminoethyl)-10-methoxy-1,2,3a,4,5,6,7,11c-octahydro-3H-6,11b-(epiminoethano)-1,5a-methanonaphtho[1,2-e]indol-3-yl](phenyl)methanone

[Formula 31]

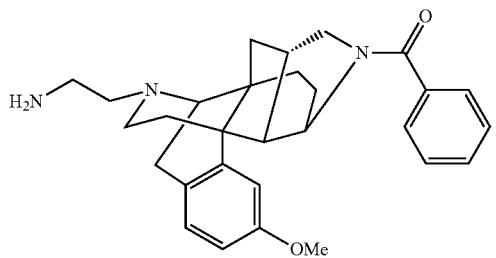

Under an argon atmosphere, the compound 11 (67 mg, 0.12 mmol) was dissolved in dichloromethane (0.5 mL), the solution was added with trifluoroacetic acid (0.5 mL), and the mixture was stirred at room temperature for 16 hours. The reaction mixture was concentrated, and the residue was dissolved in ethyl acetate. The organic layer was washed with aqueous potassium carbonate, water, and saturated brine, dried over anhydrous sodium sulfate, and then concentrated. The resulting crude product was purified by silica gel column chromatography to give the title compound 12 (45 mg, 82%).

Compound 12 (free base) $^1$H NMR (CDCl$_3$, 400 MHz): δ 0.75-2.00 (m, 6H), 2.00-2.25 (m, 1H), 2.35-2.60 (m, 3H), 2.65-2.80 (m, 3H), 2.80-3.20 (m, 6H), 3.25-3.40 (m, 1H), 3.50-4.00 (m, 3H), 3.69 (s, 0.9H), 3.79 (s, 2.1H), 4.10-4.30 (m, 1H), 4.75-4.90 (m, 1H), 6.52 (d, J=2.4 Hz, 0.3H), 6.63 (dd, J=2.4, 8.3 Hz, 0.3H), 6.65-6.80 (m, 1.4H), 7.20-7.50 (m, 5H)

Example 2

Synthesis of [(1S,3aR,5aS,6R,11bR,11cS)-14-(2-aminoethyl)-10-hydroxy-1,2,3a,4,5,6,7,11c-octahydro-3H-6,11b-(epiminoethano)-1,5a-methanonaphtho[1,2-e]indol-3-yl](phenyl)methanone (13)

[Formula 32]

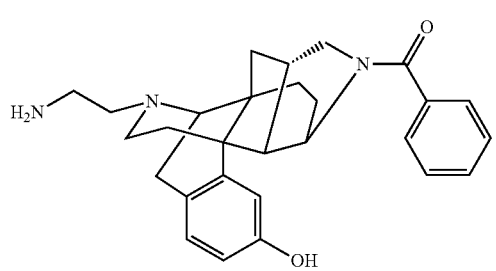

Under an argon atmosphere, the compound 12 (45 mg, 0.098 mmol) was dissolved in dichloromethane (1 mL), the solution was added with a solution of boron tribromide in dichloromethane (1.0 mol/L, 0.49 mL, 0.49 mmol) under ice cooling, and the mixture was stirred at room temperature for 2 hours. The reaction mixture was added with 6% aqueous ammonia (3 mL) under ice cooling, and the mixture was stirred at room temperature for 30 minutes. The mixture was added with water, and the resulting mixture was extracted three times with chloroform. The organic layers were combined, dried over anhydrous sodium sulfate, and then concentrated. The resulting crude product was purified by preparative TLC to give the title compound 13. The resulting compound 13 was treated with a 20% solution of hydrogen chloride in methanol to give hydrochloride of the compound 13 (24 mg, 47%).

Compound 13 (dihydrochloride) $^1$H NMR (CD$_3$OD, 400 MHz): δ 0.75-1.10 (m, 1.3H), 1.45-2.00 (m, 4.7H), 2.20-2.30 (m, 1H), 2.75-3.00 (m, 1H), 3.10-3.75 (m, 12.3H), 3.90-4.05 (m, 0.7H), 4.20-4.30 (m, 0.7H), 4.70-4.80 (m, 0.3H), 6.58 (d, J=2.4 Hz, 0.3H), 6.64 (dd, J=2.4, 8.3 Hz, 0.3H), 6.74 (dd, J=2.4, 8.3 Hz, 0.7H), 6.79 (d, J=2.4 Hz, 0.7H), 7.06 (d, J=8.3 Hz, 0.3H), 7.13 (d, J=8.3 Hz, 0.7H), 7.35-7.50 (m, 5H)

Example 3

Synthesis of [(1S,3aR,5aS,6R,11bR,11cS)-10-hydroxy-14-[[(2S)-pyrrolidin-2-yl]methyl]-1,2,3a,4,5,6,7,11c-octahydro-3H-6,11b-(epiminoethano)-1,5a-methanonaphtho[1,2-e]indol-3-yl](phenyl)methanone (19)

(1) [(1S,3aR,5aS,6R,11bR,11cS)-14-(Cyclopropylmethyl)-10-hydroxy-1,2,3a,4,5,6,7,11c-octahydro-3H-6,11b-(epiminoethano)-1,5a-methanonaphtho[1,2-e]indol-3-yl](phenyl)methanone

[Formula 33]

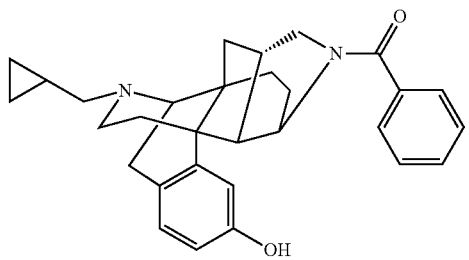

According to the method described in Example 2, the title compound 14 (968 mg) was obtained by using the compound 9 (1.00 g).

$^1$H NMR (CD$_3$OD, 400 MHz): δ 0.05-0.17 (m, 2H), 0.40-0.53 (m, 2H), 0.72-0.85 (m, 1H), 0.87-1.30 (m, 3H), 1.42-1.85 (m, 2.35H), 1.87-2.15 (m, 2.35H), 2.28-2.40 (m, 2H), 2.52-2.62 (m, 1H), 2.77-3.10 (m, 3.65H), 3.11-3.22 (m, 1.35H), 3.30-3.39 (m, 1.35H), 3.53-3.73 (m, 1.65H), 4.12-4.23 (m, 0.65H), 4.68 (t, J=6.3 Hz, 0.65H), 6.46 (d, J=2.4 Hz, 0.35H), 6.50 (dd, J=2.4, 8.3 Hz, 0.35H), 6.58 (dd, J=2.4, 8.3 Hz, 0.65H), 6.67 (d, J=2.4 Hz, 0.65H), 6.89 (d, J=8.3 Hz, 0.35H), 6.97 (d, J=8.3 Hz, 0.65H), 7.34-7.45 (m, 5 11H)

(2) [(1S,3aR,5aS,6R,11bR,11cS)-10-[(t-Butyldimethylsilyl)oxy]-14-(cyclopropylmethyl)-1,2,3a,4,5,6,7,11c-octahydro-3H-6,11b-(epiminoethano)-1,5a-methanonaphtho[1,2-e]indol-3-yl](phenyl)methanone

[Formula 34]

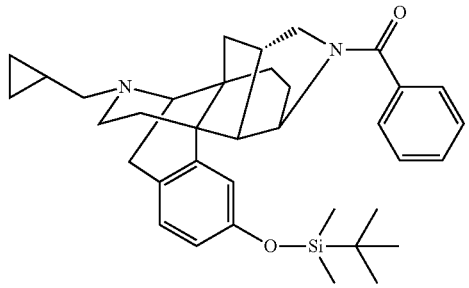

Under an argon atmosphere, the compound 14 (220 mg, 0.48 mmol) was dissolved in DMF (5 mL), the solution was added with imidazole (327 mg, 4.80 mmol), and t-butyldimethylchlorosilane (723 mg, 4.80 mmol), and the mixture was stirred at room temperature for 16 hours. The reaction mixture was diluted with ethyl acetate, and washed with water and saturated brine. The organic layer was dried over anhydrous sodium sulfate, and then concentrated. The resulting crude product was purified by silica gel column chromatography to give the title compound 15 as white amorphous (250 mg, 92%).

$^1$H NMR (CDCl$_3$, 400 MHz): δ −0.04 (s, 1.5H), 0.00 (s, 1.5H), 0.05-0.15 (m, 2H), 0.19 (s, 1.5H), 0.21 (s, 1.5H), 0.47 (d, J=7.3 Hz, 2H), 0.72-1.30 (m, 3H), 0.89 (s, 4.5H), 0.99 (s, 4.5H), 1.40-1.80 (m, 3H), 1.80-2.10 (m, 2H), 2.20-2.40 (m, 2H), 2.50-2.60 (m, 1H), 2.70-3.20 (m, 6H), 3.25-3.40 (m, 1H), 3.50-3.75 (m, 1.5H), 4.14 (t, J=7.3 Hz, 0.5H), 4.28 (dd, J=9.3, 12.7 Hz, 0.5H), 4.77 (t, J=7.3 Hz, 0.5H), 6.44 (d, J=2.4 Hz, 0.5H), 6.54 (dd, J=2.4, 8.3 Hz, 0.5H), 6.61 (dd, J=2.4, 8.3 Hz, 0.5H), 6.66 (d, J=2.4 Hz, 0.5H), 6.90 (d, J=8.3 Hz, 0.5H), 6.97 (d, J=8.3 Hz, 0.5H), 7.20-7.50 (m, 5H)

(3) [(1S,3aR,5aS,6R,11bR,11cS)-10-[(t-Butyldimethylsilyl)oxy]-1,2,3a,4,5,6,7,11c-octahydro-3H-6,11b-(epiminoethano)-1,5a-methanonaphtho[1,2-e]indol-3-yl](phenyl)methanone

[Formula 35]

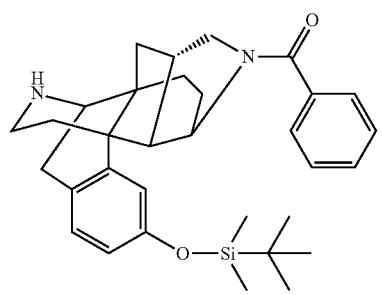

16

According to the method described in Example 1, (2), the title compound 16 (1.0 g) was obtained by using the compound 15 (1.2 g).

$^1$H NMR (CDCl$_3$, 400 MHz): δ −0.04 (s, 1.5H), 0.00 (s, 1.5H), 0.20 (s, 1.5H), 0.21 (s, 1.5H), 0.75-1.40 (m, 3H), 0.89 (s, 4.5H), 0.99 (s, 4.5H), 1.40-1.90 (m, 4H), 2.60-3.30 (m, 7H), 3.30-3.75 (m, 2.5H), 4.14 (t, J=7.3 Hz, 0.5H), 4.30 (dd, J=9.7, 13.1 Hz, 0.5H), 4.79 (t, J=7.3 Hz, 0.5H), 6.44 (d, J=2.4 Hz, 0.5H), 6.57 (dd, J=2.4, 8.3 Hz, 0.5H), 6.60-6.70 (m, 1H), 6.94 (d, J=8.3 Hz, 0.5H), 7.01 (d, J=8.3 Hz, 0.5H), 7.10-7.50 (m, 5H)

(4) t-Butyl (2S)-2-[[(1S,3aR,5aS,6R,11bR,11cS)-3-benzoyl-10-[(t-butyldimethylsilyl)oxy]-2,3, 3a,4,5,6, 7,11c-octahydro-1H-6,11b-(epiminoethano)-1,5a-methanonaphtho[1,2-e]indol-14-yl]methyl]pyrrolidine-1-carboxylate

[Formula 36]

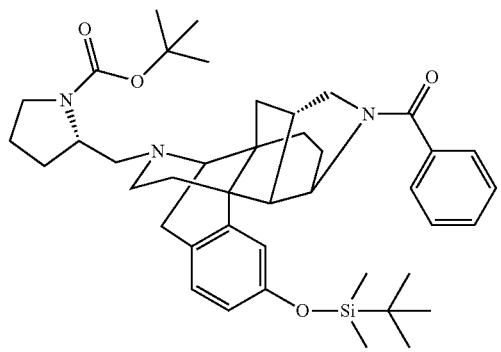

17

Under an argon atmosphere, the compound 16 (30 mg, 0.058 mmol) was dissolved in dichloromethane (1 mL), the solution was added with Boc-L-prolinal (33 μL, 0.17 mmol), and sodium triacetoxyborohydride (37 mg, 0.17 mmol), and the mixture was stirred at room temperature for 16 hours. The reaction mixture was added with 6% aqueous ammonia, and the resulting mixture was stirred for 1 hour, and extracted three times with chloroform. The organic layer was dried over anhydrous sodium sulfate, and then concentrated under reduced pressure. The resulting crude product was purified by silica gel column chromatography to give the title compound 17 (33 mg, 82%).

$^1$H NMR (CDCl$_3$, 400 MHz): δ −0.04 (s, 1.5H), 0.00 (s, 1.5H), 0.19 (s, 1.5H), 0.21 (s, 1.5H), 0.70-2.40 (m, 11H), 0.88 (s, 4.5H), 0.99 (s, 4.5H), 1.43 (s, 4.5H), 1.47 (s, 4.5H), 2.70-3.15 (m, 5H), 3.20-3.70 (m, 5H), 3.70-4.50 (m, 5H), 4.70-4.85 (m, 1H), 6.40-6.70 (m, 2H), 6.93 (d, J=8.3 Hz, 0.5H), 6.99 (d, J=8.3 Hz, 0.5H), 7.20-7.50 (m, 5H)

(5) t-Butyl (2S)-2-[[(1S,3aR,5aS,6R,11bR,11cS)-3-benzoyl-10-hydroxy-2,3,3a,4,5,6,7,11c-octahydro-1H-6,11b-(epiminoethano)-1,5a-methanonaphtho[1,2-e]indol-14-yl]methyl]pyrrolidine-1-carboxylate

[Formula 37]

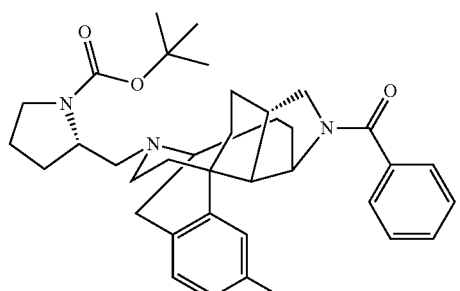

18

Under an argon atmosphere, the compound 17 (33 mg, 0.047 mmol) was dissolved in THF (0.5 mL), the solution was added with a solution of tetrabutylammonium fluoride in THF (1.0 mol/L, 120 L, 0.12 mmol) under ice cooling, and the mixture was stirred at room temperature for 2 hours. The reaction mixture was diluted with ethyl acetate, washed with water and saturated brine. The organic layer was dried over anhydrous sodium sulfate, and then concentrated. The resulting crude product was purified by silica gel column chromatography to give the title compound 18 (27 mg, 100%).

$^1$H NMR (CDCl$_3$, 400 MHz): δ 0.70-1.20 (m, 4H), 1.46 (s, 2.7H), 1.49 (s, 6.3H), 1.60-2.40 (m, 7H), 2.70-3.20 (m, 6H), 3.20-3.50 (m, 4H), 3.50-4.00 (m, 4H), 4.10-4.30 (m, 1H), 4.70-4.90 (m, 1H), 6.40-6.80 (m, 2H), 6.80-7.00 (d, 1H), 7.20-7.60 (m, 5H)

(6) [(1S,3aR,5aS,6R,11bR,11cS)-10-Hydroxy-14-[[(2S)-pyrrolidin-2-yl]methyl]-1,2,3a,4,5,6,7,11c-octahydro-3H-6,11b-(epiminoethano)-1,5a-methanonaphtho[1,2-e]indol-3-yl](phenyl)methanone

[Formula 38]

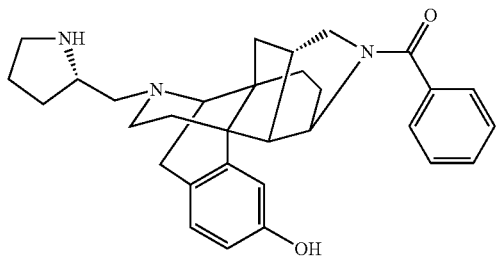

According to the method described in Example 1, (4), the title compound 19 (14 mg, 51%) was obtained by using the compound 18 (27 mg, 0.047 mmol). The resulting compound 19 was treated with a 0.5 M solution of mesylic acid in ethyl acetate (116 μL, 0.058 mmol) to give mesylate of the compound 19 (20 mg, 51%).

Compound 19 (dimesylate)$^1$H NMR (CD$_3$ OD, 400 MHz): δ 0.75-1.30 (m, 1.3H), 1.45-2.00 (m, 6.7H), 2.05-2.45 (m, 3H), 2.70-2.90 (m, 2H), 2.73 (s, 6H), 2.90-3.10 (m, 1H), 3.10-3.85 (m, 10.3H), 3.90-4.05 (m, 0.7H), 4.10-4.35 (m, 1.7H), 4.65-4.80 (m, 0.3H), 6.58 (s, 0.3H), 6.65 (d, J=8.3 Hz, 0.3H), 6.75 (d, J=8.3 Hz, 0.7H), 6.79 (s, 0.7H), 7.05 (d, J=8.3 Hz, 0.3H), 7.13 (d, J=8.3 Hz, 0.7H), 7.35-7.50 (m, 5H)

Example 4

Synthesis of [(1S,3aR,5aS,6R,11bR,11cS)-10-hydroxy-14-[[(2S)-11-methylpyrrolidin-2-yl]methyl]-1,2,3a,4,5,6,7,11c-octahydro-3H-6,11b-(epiminoethano)-1,5a-methanonaphtho[1,2-e]indol-3-yl](phenyl)methanone (20)

[Formula 39]

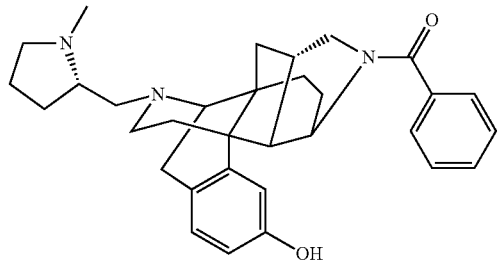

Under an argon atmosphere, the compound 19 (48 mg, 0.10 mmol) was dissolved in dichloromethane (1 mL), the solution was added with 37% aqueous formaldehyde (33 μL, 0.45 mmol), zinc chloride (7 mg, 0.05 mmol), and sodium cyanoborohydride (13 mg, 0.12 mmol) under ice cooling, and the mixture was stirred at room temperature for 16 hours. The reaction mixture was added with 6% aqueous ammonia on an ice bath, and the mixture was stirred at room temperature for 1 hour, and then extracted three times with chloroform. The organic layer was dried over anhydrous sodium sulfate, and then concentrated under reduced pressure. The resulting crude product was purified by preparative TLC to give the title compound 20 (10 mg, 17%).

Compound 20 (dimesylate)$^1$H NMR (CD$_3$ OD, 400 MHz): δ 0.75-1.25 (m, 1.3H), 1.40-1.95 (m, 4.7H), 1.95-2.35 (m, 4.3H), 2.45-2.60 (m, 0.7H), 2.73 (s, 6H), 2.80-3.05 (m, 2H), 3.09 (s, 3H), 3.10-4.10 (m, 13H), 4.15-4.35 (m, 0.7H), 4.70-4.80 (m, 0.3H), 6.58 (s, 0.3H), 6.66 (d, J=8.3 Hz, 0.3H), 6.74 (d, J=8.3 Hz, 0.7H), 6.79 (s, 0.7H), 7.07 (d, J=8.3 Hz, 0.3H), 7.15 (d, J=8.3 Hz, 0.7H), 7.35-7.50 (m, 5H)

Example 5

Synthesis of [(1S,3aR,5aS,6R,11bR,11cS)-14-(azetidin-2-ylmethyl)-10-hydroxy-1,2,3a,4,5,6,7,11c-octahydro-3H-6,11b-(epiminoethano)-1,5a-methanonaphtho[1,2-e]indol-3-yl](phenyl)methanone (21)

[Formula 40]

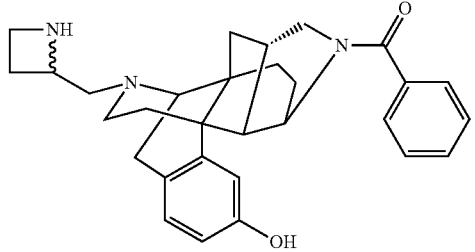

According to the methods described in Example 3, (4), (5) and (6), a mixture of diastereomers of the title compound was obtained by using the compound 16 (50 mg, 0.097 mmol), and 1-(t-butoxycarbonyl)-2-azetidinecarboxaldehyde (54 mg, 0.29 mmol). Further, the diastereomers (21a and 21b) were separated by preparative TLC, and each diastereomer was made into mesylate.

Compound 21a (dimesylate)$^1$H NMR (CD$_3$ OD, 400 MHz): δ 0.75-1.25 (m, 1.3H), 1.45-2.00 (m, 5.7H), 2.15-2.35 (m, 1H), 2.50-3.05 (m, 4H), 2.72 (s, 6H), 3.10-4.05 (m, 10.3H), 4.10-4.30 (m, 1.7H), 4.65-4.80 (m, 0.3H), 5.10-5.20 (m, 0.7H), 6.58 (d, J=2.4 Hz, 0.3H), 6.65 (dd, J=2.4, 8.3 Hz, 0.3H), 6.74 (dd, J=2.4, 8.3 Hz, 0.7H), 6.79 (d, J=2.4 Hz, 0.7H), 7.06 (d, J=8.3 Hz, 0.3H), 7.14 (d, J=8.3 Hz, 0.71H), 7.35-7.50 (m, 5H)

Compound 21b (dimesylate)$^1$H NMR (CD$_3$ OD, 400 MHz): δ 0.75-1.25 (m, 1.3H), 1.40-2.00 (m, 5.7H), 2.15-2.35 (m, 1H), 2.35-2.50 (m, 1H), 2.70-3.10 (m, 3H), 2.73 (s, 6H), 3.10-4.15 (m, 11.3H), 4.15-4.30 (m, 0.7H), 4.70-4.80 (m, 0.3H), 4.90-5.10 (m, 0.7H), 6.58 (d, J=2.4 Hz, 0.3H), 6.64 (dd, J=2.4, 8.3 Hz, 0.3H), 6.74 (dd, J=2.4, 8.3 Hz, 0.7H), 6.79 (d, J=2.4 Hz, 0.7H), 7.05 (d, J=8.3 Hz, 0.3H), 7.13 (d, J=8.3 Hz, 0.7H), 7.35-7.50 (m, 5H)

Example 6

Synthesis of [(1S,3aR,5aS,6R,11bR,11cS)-10-hydroxy-14-[3-(phenylamino)propyl]-1,2,3a,4,5,6,7,11c-octahydro-3H-6,11b-(epiminoethano)-1,5a-methanonaphtho[1,2-e]indol-3-yl](phenyl)methanone (23)

(1) [(1S,3aR,5aS,6R,11bR,11cS)-10-[(t-Butyldimethylsilyl)oxy]-14-[3-(phenylamino)propyl]-1,2,3a,4,5,6,7,11c-octahydro-3H-6,11b-(epiminoethano)-1,5a-methanonaphtho[1,2-e]indol-3-yl](phenyl)methanone

[Formula 41]

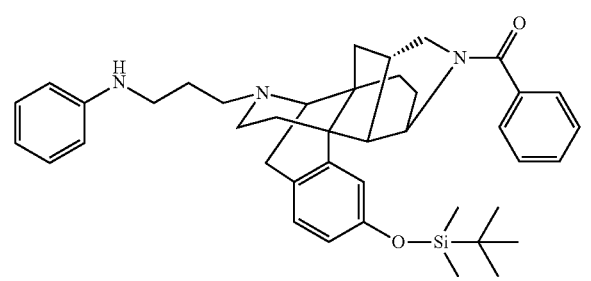

22

Under an argon atmosphere, the compound 16 (30 mg, 0.058 mmol) was dissolved in acetonitrile (0.5 mL), the solution was added with 3-chloroiodopropane (9 μL, 0.087 mmol), and potassium carbonate (32 mg, 0.23 mmol), and the mixture was stirred at 70° C. for 16 hours. Disappearance of the starting material was confirmed by thin layer chromatography, and then the reaction mixture was added with aniline (53 μL, 0.58 mmol), and potassium iodide (48 mg, 0.29 mmol) at room temperature, and the mixture was stirred at 70° C. for further 16 hours. The reaction mixture was cooled to room temperature, then diluted with ethyl acetate, and washed with water and saturated brine. The organic layer was dried over anhydrous sodium sulfate, and then concentrated. The resulting crude product was purified by silica gel column chromatography to give the title compound 22 (13 mg, 34%).

$^1$H NMR (CDCl$_3$, 400 MHz): δ −0.04 (s, 1.5H), 0.00 (s, 1.5H), 0.20 (s, 1.5H), 0.21 (s, 1.5H), 0.70-1.10 (m, 1H), 0.89 (s, 4.5H), 0.99 (s, 4.5H), 1.10-1.35 (m, 3H), 1.40-2.15 (m, 5H), 2.40-2.60 (m, 3H), 2.75-3.10 (m, 4.5H), 3.10-3.35 (m, 3.5H), 3.50-3.70 (m, 1.5H), 4.10-4.40 (m, 2H), 4.70-4.85 (m, 0.5H), 6.45 (d, J=2.4 Hz, 0.5H), 6.50-6.75 (m, 4.5H), 6.92 (d, J=8.3 Hz, 0.5H), 6.99 (d, J=8.3 Hz, 0.5H), 7.15 (d, J=8.8 Hz, 1H), 7.19 (d, J=8.8 Hz, 1H), 7.20-7.50 (m, 5H)

(2) [(1S,3aR,5aS,6R,11bR,1cS)-10-Hydroxy-14-[3-(phenylamino)propyl]-1,2,3a,4,5,6,7,11c-octahydro-3H-6,11b-(epiminoethano)-1,5a-methanonaphtho[1,2-e]indol-3-yl](phenyl)methanone

[Formula 42]

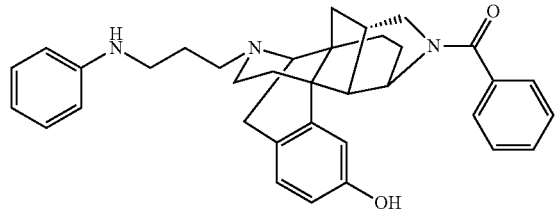

23

According to the method described in Example 3, (5), the title compound 23 and hydrochloride thereof (7 mg) were obtained by using the compound 22 (13 mg).

Compound 23 (dihydrochloride)$^1$H NMR (CD$_3$ OD, 400 MHz): δ 0.75-1.25 (m, 1.3H), 1.45-2.00 (m, 4.7H), 2.10-2.45 (m, 3H), 2.70-2.90 (m, 1H), 3.00-3.80 (m, 11.7H), 3.85-4.00 (m, 1.3H), 4.15-4.30 (m, 0.7H), 4.70-4.80 (m, 0.3H), 6.57 (d, J=2.4 Hz, 0.3H), 6.64 (dd, J=2.4, 8.3 Hz, 0.3H), 6.74 (dd, J=2.4, 8.3 Hz, 0.7H), 6.78 (d, J=2.4 Hz, 0.7H), 7.05 (d, J=8.3 Hz, 0.3H), 7.13 (d, J=8.3 Hz, 0.7H), 7.35-7.70 (m, 10H)

Example 7

Synthesis of (1S,3aR,5aS,6R,11bR,11cS)-14-(2-aminoethyl)-10-hydroxy-N-isopropyl-1,2,3a,4,5,6,7,11c-octahydro-3H-6,11b-(epiminoethano)-1,5a-methanonaphtho[1,2-e]indole-3-carboxamide (31)

(1) 2,2,2-Trichloroethyl (1S,3aR,5aS,6R,11bR,11cS)-14-(cyclopropylmethyl)-10-methoxy-1,2,3a,4,5,6,7,11c-octahydro-3H-6,11b-(epiminoethano)-1,5a-methanonaphtho[1,2-e]indole-3-carboxylate

[Formula 43]

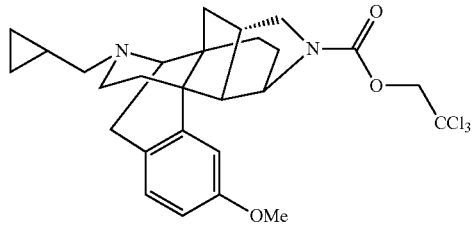

24

Under an argon atmosphere, the compound 8 (1.0 g, 2.74 mmol) was dissolved in dichloromethane (10 mL), the solution was cooled on ice, and then added with potassium carbonate (768 mg, 5.49 mmol), and 2,2,2-trichloroethyl chloroformate (406 μL, 3.02 mmol), and the mixture was stirred at room temperature for 1 hour. The reaction mixture was added with saturated aqueous sodium hydrogencarbonate, the mixture was extracted with chloroform, and then the organic layer was dried over anhydrous sodium sulfate, and concentrated. The resulting crude product was purified by silica gel column chromatography to give the title compound 24 (1.39 g, 94%).

$^1$H NMR (CDCl$_3$, 400 MHz): δ 0.05-0.20 (m, 2H), 0.40-0.55 (m, 2H), 0.70-0.92 (m, 2H), 1.10-1.20 (m, 2H), 1.35-1.60 (m, 2H), 1.65-1.75 (m, 1H), 1.85-2.05 (m, 2H), 2.24-2.36 (m, 2H), 2.55-2.60 (m, 1H), 2.85-2.95 (m, 2H), 3.00-3.15 (m, 3H), 3.32-3.45 (m, 1H), 3.50-3.63 (m, 1H), 3.74-3.86 (m, 4H), 4.28 (dd, J=5.4, 8.3 Hz, 1H), 4.57 (d, J=12.2 Hz, 0.5H), 4.66 (d, J=12.2 Hz, 0.5H), 4.78 (d, J=12.2 Hz, 0.5H), 4.87 (d, J=12.2 Hz, 0.5H), 6.64-6.72 (m, 2H), 7.02 (d, J=8.3 Hz, 0.5H), 7.03 (d, J=8.3 Hz, 0.5H)

(2) 2,2,2-Trichloroethyl (1S,3aR,5aS,6R,11bR,11cS)-14-(cyclopropylmethyl)-10-hydroxy-1,2,3a,4,5,6,7,11c-octahydro-3H-6,11b-(epiminoethano)-1,5a-methanonaphtho[1,2-e]indole-3-carboxylate

[Formula 44]

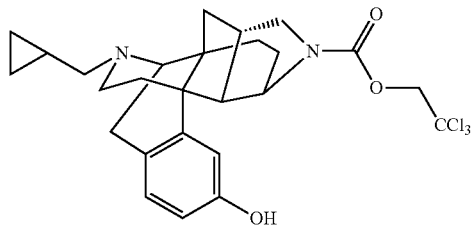

25

According to the method described in Example 2, the title compound 25 (973 mg) was obtained by using the compound 24 (1.0 g).

(3) 2,2,2-Trichloroethyl (1S,3aR,5aS,6R,11bR,11cS)-10-[(t-butyldimethylsilyl)oxy]-14-(cyclopropylmethyl)-1,2,3a,4,5,6,7,11c-octahydro-3H-6,11b-(epiminoethano)-1,5a-methanonaphtho[1,2-e]indole-3-carboxylate

[Formula 45]

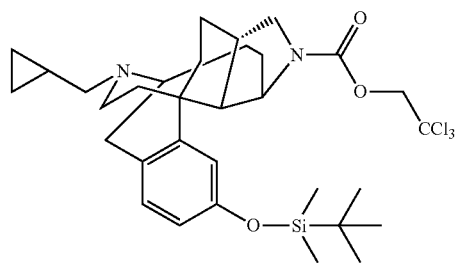

26

According to the method described in Example 3, (2), the title compound 26 (1.02 g) was obtained by using the compound 25 (973 mg).

(4) 2,2,2-Trichloroethyl (1S,3aR,5aS,6R,11bR,11cS)-10-[(t-butyldimethylsilyl)oxy]-1,2,3a,4,5,6,7,11c-octahydro-3H-6,11b-(epiminoethano)-1,5a-methanonaphtho[1,2-e]indole-3-carboxylate

[Formula 46]

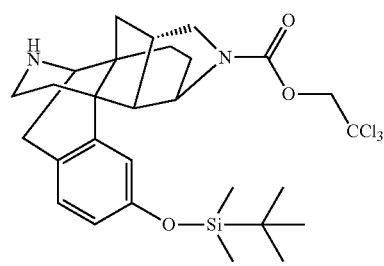

27

According to the method described in Example 1, (2), the title compound 27 (470 mg) was obtained by using the compound 26 (800 mg).

$^1$H NMR (CDCl$_3$, 400 MHz): δ 0.15 (s, 1.5H), 0.16 (s, 1.5H), 0.17 (s, 1.5H), 0.18 (s, 1.5H), 0.75-1.00 (m, 1H), 0.96 (s, 4.5H), 0.97 (s, 4.5H), 1.30-1.80 (m, 5H), 2.00-2.15 (m, 1H), 2.70-3.00 (m, 1H), 3.00-3.40 (m, 5H), 3.40-3.65 (m, 2H), 3.70-3.90 (m, 2H), 4.25-4.40 (m, 1H), 4.62 (d, J=11.7 Hz, 0.5H), 4.67 (d, J=11.7 Hz, 0.5H), 4.77 (d, J=11.7 Hz, 0.5H), 4.78 (d, J=11.7 Hz, 0.5H), 6.60-6.80 (m, 2H), 7.06 (d, J=8.3 Hz, 0.5H), 7.07 (d, J=8.3 Hz, 0.5H)

(5) 2,2,2-Trichloroethyl (1S,3aR,5aS,6R,11bR, 11cS)-14-[2-[(t-butoxycarbonyl)amino]ethyl]-10-[(t-butyldimethylsilyl)oxy]-1,2,3a, 4,5,6,7,11c-octahydro-3H-6,11b-(epiminoethano)-1,5a-methanonaphtho[1,2-e]indole-3-carboxylate

[Formula 47]

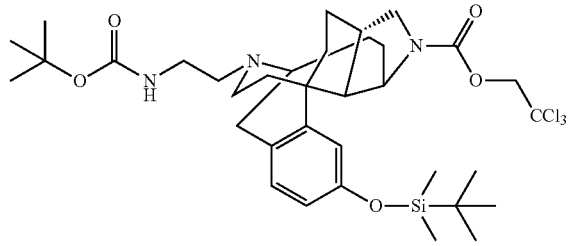

28

According to the method described in Example 1, (3), the title compound 28 (80 mg) was obtained by using the compound 27 (150 mg).

$^1$H NMR (CDCl$_3$, 400 MHz): δ 0.17 (s, 3H), 0.18 (s, 3H), 0.75-0.90 (m, 1H), 0.96 (s, 4.5H), 0.97 (s, 4.5H), 1.10-1.25 (m, 2H), 1.40-1.50 (m, 1H), 1.46 (s, 9H), 1.60-1.80 (m, 1H), 1.80-2.00 (m, 1H), 2.00-2.20 (m, 1H), 2.35-2.70 (m, 3H), 2.80-3.10 (m, 6H), 3.10-3.35 (m, 3H), 3.50-3.65 (m, 1H), 3.70-3.90 (m, 1H), 4.20-4.35 (m, 1H), 4.62 (d, J=11.7 Hz, 0.5H), 4.67 (d, J=12.2 Hz, 0.5H), 4.77 (d, J=11.7 Hz, 0.5H), 4.78 (d, J=12.2 Hz, 0.5H), 4.89 (br s, 1H), 6.50-6.70 (m, 2H), 6.97 (d, J=8.3 Hz, 0.5H), 6.98 (d, J=8.3 Hz, 0.5H)

(6) t-Butyl[2-[(1S,3aR,5aS,6R,11bR,11cS)-10-[(t-butyldimethylsilyl)oxy]-2,3,3a,4,5,6,7,11c-octahydro-1H-6,11b-(epiminoethano)-1,5a-methanonaphtho[1,2-e]indol-14-yl]ethyl]carbamate

[Formula 48]

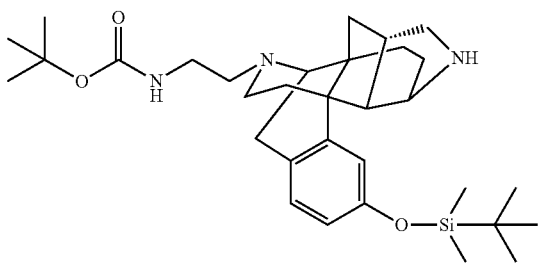

29

Under an argon atmosphere, the compound 28 (80 mg, 0.11 mmol) was dissolved in ethanol (1 mL), the solution was added with zinc powder (144 mg, 2.2 mmol), and the mixture was stirred at 70° C. for 4 hours. The reaction mixture was cooled to room temperature, then filtered through Celite, and concentrated to give a crude product of the title compound 29 (61 mg).

(7) t-Butyl[2-[(1S,3aR,5aS,6R,11bR,11cS)-10-[(t-butyldimethyisilyl)oxy]-3-(isopropylcarbamoyl)-2,3, 3a,4,5,6,7,11c-octahydro-1H-6,11b-(epiminoethano)-1,5a-methanonaphtho[1,2-e]indol-14-yl]ethyl] carbamate

[Formula 49]

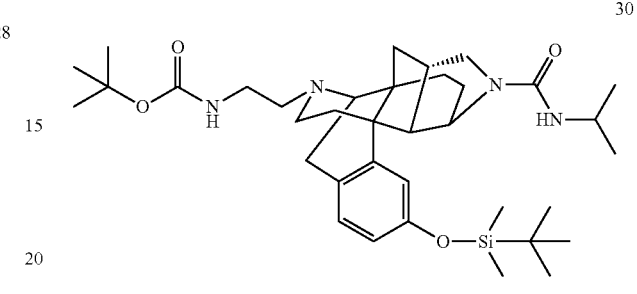

30

Under an argon atmosphere, the crude product (30 mg) obtained in (6) mentioned above was dissolved in dichloromethane (1 mL), the solution was added with triethylamine (20 μL, 0.15 mmol), and isopropyl isocyanate (7 μL, 0.074 mmol), and the mixture was stirred at room temperature for 16 hours. The reaction mixture was added with saturated aqueous sodium hydrogencarbonate, the mixture was extracted with chloroform, and then the organic layer was dried over anhydrous sodium sulfate, and concentrated. The resulting crude product was purified by silica gel column chromatography to give the title compound 30 (30 mg, 85%).

1H NMR (CDCl$_3$, 400 MHz): δ 0.17 (s, 6H), 0.60-1.75 (m, 5H), 0.97 (s, 9H), 1.12 (d, J=6.8 Hz, 3H), 1.14 (d, J=6.8 Hz, 3H), 1.46 (s, 9H), 1.80-2.00 (m, 1H), 2.00-2.15 (m, 1H), 2.35-2.65 (m, 3H), 2.70-3.10 (m, 6H), 3.10-3.30 (m, 3H), 3.30-3.40 (m, 1H), 3.60-3.75 (m, 1H), 3.80-4.00 (m, 2H), 4.12 (br s, 1H), 4.89 (br s, 1H), 6.55-6.65 (m, 2H), 6.97 (d, J=8.3 Hz, 1H)

(8) (1S,3aR,5aS,6R,11bR,11cS)-14-(2-Aminoethyl)-10-hydroxy-N-isopropyl-1,2,3a,4,5,6,7,11c-octahydro-3H-6,11b-(epiminoethano)-1,5a-methanonaphtho[1,2-e]indole-3-carboxamide

[Formula 50]

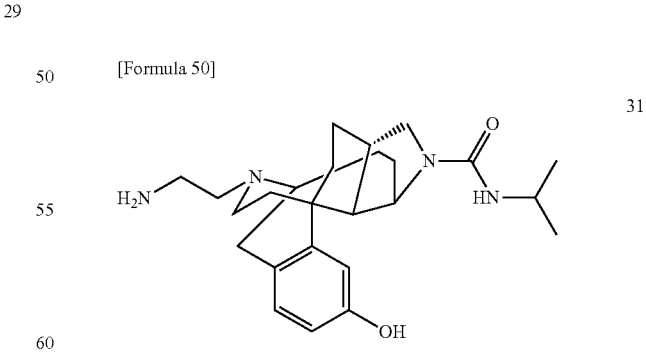

31

According to the methods described in Example 3, (5) and Example 1, (4), the title compound 31 (13 mg) was obtained by using the compound 30 (30 mg). Compound 31 (dimesylate)$^1$H NMR (CD$_3$ OD, 400 MHz): δ 0.75-0.95 (m, 1H), 1.10 (d, J=6.2 Hz, 3H), 1.12 (d, J=6.2 Hz, 3H), 1.25-1.40 (m, 1H), 1.45-1.70 (m, 3H), 1.75-1.90 (m, 1H), 2.15-2.30 (m, 1H), 2.70-2.80 (m, 1H), 2.72 (s, 6H), 2.80-2.90 (m, 1H), 2.90-3.05 (m, 1H), 3.10-3.75 (m, 10H), 3.80-4.00 (m, 2H), 4.25-4.35 (m, 111H), 6.70 (dd, J=2.4, 8.3 Hz, 1H), 6.74 (d, J=2.4 Hz, 1H), 7.11 (d, J=8.3 Hz, 1H)

Example 8

Synthesis of (1S,3aR,5aS,6R,11bR,11cS)-14-(2-aminoethyl)-3-(4,6-dimethylpyrimidin-2-yl)-2, 3,3a, 4,5,6,7,11c-octahydro-1H-6,11b-(epiminoethano)-1, 5a-methanonaphtho[1,2-e]indol-10-ol (33)

(1) t-Butyl[2-[(1S,3aR,5aS,6R,11bR,11cS)-10-[(t-butyldimethylsilyl)oxy]-3-(4,6-dimethylpyrimidin-2-yl)-2,3,3a,4,5,6,7,11c-octahydro-1H-6,11b-(epiminoethano)-1,5a-methanonaphtho[1,2-e]indol-14-yl]ethyl]carbamate

[Formula 51]

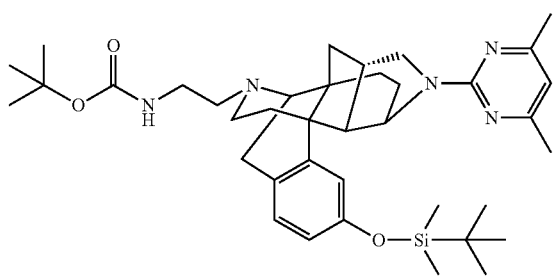

32

Under an argon atmosphere, the crude product of the compound 29 (30 mg) obtained in Example 7, (6) was dissolved in acetonitrile (1 mL), the solution was added with potassium carbonate (20 mg, 0.15 mmol), and 2-chloro-4,6-dimethylpyrimidine (10 mg, 0.074 mmol), and the mixture was stirred at 70° C. for 16 hours. The reaction mixture was cooled to room temperature, then diluted with ethyl acetate, and washed with water and saturated brine. The organic layer was dried over anhydrous sodium sulfate, and then concentrated. The resulting crude product was purified by silica gel column chromatography to give the title compound 32 (22 mg, 62%).

$^1$H NMR (CDCl$_3$, 400 MHz): δ 0.20 (s, 3H), 0.21 (s, 3H), 0.71-0.91 (m, 1H), 0.99 (s, 9H), 1.11-1.31 (m, 2H), 1.41-1.81 (m, 2H), 1.47 (s, 9H), 1.86-2.01 (m, 1H), 2.06-2.21 (m, 1H), 2.24 (br s, 6H), 2.41-2.71 (m, 3H), 2.81-3.41 (m, 9H), 3.65 (d, J=11.7 Hz, 1H), 3.88 (dd, J=7.8, 11.7 Hz, 1H), 4.51-4.71 (m, 1H), 4.95 (br s, 1H), 6.21 (s, 1H), 6.63 (dd, J=2.4, 8.3 Hz, 1H), 6.70 (d, J=2.4 Hz, 1H), 6.97 (d, J=8.3 Hz, 1H)

(2) (1S,3aR,5aS,6R,11bR,11cS)-14-(2-Aminoethyl)-3-(4,6-dimethylpyrimidin-2-yl)-2,3,3a,4,5,6,7,11c-octahydro-1H-6,11b-(epiminoethano)-1,5a-methanonaphtho[1,2-e]indol-10-ol

[Formula 52]

33

According to the methods described in Example 3, (5) and Example 1, (4), the title compound 33 (10 mg) was obtained by using the compound 32 (22 mg). Compound 33 (trimesylate) 1H NMR (CD$_3$OD, 400 MHz): δ 0.80-1.10 (m, 1H), 1.40-1.70 (m, 4H), 1.80-1.95 (m, 1H), 2.25-2.40 (m, 1H), 2.45 (br s, 3H), 2.52 (br s, 3H), 2.70-2.80 (m, 1H), 2.72 (s, 9H), 2.80-2.95 (m, 1H), 3.05-3.20 (m, 1H), 3.20-3.70 (m, 9H), 3.84 (d, J=12.2 Hz, 1H), 4.00-4.10 (m, 2H), 6.70-6.80 (m, 3H), 7.15 (d, J=8.3 Hz, 1H)

Example 9

Synthesis of [(1S,3aR,5aS,6R,11bR,11cS)-14-(3-aminopropyl)-1,2,3a,4,5,6,7,11c-octahydro-3H-6,11b-(epiminoethano)-1,5a-methanonaphtho[1,2-e]indol-3-yl](phenyl)methanone (38)

(1) [(1S,3aR,5aS,6R,11bR,11cS)-14-(Cyclopropylmethyl)-10-[(1-phenyl-1H-tetrazol-5-yl)oxy]-1,2,3a,4,5,6,7,11c-octahydro-3H-6,11b-(epiminoethano)-1,5a-methanonaphtho[1,2-e]indol 3-yl](phenyl)methanone

[Formula 53]

34

Under an argon atmosphere, the compound 14 (1.31 g, 2.87 mmol) was dissolved in DMF (10 mL), the solution was added with potassium carbonate (995 mg, 7.20 mmol), and 5-chloro-1-phenyl-1H-tetrazole (622 mg, 3.45 mmol), and the mixture was stirred at room temperature for 17 hours.

The reaction mixture was added with water, and the resulting mixture was extracted three times with diethyl ether. The organic layer was dried over anhydrous sodium sulfate, and then concentrated. The resulting crude product was purified by silica gel column chromatography to give the title compound 34 (1.59 g, 92%).

$^1$H NMR (CDCl$_3$, 400 MHz): δ 0.05-0.15 (m, 2H), 0.45-0.55 (m, 2H), 0.75-1.00 (m, 2H), 1.10-1.30 (m, 2H), 1.45-1.65 (m, 2.3H), 1.70-1.80 (m, 0.7H), 1.85-2.10 (m, 2H), 2.25-2.40 (m, 2H), 2.55-2.65 (m, 1H), 2.85-3.05 (m, 4H), 3.10-3.20 (m, 1H), 3.30-3.45 (m, 1H), 3.55 (d, J=10.2 Hz, 0.7H), 3.65-3.70 (m, 1H), 4.25 (dd, J=9.3, 13.2 Hz, 0.3H), 4.33 (t, J=7.8 Hz, 0.3H), 4.78 (t, J=7.3 Hz, 0.7H), 7.10-7.22 (m, 3H), 7.30-7.45 (m, 5H), 7.60-7.65 (m, 3H), 7.75-7.85 (m, 2H)

(2) [(1S,3aR,5aS,6R,11bR,11cS)-14-(Cyclopropylmethyl)-1,2,3a,4,5,6,7,11c-octahydro-3H-6,11b-(epiminoethano)-1,5a-methanonaphtho[1,2-e]indol-3-yl](phenyl)methanone

[Formula 54]

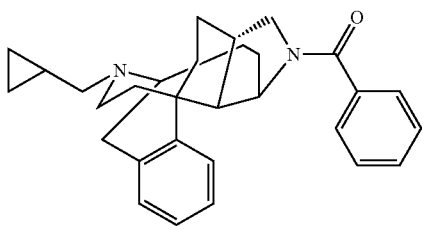

34

The compound 34 (277 mg, 0.46 mmol) was dissolved in acetic acid (17 mL), the solution was added with 10% palladium/carbon (434 mg), and the mixture was stirred at 80° C. for 6 hours under a hydrogen atmosphere. The reaction mixture was filtered through Celite, and then concentrated. The resulting residue was purified by silica gel column chromatography to give the title compound 35 (197 mg, 97%).

(3) [(1S,3aR,5aS,6R,11bR,11cS)-1,2,3a,4,5,6,7,11c-Octahydro-3H-6,11b-(epiminoethano)-1,5a-methanonaphtho[1,2-e]indol-3-yl](phenyl)methanone

[Formula 55]

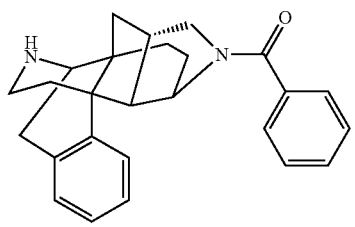

36

According to the method described in Example 1, (2), the title compound 36 (77 mg) was obtained by using the compound 35 (186 mg).

$^1$H NMR (CDCl$_3$, 400 MHz): δ 0.70-1.00 (m, 1.4H), 1.05-1.90 (m, 5.6H), 2.60-2.85 (m, 2H), 2.90-3.55 (m, 8.6H), 4.10-4.35 (m, 0.8H), 4.82 (t, J=7.3 Hz, 0.6H), 7.00-7.20 (m, 4H), 7.30-7.50 (m, 5H)

(4) t-Butyl[3-[(1S,3aR,5aS,6R,11bR,11cS)-3-benzoyl-2,3,3a,4,5,6,7,11c-octahydro-1H-6,11b-(epiminoethano)-1,5a-methanonaphtho[1,2-e]indol-14-yl]propyl]carbamate

[Formula 56]

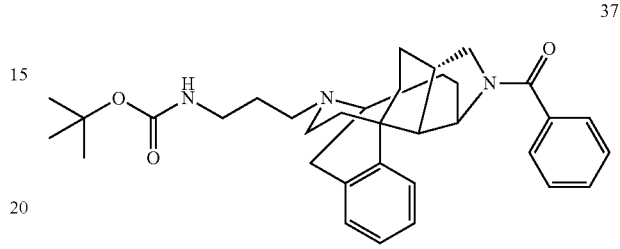

37

According to the method described in Example 1, (3), the title compound 37 (12 mg) was obtained by using the compound 36 (19 mg).

$^1$H NMR (CDCl$_3$, 400 MHz): δ 0.65-0.95 (m, 1.4H), 1.10-1.35 (m, 2.6H), 1.40-2.10 (m, 16H), 2.44-2.56 (m, 3H), 2.90-3.35 (m, 6.4H), 3.50-3.75 (m, 2H), 4.15 (t, J=8.0 Hz, 0.4H), 4.22-4.32 (m, 0.6H), 4.74-4.82 (m, 0.6H), 5.50 (br s, 0.6H), 5.68 (br s, 0.4H), 6.98-7.20 (m, 4H), 7.31-7.47 (m, 5H)

(5) [(1S,3aR,5aS,6R,11bR,11cS)-14-(3-Aminopropyl)-1,2,3a,4,5,6,7,11c-octahydro-3H-6,11b-(epiminoethano)-1,5a-methanonaphtho[1,2-e]indol-3-yl](phenyl)methanone

[Formula 57]

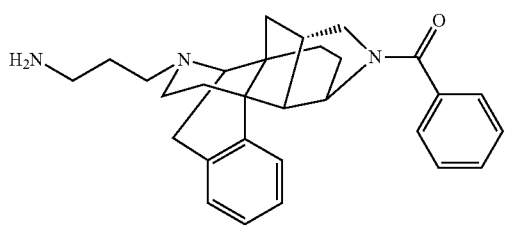

38

According to the method described in Example 3 (5), the title compound 38 (9 mg) was obtained by using the compound 37 (11 mg).

$^1$H NMR (CDCl$_3$, 400 MHz): δ 0.65-0.95 (m, 1.4H), 1.05-1.20 (m, 2H), 1.40-1.80 (m, 5.6H), 1.83-2.25 (m, 4H), 2.40-2.55 (m, 3H), 2.75-2.85 (m, 2H), 2.90-3.10 (m, 4H), 3.23 (t, J=10.2 Hz, 1H), 3.54 (d, J=10.7 Hz, 0.6H), 3.57-3.70 (m, 1H), 4.15 (t, J=8.0 Hz, 0.4H), 4.20-4.30 (m, 0.4H), 4.74-4.82 (m, 0.6H), 6.95-7.20 (m, 4H), 7.30-7.45 (m, 5H)

Examples 10 to 28

According to the methods described in the tables, the compounds of Examples 10 to 28 (free bases, hydrochlorides thereof, and mesylates thereof) were obtained.

TABLE 1

| Compound No. | | Structural formula | ¹H NMR | Synthesis method |
|---|---|---|---|---|
| Example 10 | 39 | | (Dimesilate, CD₃OD) δ 0.75-1.25 (m, 1.3H), 1.45-2.00 (m, 4.7H), 2.15-2.35 (m, 1H), 2.70-3.05 (m, 3H), 2.73 (s, 6H), 2.82 (s, 3H), 3.10-3.80 (m, 10H), 3.90-4.00 (m, 1H), 4.20-4.30 (m, 0.7H), 4.70-4.80 (m, 0.3H), 6.58 (d, J = 2.4 Hz, 0.3H), 6.65 (dd, J = 2.4, 8.3 Hz, 0.3H), 6.74 (dd, J = 2.4, 8.3 Hz, 0.7H), 6.79 (d, J = 2.4 Hz, 0.7H), 7.06 (d, J = 8.3 Hz, 0.3H), 7.14 (d, J = 8.3 Hz, 0.3H), 7.35-7.50 (m, 5H). | a |
| Example 11 | 40 | | (Dimesilate, CD₃OD) δ 0.75-1.95 (m, 6H), 2.00-2.25 (m, 1H), 2.73 (s, 6H), 2.96 (br s, 6H), 3.00-3.50 (m, 12.3H), 3.50-3.80 (m, 1.7H), 4.15-4.30 (m, 0.7H), 4.60-4.80 (m, 0.3H), 6.50-6.80 (m, 2H), 6.90-7.05 (m, 1H), 7.35-7.50 (m, 5H). | b |
| Example 12 | 41 | | (Dihydrochloride, CD₃OD) δ 0.75-1.25 (m, 1.3H), 1.45-2.00 (m, 4.7H), 2.05-2.30 (m, 3H), 2.70-2.90 (m, 1.3H), 3.00-3.60 (m, 9.7H), 3.66 (d, J = 12.2 Hz, 1H), 3.70-3.80 (m, 0.7H), 3.90-4.00 (m, 1.3H), 4.20-4.30 (m, 0.7H), 4.70-4.80 (m, 0.3H), 6.58 (d, J = 2.4 Hz, 0.3H), 6.64 (dd, J = 2.4, 8.3 Hz, 0.3H), 6.74 (dd, J = 2.4, 8.3 Hz, 0.7H), 6.79 (d, J = 2.4 Hz, 0.7H), 7.06 (d, J = 8.3 Hz, 0.7H), 7.13 (d, J = 8.3 Hz, 0.7H), 7.35-7.50 (m, 5H). | c |
| Example 13 | 42 | | (Dihydrochloride, CD₃OD) δ 0.75-1.25 (m, 1.3H), 1.45-2.00 (m, 8.7H), 2.10-2.25 (m, 1H), 2.70-2.90 (m, 1H), 2.95-3.10 (m, 3H), 3.10-3.55 (m, 7H), 3.55-3.65 (m, 1.3H), 3.65-3.80 (m, 0.7H), 3.85-3.95 (m, 1H), 4.20-4.30 (m, 0.7H), 4.70-4.80 (m, 0.3H), 6.58 (d, J = 2.4 Hz, 0.3H), 6.64 (dd, J = 2.4, 8.3 Hz, 0.3H), 6.74 (dd, J = 2.4, 8.3 Hz, 0.7H), 6.79 (d, J = 2.4 Hz, 0.7H), 7.05 (d, J = 8.3 Hz, 0.3H), 7.13 (d, J = 8.3 Hz, 0.7H), 7.35-7.50 (m, 5H). | d |
| Example 14 | 43 | | (Dimesilate, CD₃OD) δ 0.75-1.10 (m, 1H), 1.10-2.00 (m, 8H), 2.20-2.40 (m, 1H), 2.72 (s, 6H), 2.70-3.10 (m, 4H), 3.10-3.80 (m, 7.3H), 3.80-4.10 (m, 1.7H), 4.15-4.30 (m, 0.7H), 4.70-4.80 (m, 0.3H), 6.58 (d, J = 2.4 Hz, 0.3H), 6.64 (dd, J = 2.4, 8.3 Hz, 0.3H), 6.74 (dd, J = 2.4, 8.3 Hz, 0.7H), 6.79 (d, J = 2.4 Hz, 0.7H), 7.05 (d, J = 8.3 Hz, 0.3H), 7.14 (d, J = 8.3 Hz, 0.7 H), 7.35-7.50 (m, 5H). | a |
| Example 15 | 44 | | (Dimesilate, CD₃OD) δ 0.75-1.10 (m, 1H), 1.10-2.00 (m, 8H), 2.20-2.40 (m, 1H), 2.73 (s, 6H), 2.70-3.10 (m, 4H), 3.10-4.10 (m, 9H), 4.20-4.30 (m, 0.7H), 4.70-4.80 (m, 0.3H), 6.58 (d, J = 2.4 Hz, 0.3H), 6.65 (dd, J = 2.4, 8.3 Hz, 0.3H), 6.75 (dd, J = 2.4, 8.3 Hz, 0.7H), 6.79 (d, J = 2.4 Hz, 0.7H), 7.06 (d, J = 8.3 Hz, 0.3H), 7.14 (d, J = 8.3 Hz, 0.7H), 7.35-7.50 (m, 5H). | a |

TABLE 2

| Compound No. | | Structural formula | $^1$H NMR | Synthesis method |
|---|---|---|---|---|
| Example 16 | 45 | | (Dimesilate, CD$_3$OD) δ 0.75-1.10 (m, 2H), 1.10-1.40 (m, 4H), 1.40-2.00 (m, 4H), 2.25-2.45 (m, 1H), 2.73 (s, 6H), 2.70-2.76 (m, 1H), 3.00-3.80 (m, 10.3H), 3.95-4.05 (m, 0.7H), 4.20-4.30 (m, 0.7H), 4.70-4.80 (m, 0.3H), 6.58 (d, J = 2.4 Hz, 0.3H), 6.63 (dd, J = 2.4, 8.3 Hz, 0.3H), 6.72 (dd, J = 2.4, 8.3 Hz, 0.7H), 6.79 (d, J = 2.4 Hz, 0.7H), 7.03 (d, J = 8.3 Hz, 0.3H), 7.11 (d, J = 8.3 Hz, 0.7H), 7.35-7.55 (m, 5H). | a |
| Example 17 | 46 | | (Free base, CDCl$_3$) δ 0.75-1.35 (m, 5H), 1.35-1.98 (m, 8H), 2.06-2.40 (m, 3H), 2.40-2.60 (m, 1H), 2.78-3.10 (m, 7H), 3.15-3.37 (m, 2H), 3.45-3.70 (m, 1.6H), 4.08-4.25 (m, 0.8H), 4.70-4.82 (m, 0.6H), 644 (d, J = 2.4 Hz, 0.4H), 6.52 (dd, J = 2.4, 8.3 Hz, 0.4H), 6.59 (dd, J = 2.4, 8.3 Hz, 0.6H), 6.65 (d, J = 2.4 Hz, 0.6H), 6.88 (d, J = 8.3 Hz, 0.4H), 6.92 (d, J = 8.3 Hz, 0.6H), 720-7.50 (m, 5H). | a |
| Example 18 | 47 | | (Dimesilate, CD$_3$OD) δ 0.75-1.25 (m, 1.3H), 1.40-2.10 (m, 10.7H), 2.25-2.40 (m, 1H), 2.73 (s, 6H), 2.70-2.90 (m, 1H), 3.00-4.00 (m, 14H), 4.20-4.30 (m, 0.7H), 4.70-4.80 (m, 0.3H), 6.50-6.85 (m, 2H), 7.00-7.20 (m, 1H), 7.35-7.50 (m, 5H). | a |
| Example 19 | 48 | | (Dimesilate, CD$_3$OD) δ 0.75-1.25 (m, 1.3H), 1.40-2.10 (m, 10.7H), 2.20-2.30 (m, 1H), 2.73 (s, 6H), 2.70-3.90 (m, 14H), 3.90-4.10 (m, 1H), 4.15-4.30 (m, 0.7H), 4.65-4.80 (m, 0.3H), 6.50-6.85 (m, 2H), 7.00-7.20 (m, 1H), 7.35-7.50 (m, 5H). | a |
| Example 20 | 49 | | (Dimesilate, CD$_3$OD) δ 0.75-1.25 (m, 1.3H), 1.40-2.00 (m, 4.7H), 2.10-2.25 (m, 1H), 2.72 (s, 6H), 2.70-3.00 (m, 3H), 3.10-3.85 (m, 10H), 4.00-4.15 (m, 2H), 4.15-4.30 (m, 2.7H), 4.65-4.80 (m, 0.3H), 6.57 (d, J = 2.4 Hz, 0.3H), 6.65 (dd, J = 2.4, 8.3 Hz, 0.3H), 6.74 (dd, J = 2.4, 8.3 Hz, 0.7H), 6.78 (d, J = 2.4 Hz, 0.7H), 7.06 (d, J = 8.3 Hz, 0.3H), 7.14 (d, J = 8.3 Hz, 0.7H), 7.35-7.50 (m, 5H). | a |
| Example 21 | 50 | | (Dihydrochloride, CD$_3$OD) δ 0.75-1.25 (m, 5.7H), 1.40-2.10 (m, 5.7H), 2.15-2.45 (m, 2H), 2.75-3.00 (m, 2H), 3.00-3.80 (m, 14H), 3.90-4.05 (m, 1H), 4.20-4.30 (m, 0.7H), 4.70-4.80 (m, 0.3H), 6.58 (d, J = 2.4 Hz, 0.3H), 6.65 (dd, J = 2.4, 8.3 Hz, 0.3H), 6.74 (dd, J = 2.4, 8.3 Hz, 0.7H), 6.79 (d, J = 2.4 Hz, 0.7H), 7.06 (d, J = 8.3 Hz, 0.3H), 7.14 (d, J = 8.3 Hz, 0.7H), 7.35-7.50 (m, 5H). | a |

TABLE 3

| Compound No. | Structural formula | ¹H NMR | Synthesis method |
|---|---|---|---|
| Example 22 — 51 | | (Dihydrochloride, CD$_3$OD) δ 0.75-1.25 (m, 1.3H), 1.45-2.00 (m, 5.7H), 2.15-2.30 (m, 1H), 2.30-2.45 (m, 1H), 2.70-3.00 (m, 2H), 3.10-3.80 (m, 14H), 3.90-4.05 (m, 1H), 4.20-4.30 (m, 0.7H), 4.70-4.80 (m, 0.3H), 6.58 (d, J = 2.4 Hz, 0.3H), 6.65 (dd, J = 2.4, 8.3 Hz, 0.3H), 6.74 (dd, J = 2.4, 8.3 Hz, 0.7H), 6.78 (d, J = 2.4 Hz, 0.7H), 7.06 (d, J = 8.3 Hz, 0.3H), 7.14 (d, J = 8.3 Hz, 0.7H), 7.35-7.50 (m, 5H). | a |
| Example 23 — 52 | | (Dimesilate, CD$_3$OD) δ 0.75-1.25 (m, 1.3H), 1.35-2.10 (m, 7.7H), 2.10-2.60 (m, 3H), 2.71 (s, 6H), 2.70-3.05 (m, 5H), 3.10-3.85 (m, 9H), 3.90-4.10 (m, 2H), 4.20-4.30 (m, 0.7H), 4.70-4.80 (m, 0.3H), 6.58 (d, J = 2.4 Hz, 0.3H), 6.64 (dd, J = 2.4, (8.3 Hz, 0.3H), 6.74 (dd, J = 2.4, 8.3 Hz, 0.7H), 6.78 (d, J = 2.4 Hz, 0.7H), 7.06 (d, J = 8.3 Hz, 0.3H), 7.14 (d, J = 8.3 Hz, 0.7H), 7.35-7.50 (m, 5H). | a |
| Example 24 — 53 | | (Dimesilate, CD$_3$OD) δ 0.75-1.25 (m, 1.3H), 1.40-2.45 (m, 11.7H), 2.72 (s, 6H), 2.60-3.00 (m, 3H), 3.10-3.80 (m, 10.7H), 3.85-4.00 (m, 1.3H), 4.15-4.30 (m, 0.7H), 4.65-4.85 (m, 0.3H), 6.58 (d, J = 2.4 Hz, 0.3H), 6.65 (dd, J = 2.4, 8.3 Hz, 0.3H), 6.74 (dd, J = 2.4, 8.3 Hz, 0.7H), 6.79 (d, J = 2.4 Hz, 0.7H), 7.06 (d, J = 8.3 Hz, 0.3H), 7.14 (d, J = 8.3 Hz, 0.7H), 7.35-7.50 (m, 5H). | a |

TABLE 3-continued

| Compound No. | | Structural formula | $^1$H NMR | Synthesis method |
|---|---|---|---|---|
| Example 25 | 54 | | (Dimesilate, CD$_3$OD) δ 0.75-1.25 (m, 1.3H), 1.45-1.85 (m, 4.7H), 1.85-2.10 (m, 3.6H), 2.10-2.30 (m, 2.4H), 2.68-2.72 (m, 0.7H), 2.70 (s, 6H), 2.80-2.95 (m, 2.3H), 3.00-3.15 (m, 3H), 3.15-3.55 (m, 7H), 3.60-3.70 (m, 1.3H), 3.70-3.80 (m, 0.7H), 3.90-4.05 (m, 1H), 4.20-4.30 (m, 0.7H), 4.70-4.80 (m, 0.3H), 6.58 (d, J = 2.4 Hz, 0.3H), 6.65 (dd, J = 2.4, 8.3 Hz, 0.3H), 6.74 (dd, J = 2.4, 8.3 Hz, 0.7H), 6.79 (d, J = 2.4, 8.3 Hz, 0.7H), 7.06 (d, J = 8.3 Hz, 0.3H), 7.14 (d, J = 8.3 Hz, 0.7H), 7.35-7.50 (m, 5H). | a |
| Example 26 | 55 | | (Dihydrochloride, CD$_3$OD) δ 0.80-1.15 (m, 1H), 1.35-1.90 (m, 4H), 1.95-2.29 (m, 4H), 2.68-2.89 (m, 1H), 3.00-3.61 (m, 13.4H), 3.74-3.86 (m, 0.3H), 3.91 (d, J = 6.3 Hz, 0.3H), 3.96 (d, J = 6.3 Hz, 0.7H), 4.29-4.42 (m, 0.3H), 6.30-6.50 (m, 0.3H), 6.56 (dd, J = 2.4, 8.3 Hz, 0.3H), 6.76 (dd, J = 2.4, 8.3 Hz, 0.7H), 6.83 (d, J = 2.4 Hz, 0.7H), 6.99 (d, J = 8.3 Hz, 0.3H), 7.16 (d, J = 8.3 Hz, 0.7H), 7.40-7.65 (m, 4H), 7.72-7.81 (m, 1H), 7.90-8.00 (m, 2H). | c |
| Example 27 | 56 | | (Dihydrochloride, CD$_3$OD) δ 0.77-1.08 (m, 1H), 1.45-1.74 (m, 4H), 1.82-1.94 (m, 1H), 2.08-2.30 (m, 3H), 2.76-2.88 (m, 1H), 3.06 (t, J = 7.3 Hz, 2H), 3.10-3.67 (m, 8H), 3.72-3.93 (m, 4H), 3.96 (d, J = 6.3 Hz, 1H), 4.05-4.23 (m, 1H), 4.56-4.64 (m, 0.2H), 4.66-4.75 (m, 0.8H), 6.63 (s, 0.2H), 6.79 (d, J = 1.0 Hz, 0.8H), 6.84-6.94 (m, 2H), 7.22 (d, J = 8.3 Hz, 1H), 7.54 (s, 0.2H), 7.57 (s, 0.8H), 7.82 (s, 0.2H), 8.04 (s, 0.8H). | e |

TABLE 4

| Compound No. | | Structural formula | $^1$H NMR | Synthesis method |
|---|---|---|---|---|
| Example 28 | 57 | | (Dimesilate, CD$_3$OD) δ 0.78-1.08 (m, 1H), 1.13-1.23 (m, 0.3H), 1.47-1.96 (m, 4.7H), 2.00-2.40 (m, 7H), 2.71 (s, 6H), 2.74-3.00 (m, 2H), 3.06-3.58 (m, 11H), 3.61-3.81 (m, 4H), 3.94 (dd, J = 6.3, 12.2 Hz, 1H), 4.19-4.31 (m, 0.7H), 4.70-4.77 (m, 0.3H), 6.58 (d, J = 2.4 Hz, 0.3H), 6.65 (dd, J = 2.4, 8.3 Hz, 0.3H), 6.74 (dd, J = 2.4, 8.3 Hz, 0.7H), 6.79 (d, J = 2.4 Hz, 0.7H), 7.06 (d, J = 8.3 Hz, 0.3H), 7.14 (d, J = 8.3 Hz, 0.7H), 7.36-7.53 (m, 5H). | f |

Synthesis Methods Mentioned in Tables 1 to 4
Method a: Method described in Example 3
Method b: Method described in Examples 3 and 4
Method c: Method described in Examples 1 and 2
Method d: Combination of synthesis methods described in Examples 1 and 3
Method e: Method described in Example 1
Method f: Method described in Example 6

Example 29

Synthesis of [(1S,3aR,5aS,6R,11bR,11cS)-10-hydroxy-14-[3-(methylamino)propyl]-1,2,3a,4,5,6,7,11c-octahydro-3H-6,11b-(epiminoethano)-1,5a-methanonaphtho[1,2-e]indol-3-yl](phenyl)methanone (59)

(1) [(1S,3aR,5aS,6R,11bR,11cS)-10-[(t-Butyldimethylsilyl)oxy]-14-(3-hydroxypropyl)-1,2,3a,4,5,6,7,11c-octahydro-3H-6,11b-(epiminoethano)-1,5a-methanonaphtho[1,2-e]indol-3-yl](phenyl)methanone

[Formula 58]

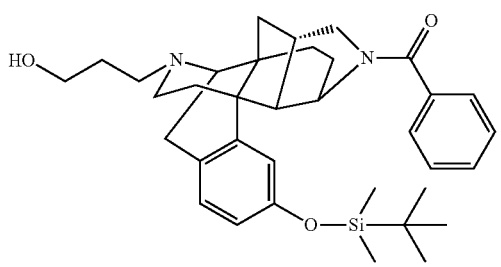

58

Under an argon atmosphere, a solution of the compound 16 (70 mg, 0.14 mmol) in acetonitrile (3 mL) was added with 3-bromo-1-propanol (35.7 μg, 0.41 mmol), potassium carbonate (56.4 mg, 0.41 mmol), and potassium iodide (112.9 mg, 0.568 mmol), and the mixture was refluxed for 20 hours. The reaction mixture was poured into saturated aqueous sodium hydrogencarbonate, and the mixture was extracted three times with chloroform. The organic layers were combined, dried over anhydrous sodium sulfate, and concentrated. The resulting crude product was purified by silica gel column chromatography to give the title compound 58 (93.5 mg, quantitative).

(2) [(1S,3aR,5aS,6R,11bR,11cS)-10-Hydroxy-14-[3-(methylamino)propyl]-1,2,3a,4,5,6,7,11c-octahydro-3H-6,11b-(epiminoethano)-1,5a-methanonaphtho[1,2-e]indol-3-yl](phenyl)methanone

[Formula 59]

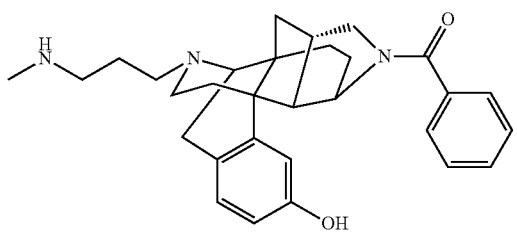

59

Under an argon atmosphere, a solution of the compound 58 (36.5 mg, 0.064 mmol) in dichloromethane (1 mL) was added with triethylamine (26.6 μL, 0.19 mmol), and methanesulfonyl chloride (10 μL, 0.13 mmol), and the mixture was stirred for 2 hours. The reaction mixture was poured into saturated aqueous sodium hydrogencarbonate, and the mixture was extracted three times with chloroform. The organic layers were combined, dried over anhydrous sodium sulfate, and concentrated. The resulting crude product was dissolved in methanol (5 mL), the solution was added with potassium iodide (105.8 mL, 0.64 mmol), and a 2 M solution of methylamine in methanol (15 mL), and the mixture was stirred at 100° C. for 2 hours in a sealed tube. The reaction mixture was concentrated under reduced pressure, and then the mixture was added with saturated aqueous sodium hydrogencarbonate, and the mixture was extracted three times with chloroform. The organic layers were combined, dried over anhydrous sodium sulfate, and concentrated. The resulting crude product was purified by silica gel column chromatography and preparative TLC to give the title compound 59 (14.3 mg, 38%).

Compound 23 (dihydrochloride)$^1$H NMR (CD$_3$OD, 400 MHz): δ 0.80-1.30 (m, 1.4H), 1.45-2.00 (m, 4.6H), 2.10-2.30 (m, 3H), 2.75 (s, 3H), 2.80-2.90 (m, 1H), 3.05-3.55 (m, 10.4H), 3.65 (d, J=12.7 Hz, 1H), 3.70-3.80 (m, 0.6H), 3.90-4.00 (m, 1H), 4.20-4.30 (m, 0.6H), 4.75-4.80 (m, 0.4H), 6.58 (d, J=2.4 Hz, 0.4H), 6.65 (dd, J=2.4, 8.8 Hz, 0.4H), 6.74 (dd, J=2.4, 8.3 Hz, 0.6H), 6.79 (d, J=2.4 Hz, 0.6H), 7.05 (d, J=8.8 Hz, 0.4H), 7.14 (d, J=8.3 Hz, 0.6H), 7.36-7.48 (m, 5H)

Example 30

Synthesis of [(1S,3aR,5aS,6R,11bR,11cS)-14-[3-(dimethylamino)propyl]-10-hydroxy-1,2,3a,4,5,6,7,11c-octahydro-3H-6,11b-(epiminoethano)-1,5a-methanonaphtho[1,2-e]indol-3-yl](phenyl)methanone (60)

[Formula 60]

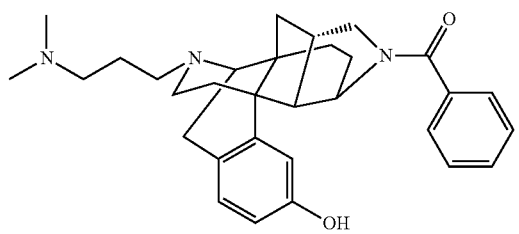

60

According to the method described in Example 29, (2), the title compound 60 (27.7 mg) was obtained by using the compound 58 (49.2 mg).

Compound 60 (dihydrochloride)$^1$H NMR (CD$_3$OD, 400 MHz): δ 0.80-1.35 (m, 1.3H), 1.50-2.00 (m, 4.7H), 2.15-2.40 (m, 3H), 2.70-2.90 (m, 1H), 2.94 (s, 6H), 3.10-3.30 (m, 8.3H), 3.35-3.55 (m, 2H), 3.65 (d, J=11.7 Hz, 1H), 3.70-3.80 (m, 0.7H), 3.94-4.02 (m, 1H), 4.20-4.30 (m, 0.7H), 4.70-4.90 (m, 0.3H), 6.58 (d, J=2.4 Hz, 0.3H), 6.65 (dd, J=2.4, 8.3 Hz, 0.3H), 6.74 (dd, J=2.4, 8.3 Hz, 0.7H), 6.78 (d, J=2.4 Hz, 0.7H), 7.06 (d, J=8.3 Hz, 0.3H), 7.14 (d, J=8.3 Hz, 0.7H), 7.37-7.50 (m, 5H)

Example 31

Synthesis of [(1S,3aR,5aS,6R,11bR,11cS)-14-(3-amino-2-hydroxypropyl)-10-hydroxy-1,2,3a, 4,5,6,7,11c-octahydro-3H-6,11b-(epiminoethano)-1,5a-methanonaphtho[1,2-e]indol-3-yl](phenyl)methanone (62)

(1) t-Butyl[3-[(1S,3aR,5aS,6R,11bR,11cS)-3-benzoyl-10-[(t-butyldimethylsilyl)oxy]-2, 3,3a,4,5,6,7,11c-octahydro-1H-6,11b-(epiminoethano)-1,5a-methanonaphtho[1,2-e]indol-14-yl]-2-hydroxypropyl]carbamate

[Formula 61]

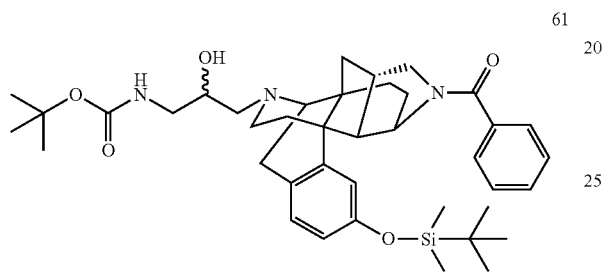

61

Under an argon atmosphere, a solution of the compound 16 (60 mg, 0.12 mmol) in methanol (1 mL) was added with t-butyl N-(2-oxiranylmethyl)carbamate (30 mg, 0.18 mmol), and the mixture was stirred at 65° C. for 16 hours. The reaction mixture was cooled to room temperature, and then concentrated, and the residue was purified by preparative TLC to give one diastereomer of the title compound (61a, 34 mg, 42%) and the other diastereomer of the title compound (61b, 26 mg, 32%).

(2) [(1S,3aR,5aS,6R,11bR,11cS)-14-(3-Amino-2-hydroxypropyl)-10-hydroxy-1,2,3a,4,5,6,7,11c-octahydro-3H-6,11b-(epiminoethano)-1,5a-methanonaphtho[1,2-e]indol-3-yl](phenyl)methanone

[Formula 62]

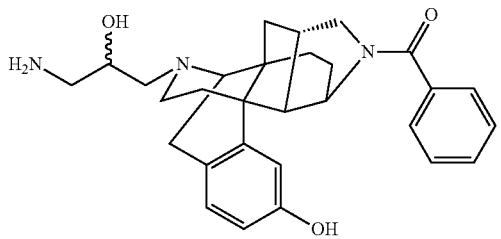

62

According to the methods described in Example 2, (5) and Example 1, (4), the compounds 61a (34 mg) and 61b (26 mg) were desilylated and debutoxycarbonylated to give the title compounds 62a (13 mg) and 62b (13 mg), respectively.

Compound 62a (dihydrochloride)¹H NMR (CD₃ OD, 400 MHz): δ 0.78-1.22 (m, 1.3H), 1.44-1.98 (m, 4.7H), 2.18-2.38 (m, 1H), 2.78-3.02 (m, 2H), 3.07-3.58 (m, 9H), 3.58-3.70 (m, 1.3H), 3.70-3.81 (m, 0.7H), 4.06-4.18 (m, 1H), 4.18-4.31 (m, 0.7H), 4.35-4.47 (m, 1H), 4.68-4.75 (m, 0.3H), 6.58 (d, J=2.4 Hz, 0.3H), 6.65 (dd, J=2.4, 8.3 Hz, 0.3H), 6.74 (dd, J=2.4, 8.3 Hz, 0.7H), 6.80 (d, J=2.4 Hz, 0.7H), 7.06 (d, J=8.3 Hz, 0.3H), 7.14 (d, J=8.3 Hz, 0.7H), 7.32-7.51 (m, 5H)

Compound 62b (dihydrochloride)¹H NMR (CD₃ OD, 400 MHz): δ 0.78-1.30 (m, 1.3H), 1.42-2.00 (m, 4.7H), 2.05-2.15 (m, 1H), 2.83-3.02 (m, 3H), 3.11-3.83 (m, 10H), 3.92-4.07 (m, 1H), 4.20-4.41 (m, 1.7H), 4.70-4.78 (m, 0.3H), 6.59 (d, J=2.4 Hz, 0.3H), 6.65 (dd, J=2.4, 8.3 Hz, 0.3H), 6.75 (dd, J=2.4, 8.3 Hz, 0.7H), 6.80 (d, J=2.4 Hz, 0.7H), 7.06 (d, J=8.3 Hz, 0.3H), 7.14 (d, J=8.3 Hz, 0.7H), 7.32-7.51 (m, 5H)

Example 32

Synthesis of [(1S,3aR,5aS,6R,11bR,11cS)-14-[(2R)-2-amino-3-hydroxypropyl]-10-hydroxy-1,2, 3a,4,5,6,7,11c-octahydro-3H-6,11b-(epiminoethano)-1,5a-methanonaphtho[1,2-e]indol-3-yl](phenyl)methanone (64)

(1) t-Butyl (4R)-4-[[(1S,3aR,5aS,6R,11bR,11cS)-3-benzoyl-10-[(t-butyldimethylsilyl)oxy]-2,3, 3a,4,5,6,7,11c-octahydro-1H-6,11b-(epiminoethano)-1,5a-methanonaphtho[1,2-e]indol-14-yl]methyl]-2,2-dimethyloxazolidine-3-carboxylate

[Formula 63]

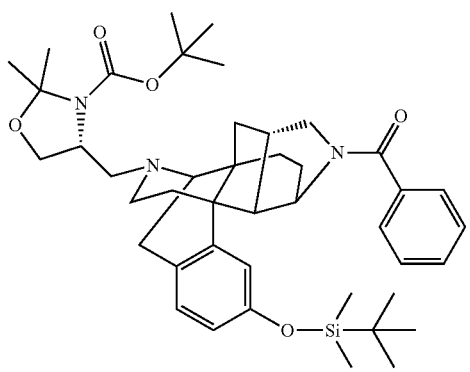

63

Under an argon atmosphere, a solution of the compound 16 (30 mg, 0.058 mmol) in dichloromethane (1 mL) was added with (S)-(−)-3-Boc-2,2-dimethyloxazolidine-4-carboxaldehyde (40 mg, 0.17 mmol), and sodium triacetoxyborohydride (37 mg, 0.17 mmol), and the mixture was stirred at room temperature for 16 hours. The reaction mixture was added with 6% aqueous ammonia, and the resulting mixture was stirred at room temperature for 1 hour, and then extracted three times with chloroform. The organic layers were combined, washed with saturated brine, dried over anhydrous sodium sulfate, and concentrated.

The residue was purified by silica gel column chromatography to give the title compound 63 (43 mg, 100%).

(2) [(1S,3aR,5aS,6R,11bR,11cS)-14-[(2R)-2-Amino-3-hydroxypropyl]-10-hydroxy-1,2,3a,4,5,6,7,11c-octahydro-3H-6,11b-(epiminoethano)-1,5a-methanonaphtho[1,2-e]indol-3-yl](phenyl)methanone

[Formula 65]

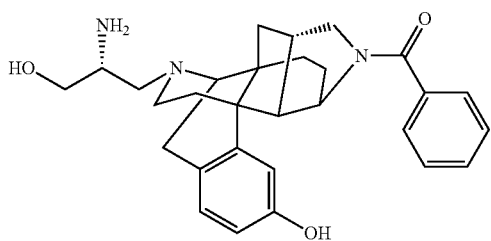

64

According to the method described in Example 1, (4), the compound 63 (43 mg) was de-butoxycarbonylated. Then, the resulting product was dissolved in methanol (1 mL), the solution was added with 3 M hydrochloric acid (1 mL), and the mixture was stirred at room temperature for 2 hours. The reaction mixture was made basic with aqueous potassium carbonate, and extracted three times with chloroform. The organic layers were combined, washed with saturated brine, dried over anhydrous sodium sulfate, and concentrated. The resulting residue was purified by preparative TLC to give the title compound 64 (3.3 mg).

Compound 64 (dihydrochloride)$^1$H NMR (CD$_3$ OD, 400 MHz): δ 0.76-1.24 (m, 1.3H), 1.42-2.10 (m, 4.7H), 2.16-2.36 (m, 1H), 2.65-2.96 (m, 1H), 3.05-3.80 (m, 9.7H), 3.80-4.18 (m, 4.3H), 4.18-4.32 (m, 0.7H), 4.70-4.77 (m, 0.3H), 6.58 (d, J=2.4 Hz, 0.3H), 6.65 (dd, J=2.4, 8.3 Hz, 0.3H), 6.74 (dd, J=2.4, 8.3 Hz, 0.7H), 6.79 (d, J=2.4 Hz, 0.7H), 7.06 (d, J=8.3 Hz, 0.3H), 7.14 (d, J=8.3 Hz, 0.7H), 7.35-7.48 (m, 5H)

Example 33

Synthesis of [(1S,3aR,5aS,6R,11bR,11cS)-14-[(2S)-2-amino-3-hydroxypropyl]-10-hydroxy-1,2,3a,4,5,6,7,11c-octahydro-3H-6,11b-(epiminoethano)-1,5a-methanonaphtho[1,2-e]indol-3-yl](phenyl)methanone (65)

[Formula 66]

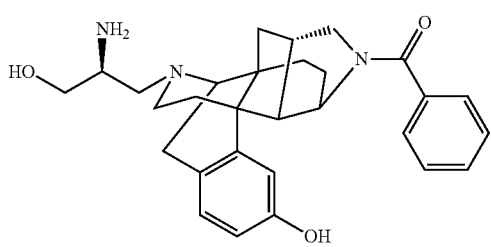

65

According to the method described in Example 32, the title compound 65 (13 mg) was obtained by using the compound 16 (30 mg), and (R)-(+)-3-Boc-2,2-dimethyloxazolidine-4-carboxaldehyde (40 mg).

Compound 65 (dihydrochloride)$^1$H NMR (CD$_3$ OD, 400 MHz): δ 0.74-1.22 (m, 1.3H), 1.45-1.98 (m, 4.7H), 2.15-2.31 (m, 1H), 2.76-3.00 (m, 1H), 3.07-3.58 (m, 6.3H), 3.58-4.15 (m, 7.7H), 4.15-4.30 (m, 0.7H), 4.68-4.78 (m, 0.3H), 6.58 (d, J=2.4 Hz, 0.3H), 6.65 (dd, J=2.4, 8.8 Hz, 0.3H), 6.74 (dd, J=2.4, 8.3 Hz, 0.7H), 6.79 (d, J=2.4 Hz, 0.7H), 7.06 (d, J=8.8 Hz, 0.3H), 7.14 (d, J=8.3 Hz, 0.7H), 7.32-7.50 (m, 5H)

Example 34

Synthesis of (1S,3aR,5aS,6R,11bR,11cS)-3-(4,6-dimethylpyrimidin-2-yl)-14-[2-(methylamino)ethyl]-2,3,3a,4,5,6,7,11c-octahydro-1H-6,11b-(epiminoethano)-1,5a-methanonaphtho[1,2-e]indol-10-ol (73)

(1) 2,2,2-Trichloroethyl (1S,3aR,5aS,6R,11bR,11cS)-10-methoxy-1,2,3a,4,5,6,7,11c-octahydro-3H-6,11b-(epiminoethano)-1,5a-methanonaphtho[1,2-e]indole-3-carboxylate

[Formula 67]

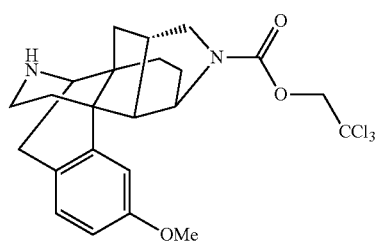

66

According to the method described in Example 1, (2), the title compound 66 was obtained by using the compound 24.

1H NMR (CDCl$_3$, 400 MHz): δ 0.70-0.90 (m, 1H), 1.30-1.60 (m, 4H), 1.60-1.80 (m, 1H), 1.95-2.10 (m, 1H), 2.75-2.85 (m, 1H), 3.00-3.30 (m, 5H), 3.50-3.85 (m, 4H), 3.78 (s, 1.5H), 3.80 (s, 1.5H), 4.25-4.40 (m, 1H), 4.57 (d, J=12.0 Hz, 0.5H), 4.65 (d, J=12.0 Hz, 0.5H), 4.79 (d, J=12.0 Hz, 0.5H), 4.87 (d, J=12.0 Hz, 0.5H), 6.65-6.73 (m, 1H), 6.73-6.85 (m, 1H), 7.11 (d, J=8.3 Hz, 0.5H), 7.12 (d, J=8.3 Hz, 0.5H)

(2) 2,2,2-Trichloroethyl (1S,3aR,5aS,6R,11bR,11cS)-14-t-butoxycarbonyl-10-methoxy-1,2,3a,4,5,6,7,11c-octahydro-3H-6,11b-(epiminoethano)-1,5a-methanonaphtho[1,2-e]indole-3-carboxylate

[Formula 68]

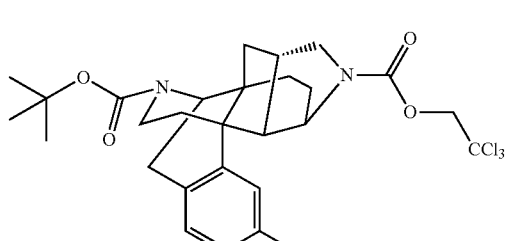

67

Under an argon atmosphere, a solution of the compound 66 (60 mg, 0.123 mmol) in dichloromethane (1 mL) was added with triethylamine (51 μL, 0.35 mmol), and di-t-butyl dicarbonate (42 μL, 0.19 mmol), and the mixture was stirred at room temperature for 16 hours. The reaction mixture was concentrated, the resulting residue was dissolved in ethyl acetate, and the solution was washed with saturated aqueous sodium hydrogencarbonate, water, and saturated brine. The organic layer was dried over anhydrous sodium sulfate, and then concentrated. The resulting crude product was purified by silica gel column chromatography to give the title compound 67 (72 mg, 100%).

$^1$H NMR (CDCl$_3$, 400 MHz): δ 0.70-0.95 (m, 1H), 1.08-1.50 (m, 13H), 1.60-1.86 (m, 2H), 2.45-2.57 (m, 1H), 2.58-2.83 (m, 2H), 2.96-3.08 (m, 2H), 3.43-3.60 (m, 2H), 3.75-3.85 (m, 4.5H), 3.90-4.00 (m, 0.5H), 4.26-4.37 (m, 1.5H), 4.50-4.90 (m, 2.5H), 6.65-6.76 (m, 2H), 7.02-7.08 (m, 1H)

(3) t-Butyl (1S,3aR,5aS,6R,11bR,11cS)-10-methoxy-2, 3,3a,4,5,6,7,11c-octahydro-1H-6,11b-(epiminoethano)-1,5a-methanonaphtho[1,2-e]indole-14-carboxylate

[Formula 69]

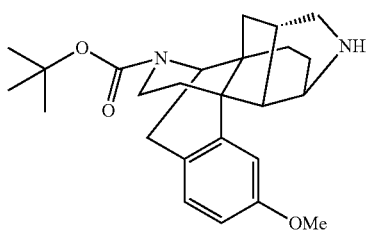

68

According to the method described in Example 7, (6), the title compound 68 (49 mg) was obtained by using the compound 67 (72 mg).

$^1$H NMR (DMSO-d$_6$, 400 MHz): δ 0.82-0.98 (m, 1H), 1.02-1.12 (m, 1H), 1.15-1.30 (m, 2H), 1.32-1.60 (m, 11H), 1.65-1.80 (m, 1H), 2.10-2.22 (m, 1H), 2.50-2.70 (m, 2H), 2.84-3.04 (m, 4H), 3.10-3.90 (m, 3H), 3.73 (s, 3H), 4.22 (d, J=6.3 Hz, 1H), 4.31 (d, J=5.9 Hz, 1H), 6.72-6.77 (m, 2H), 7.07 (d, J=9.3 Hz, 1H)

(4) t-Butyl (1S,3aR,5aS,6R,11bR,11cS)-3-(4,6-dimethylpyrimidin-2-yl)-10-methoxy-2,3, 3a,4,5,6,7,11c-octahydro-1H-6,11b-(epiminoethano)-1,5a-methanonaphtho[1,2-e]indole-14-carboxylate

[Formula 70]

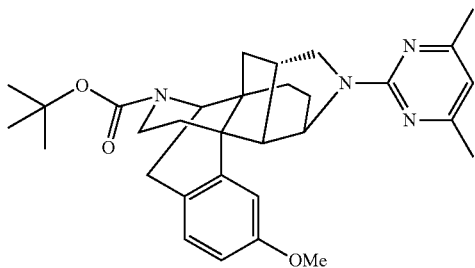

69

According to the method described in Example 8, (1), the title compound 69 (70 mg) was obtained by using the compound 68 (60 mg).

$^1$H NMR (CDCl$_3$, 400 MHz): δ 0.75-0.95 (m, 1H), 1.08-1.23 (m, 1H), 1.23-1.72 (m, 13H), 1.80-1.96 (m, 1H), 2.25 (br s, 6H), 2.48-2.56 (m, 1H), 2.60-2.85 (m, 2H), 3.00-3.15 (m, 2H), 3.40-3.60 (m, 1H), 3.65 (d, J=11.7 Hz, 1H), 3.75-4.05 (m, 2H), 3.82 (s, 3H), 4.33 (d, J=6.3 Hz, 0.5H), 4.52 (d, J=6.3 Hz, 0.5H), 4.56-4.67 (m, 1H), 6.21 (s, 1H), 6.72 (dd, J=2.4, 8.3 Hz, 1H), 6.77 (d, J=2.4 Hz, 1H), 7.05 (d, J=8.3 Hz, 1H)

(5) (1S,3aR,5aS,6R,11bR,11cS)-3-(4,6-Dimethylpyrimidin-2-yl)-10-methoxy-2,3,3a,4,5,6,7,11c-octahydro-1H-6,11b-(epiminoethano)-1,5a-methanonaphtho[1,2-e]indole

[Formula 71]

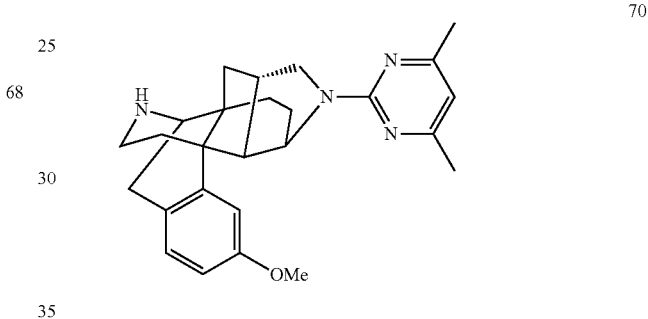

70

According to the method described in Example 1, (4), the title compound 70 (56 mg) was obtained by using compound 69 (70 mg).

(6) (1S,3aR,5aS,6R,11bR,11cS)-3-(4,6-Dimethylpyrimidin-2-yl)-2,3,3a,4,5,6,7,11c-octahydro-1H-6, 11b-(epiminoethano)-1,5a-methanonaphtho[1,2-e]indol-10-ol

[Formula 72]

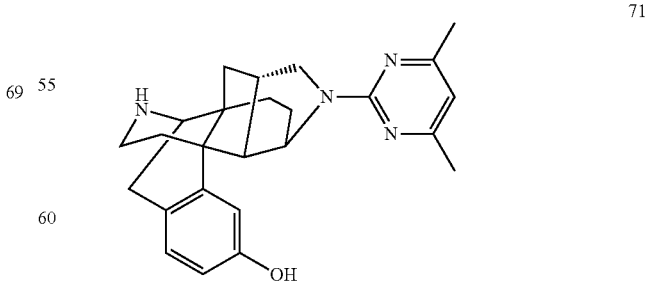

71

According to the method described in Example 2, the title compound 71 (50 mg) was obtained by using the compound 70 (56 mg).

(7) t-Butyl[2-[(1S,3aR,5aS,6R,11bR,11cS)-3-(4,6-dimethylpyrimidin-2-yl)-10-hydroxy-2,3,3a,4,5,6,7,11c-octahydro-1H-6,11b-(epiminoethano)-1,5a-methanonaphtho[1,2-e]indol-14-yl]ethyl](methyl)carbamate

[Formula 73]

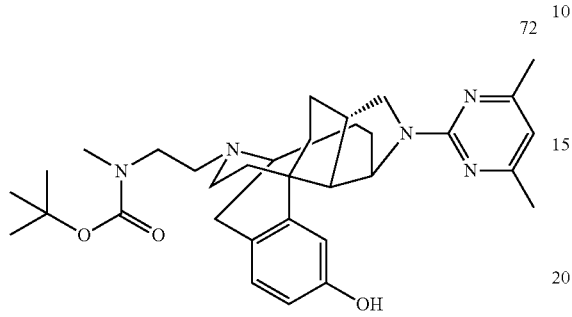

According to the method described in Example 3, (4), the title compound 72 (69 mg) was obtained by using the compound 71 (50 mg), and 2-(N-Boc-N-methylamino)acetaldehyde (64 mg).

(8) (1S,3aR,5aS,6R,11bR,11cS)-3-(4,6-Dimethylpyrimidin-2-yl)-14-[2-(methylamino)ethyl]-2,3,3a,4,5,6,7,11c-octahydro-1H-6,11b-(epiminoethano)-1,5a-methanonaphtho[1,2-e]indol-10-ol

[Formula 74]

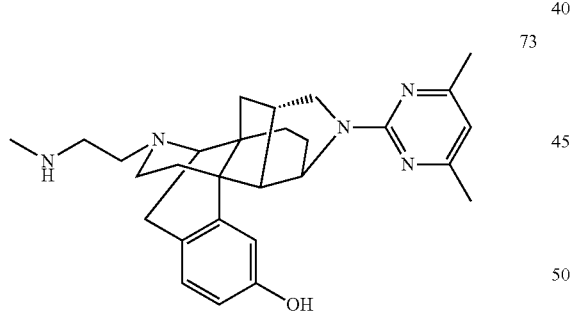

According to the method described in Example 1, (4), the title compound 73 (28 mg) was obtained by using the compound 72 (69 mg).

Compound 73 (free base) $^1$H NMR (CDCl$_3$, 400 MHz): δ 0.75-0.92 (m, 1H), 1.10-1.30 (m, 2H), 1.32-1.53 (m, 2H), 1.55-1.70 (m, 1H), 1.85-2.00 (m, 1H), 2.05-2.17 (m, 1H), 2.24 (br s, 6H), 2.38-2.56 (m, 2H), 2.51 (s, 3H), 2.60-2.80 (m, 3H), 2.80-3.10 (m, 6H), 3.24 (t, J=11.7 Hz, 1H), 3.64 (d, J=11.2 Hz, 1H), 3.87 (dd, J=7.8, 11.7 Hz, 1H), 4.61 (dd, J=5.4, 7.8 Hz, 1H), 6.21 (s, 1H), 6.57 (dd, J=2.4, 8.3 Hz, 1H), 6.66 (d, J=2.4 Hz, 1H), 6.92 (d, J=8.3 Hz, 1H)

Example 35

Synthesis of (1S,3aR,5aS,6R,11bR,11cS)-14-[2-(dimethylamino)ethyl]-3-(4,6-dimethylpyrimidin-2-yl)-2,3,3a,4,5,6,7,11c-octahydro-1H-6,11b-(epiminoethano)-1,5a-methanonaphtho[1,2-e]indol-10-ol (74)

[Formula 75]

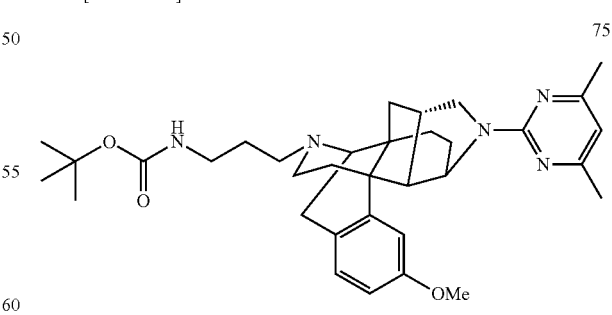

According to the method described in Example 4, the title compound 74 (13 mg) was obtained by using the compound 73 (18 mg).

Compound 74 (trihydrochloride) $^1$H NMR (CD$_3$OD, 400 MHz): δ 0.80-1.10 (m, 1H), 1.38-1.74 (m, 4H), 1.82-1.96 (m, 1H), 2.20-2.38 (m, 1H), 2.45 (br s, 3H), 2.52 (br s, 3H), 2.76-2.98 (m, 1H), 3.01 (s, 6H), 3.30-3.93 (m, 12H), 3.93-4.15 (m, 2H), 6.73-6.82 (m, 3H), 7.16 (d, J=8.3 Hz, 1H)

Example 36

Synthesis of (1S,3aR,5aS,6R,11bR,11cS)-14-(3-aminopropyl)-3-(4,6-dimethylpyrimidin-2-yl)-2,3,3a,4,5,6,7,11c-octahydro-1H-6,11b-(epiminoethano)-1,5a-methanonaphtho[1,2-e]indol-10-ol (74)

(1) t-Butyl[3-[(1S,3aR,5aS,6R,11bR,11cS)-3-(4,6-dimethylpyrimidin-2-yl)-10-methoxy-2,3,3a,4,5,6,7,11c-octahydro-1H-6,11b-(epiminoethano)-1,5a-methanonaphtho[1,2-e]indol-14-yl]propyl]carbamate

[Formula 76]

According to the method described in Example 1, (3), the title compound 75 (31.3 mg, 27%) was obtained by using the compound 70 (84 mg, 0.20 mmol), and 3-(Boc-amino)propyl bromide (139.4 mg, 0.59 mmol).

$^1$H NMR (CDC$_3$, 400 MHz): δ 0.74-0.90 (m, 1H), 1.15-1.35 (m, 3H), 1.46 (s, 9H), 1.50-1.80 (m, 4H), 1.90-2.10 (m,

2H), 2.24 (br s, 6H), 2.45-2.60 (m, 3H), 2.90-3.00 (m, 3H), 3.05-3.35 (m, 5H), 3.66 (d, J=11.7 Hz, 1H), 3.81 (s, 3H), 3.86 (dd, J=7.8, 11.7 Hz, 1H), 4.55-4.62 (m, 1H), 5.83 (br s, 1H), 6.20 (s, 1H), 6.70 (dd, J=2.4, 8.3 Hz, 1H), 6.74 (d, J=2.4 Hz, 1H), 7.04 (d, J=8.3 Hz, 1H)

(2) (1S,3aR,5aS,6R,11bR,11cS)-14-(3-Aminopropyl)-3-(4,6-dimethylpyrimidin-2-yl)-2,3,3a,4,5,6,7,11c-octahydro-1H-6,11b-(epiminoethano)-1,5a-methanonaphtho[1,2-e]indol-10-ol

[Formula 77]

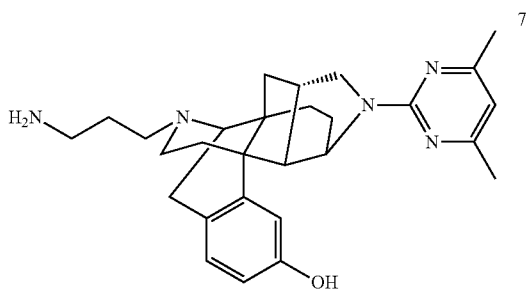

76

According to the methods described in Example 1, (4) and Example 2, the compound 76 (33.1 mg, 0.056 mmol) was debutoxycarbonylated and demethylated to give the title compound 76 (19.8 mg, 89%).

$^1$H NMR (CDCl$_3$, 400 MHz): δ 0.80-0.95 (m, 1H), 1.05-1.30 (m, 4H), 1.35-1.50 (m, 2H), 1.55-1.70 (m, 3H), 1.80-1.95 (m, 1H), 2.00-2.10 (m, 1H), 2.24 (br s, 6H), 2.40-2.50 (m, 3H), 2.81 (t, J=6.8 Hz, 2H), 2.85-2.90 (m, 2H), 2.93-3.10 (m, 2H), 3.24 (t, J=11.7 Hz, 1H), 3.64 (d, J=11.7 Hz, 1H), 3.86 (dd, J=7.8, 11.7 Hz, 1H), 4.60 (dd, J=5.4, 8.3 Hz, 1H), 6.20 (s, 1H), 6.56 (dd, J=2.4, 8.3 Hz, 1H), 6.65 (d, J=2.9 Hz, 1H), 6.90 (d, J=8.3 Hz, 1H)

Example 37

Opioid Receptor Function Test

Functional activities of the compounds of the present invention on the μ, δ, and κ opioid receptors were examined.
Methods:

The test was performed by using Lance Ultra cAMP Kit (Perkin-Elmer) according the prescribed method. In the evaluation of the agonistic activity, each human opioid receptor (δ, μ, and κ, accession numbers and catalog numbers are mentioned below)-expressing CHO cells and 10 μM of a test compound were reacted for 30 minutes in the presence of forskolin in an assay buffer (1×HBSS, 1 M HEPES, pH 7.4, 250 mM IBMX (isobutylmethylxanthine), 7.5% BSA). The cAMP detection reagent included in the kit was then added, and 1 hour afterward, time decomposition fluorometry was performed by using EnVision plate reader (Perkin-Elmer). The evaluation was performed with test compounds and control drugs (SNC 80 for δ, DAMGO for μ, U-69593 for κ) at a concentration in the range of $10^{-12}$ to $10^{-5}$ M, a dose effect graph for each test compound was obtained from fluorescence value at 665 nm, and EC$_{50}$ value and E$_{max}$ value were calculated. The E$_{max}$ value was calculated as a ratio of the maximum reaction of the test compound based on the maximum reaction of each control drug, which was taken as 100%.

SNC80:
(+)-4-[(αR)-α-(2S,5R)-4-Allyl-2,5-dimethyl-1-piperazinyl]-3-methoxybenzyl]-N,N-diethylbenzamide
DAMGO:
[D-Ala$^2$,N-MePhe$^4$,Gly-ol]enkephalin
U-69593:
(+)-(5α,7α,8β)-N-Methyl-N-[7-(1-pyrrolidinyl)-1-oxaspiro[4.5]dec-8-yl]benzeneacetamide
Accession Numbers and Catalog Numbers
δ: Catalog No. CT4607, accession No. NM_000911.2
μ: Catalog No. CT4605, accession No. NM_000914
κ: Catalog No. CT4606, accession No. NM_000912
(ChanTest Corporation)

TABLE 5

| | δ Receptor | | μ Receptor | | κ Receptor | |
|---|---|---|---|---|---|---|
| Compound | EC$_{50}$ value (nM) | E$_{max}$ (%) | EC$_{50}$ value (nM) | E$_{max}$ (%) | EC$_{50}$ value (nM) | E$_{max}$ (%) |
| Compound 13 Dihydrochloride (Example 2) | <10 | 101 | >100 | 39 | >100 | 12 |
| Compound 19 Dimesylate (Example 3) | <10 | 106 | >100 | 27 | N.C. | (2.6)$^a$ |
| Compound 20 Dimesylate (Example 4) | <1 | 103 | >100 | 54 | >10 | 17 |
| Compound 40 Dimesylate (Example 11) | <1 | 104 | >10 | 92 | >10 | 22 |
| Compound 41 Dihydrochloride (Example 12) | <1 | 103 | >100 | 97 | N.C. | (15)$^a$ |
| Compound 43 Dimesylate (Example 14) | <10 | 109 | N.C. | (8.2)$^a$ | N.C. | (7.2)$^a$ |
| Compound 49 Dimesylate (Example 20) | <1 | 108 | >100 | 105 | >100 | 28 |
| Compound 55 Dihydrochloride (Example 26) | <1 | 102 | >10 | 82 | N.C. | (4.8)$^a$ |

TABLE 5-continued

| Compound | δ Receptor | | μ Receptor | | κ Receptor | |
|---|---|---|---|---|---|---|
| | EC$_{50}$ value (nM) | E$_{max}$ (%) | EC$_{50}$ value (nM) | E$_{max}$ (%) | EC$_{50}$ value (nM) | E$_{max}$ (%) |
| Compound 62a Dihydrochloride (Example 31) | <1 | 108 | >100 | 106 | N.C. | (1.7)$^a$ |
| Compound 64 Dihydrochloride (Example 32) | <1 | 105 | N.C. | (60)$^a$ | N.C. | (9.0)$^a$ |
| Compound 74 Trihydrochloride (Example 35) | <1 | 101 | >10 | 121 | >100 | 46 |

N.C.: Because the maximum reaction was not attained at the maximum concentration (10 μM), EC$_{50}$ value was not calculated.
$^a$Because the maximum reaction was not attained at the maximum concentration, the reaction ratio at the maximum concentration is indicated as a reference value.

As shown in Table 5, it was confirmed that the compounds of the present invention had potent agonistic activity against the opioid δ receptor.

Example 38

Opioid Receptor Binding Test

Binding affinities of the compounds of the present invention to the μ, δ, and κ opioid receptors were examined.

Methods:

According to a previous report (J. Biol. Chem., 2001, 276:15409-15414), mouse cerebrum and guinea pig cerebellum membrane fractions were prepared. As radioactive ligands for the opioid receptors, [$^3$H]DAMGO (μ opioid receptor), [$^3$H]DPDPE (δ opioid receptor), and [3H]U69,593 (κ opioid receptor) were used. In the assays for the μ and δ receptors, the mouse cerebrum membrane fraction was used, and in the assay for the κ receptor, guinea pig cerebellum membrane fraction was used. For the nonspecific binding, DAMGO, DPDPE, and U69,593 were used at 1 μM for μ, δ and κ receptors, respectively. Each receptor membrane fraction, radioactive ligand, and a sample at various concentrations were reacted for a predetermined time, and after the B/F separation, amount of radioactivity remained on the filter was measured with a liquid scintillation counter, and binding inhibition ratio of the test compound (IC$_{50}$ value) was calculated. Ki value was calculated by using the resulting IC$_{50}$ value in accordance with the following equation.

$$Ki=IC_{50}/(1+L/Kd)$$

L: Concentration of radioactive ligand used
Kd: Kd value of radioactive ligand

Further, selectivity for the δ receptor among the opioid receptors was determined by calculating ratio of the Ki value for μ or κ, and the Ki value for δ (μ/δ or κ/δ).

DAMGO:
[D-Ala$^2$,N-MePhe$^4$, Gly-Ol]enkephalin
DPDPE:
[D-Pen$^2$,D-Pen$^5$]enkephalin

TABLE 6

| | Binding affinity (Ki, nM) | δ-receptor selectivity (Ki value ratio) | |
|---|---|---|---|
| Compound | δ | μ/δ | κ/δ |
| Compound 13 Dihydrochloride (Example 2) | <10 | >10 | >10 |
| Compound 43 Dimesylate (Example 14) | <1 | >10 | >10 |
| Compound 47 Dimesylate (Example 18) | <10 | >10 | >10 |

As shown in Table 6, the compounds of the present invention showed selective affinity to the opioid δ receptor.

Example 39 hERG (Human Ether-a-go-go-Related Gene) Potassium Channel Inhibition Test

The test was performed with Qpatch16 (Sophion Biosciences Inc.) full automatic patch clamp system using hERG channel-stably expressing CHO-K1 cells. The hERG channel inhibitory action of each test compound was obtained on the basis of inhibitory action against a tail current induced by a test pulse at 40 mV for 1 second applied after retention at +20 mV for 2 seconds. The test compound was dissolved in an extracellular fluid (137 mM NaCl, 4 mM KCl, 1.8 mM CaCl$_2$, 1 mM MgCl$_2$, 10 mM D(+)-glucose, 10 mM HEPES, pH 7.4), and the solution was refluxed at room temperature for 5 minutes. The inhibition ratio was obtained from the ratio of the tail current value observed after the compound was applied based on the tail current value observed before the compound was applied, which was taken as 100%. Cells were used for the test, where the cells show a peak tail current value not smaller than 100 pA, tail current run-down smaller than 30% of the initial current value, leak current smaller than 50% of the peak value of the tail current, and series resistance value lower than 20 MΩ.

TABLE 7

| Compound | Concentration | HERG channel inhibitory action |
|---|---|---|
| Compound 13 Dihydrochloride (Example 2) | 10 μM | <50% |

TABLE 7-continued

| Compound | Concentration | HERG channel inhibitory action |
|---|---|---|
| Compound 19 Dimesylate (Example 3) | 10 μM | <50% |
| Compound 31 Dimesylate (Example 7) | 10 μM | <50% |
| Compound 64 Dihydrochloride (Example 32) | 10 μM | <50% |
| Compound 76 Trihydrochloride (Example 36) | 10 μM | <50% |

As shown in Table 7, the inhibitory actions of the compounds of the present invention against the hERG potassium channel, which promotes the repolarization of myocardium, were weak.

What is claimed is:

1. A morphinan compound represented by the following formula (I), a tautomer or stereoisomer of the compound, or a pharmaceutically acceptable salt or solvate thereof:

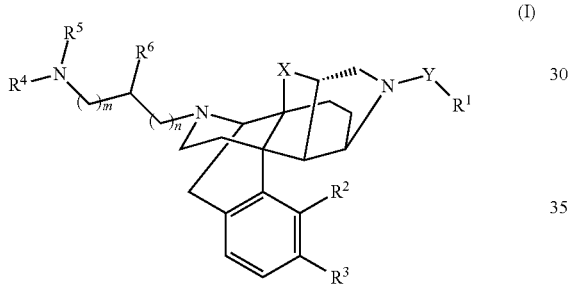

(I)

wherein, $R^1$ represents hydrogen, $C_{1-6}$ alkyl, $C_{3-6}$ cycloalkyl, $C_{6-10}$ aryl, heteroaryl containing 1 to 4 heteroatoms selected from N, O, and S as a ring-constituting atom, aralkyl in which the aryl moiety has 6 to 10 carbon atoms and the alkylene moiety has 1 to 5 carbon atoms, heteroarylalkyl in which the heteroaryl contains 1 to 4 heteroatoms selected from N, O, and S as a ring-constituting atom and the alkylene moiety has 1 to 5 carbon atoms, cycloalkylalkyl in which the cycloalkyl moiety has 3 to 6 carbon atoms and the alkylene moiety has 1 to 5 carbon atoms, $C_{2-6}$ alkenyl, arylalkenyl in which the aryl moiety has 6 to 10 carbon atoms and the alkenyl moiety has 2 to 6 carbon atoms, heteroarylalkenyl in which the heteroaryl contains 1 to 4 heteroatoms selected from N, O, and S as a ring-constituting atom and the alkenyl moiety has 2 to 6 carbon atoms, cycloalkylalkenyl in which the cycloalkyl moiety has 3 to 6 carbon atoms and the alkenyl moiety has 2 to 6 carbon atoms, $C_{4-6}$ cycloalkenyl, cycloalkenylalkyl in which the cycloalkenyl moiety has 4 to 6 carbon atoms and the alkylene moiety has 1 to 5 carbon atoms, or cycloalkenylalkenyl in which the cycloalkenyl moiety has 4 to 6 carbon atoms and the alkenyl moiety has 2 to 6 carbon atoms, $R^2$ and $R^3$, which are the same or different, represent hydrogen, hydroxy, cyano, carbamoyl, $C_{1-6}$ alkoxy, $C_{6-10}$ aryloxy, or $C_{1-6}$ alkanoyloxy, $R^4$ and $R^5$, which are the same or different, represent hydrogen, $C_{1-6}$ alkyl, $C_{3-6}$ cycloalkyl, $C_{6-10}$ aryl, cycloalkylalkyl in which the cycloalkyl moiety has 3 to 6 carbon atoms and the alkylene moiety has 1 to 5 carbon atoms, aralkyl in which the aryl moiety has 6 to 10 carbon atoms and the alkylene moiety has 1 to 5 carbon atoms, or heteroarylalkyl in which the heteroaryl contains 1 to 4 heteroatoms selected from N, O, and S as a ring-constituting atom and the alkylene moiety has 1 to 5 carbon atoms, or $R^5$ and $R^4$ may combine together to form a 4- to 7-membered ring, which may contain a heteroatom selected from N, O, and S as a ring-constituting atom other than the N atom to which $R^5$ binds, provided the ring is not a heteroaryl, together with the nitrogen atom to which $R^5$ binds, $R^6$ represents hydrogen, hydroxy, $C_{1-6}$ alkyl, $C_{3-6}$ cycloalkyl, $C_{6-10}$ aryl, cycloalkylalkyl in which the cycloalkyl moiety has 3 to 6 carbon atoms and the alkylene moiety has 1 to 5 carbon atoms, aralkyl in which the aryl moiety has 6 to 10 carbon atoms and the alkylene moiety has 1 to 5 carbon atoms, or heteroarylalkyl in which the heteroaryl contains 1 to 4 heteroatoms selected from N, O, and S as a ring-constituting atom and the alkylene moiety has 1 to 5 carbon atoms, or $R^6$ and $R^5$ may combine together to form a 4- to 7-membered ring, which may contain a heteroatom selected from N, O, and S as a ring-constituting atom other than the N atom to which $R^5$ binds, provided the ring is not a heteroaryl, together with the N atom to which $R^5$ binds, X represents O or $CH_2$, Y represents C=O, C(=O)O, C(=O)$NR^7$, $SO_2$, or a bond, wherein $R^7$ represents hydrogen, $C_{1-6}$ alkyl, aralkyl in which the aryl moiety has 6 to 10 carbon atoms and the alkylene moiety has 1 to 5 carbon atoms, heteroarylalkyl in which the heteroaryl contains 1 to 4 heteroatoms selected from N, O, and S as a ring-constituting atom and the alkylene moiety has 1 to 5 carbon atoms, or cycloalkylalkyl in which the cycloalkyl moiety has 3 to 6 carbon atoms and the alkylene moiety has 1 to 5 carbon atoms, or the N atom to which $R^7$ binds and $R^1$ may combine together to form a 4- to 7-membered ring which may contain a heteroatom selected from N, O, and S as a ring-constituting atom other than the N atom to which $R^7$ binds, and m and n, which are the same or different, represent an integer of 0 to 2, provided that m and n are not 0 at the same time, wherein the $C_{1-6}$ alkyl of $R^1$, $R^4$, $R^5$, and $R^6$, the 4- to 7-membered ring formed by $R^5$ and $R^6$, and the 4- to 7-membered ring formed by $R^5$ and $R^4$ may be substituted with a hydroxy group, and the aryl moiety of the $C_{6-10}$ aryl and the aralkyl in which the aryl moiety has 6 to 10 carbon atoms and the alkylene moiety has 1 to 5 carbon atoms of $R^1$, and the heteroaryl moiety of the heteroaryl containing 1 to 4 heteroatoms selected from N, O, and S as a ring-constituting atom, and the heteroarylalkyl in which the heteroaryl contains 1 to 4 heteroatoms selected from N, O, and S as a ring-constituting atom and the alkylene moiety has 1 to 5 carbon atoms of $R^1$, may be substituted with at least one substituent selected from $C_{1-6}$ alkyl, $C_{1-6}$ alkoxy, $C_{1-6}$ alkanoyloxy, hydroxy, alkoxycarbonyl in which the alkoxy moiety has 1 to 6 carbon atoms, carbamoyl, alkylcarbamoyl in which the alkyl moiety has 1 to 6 carbon atoms, dialkylcarbamoyl in which each alkyl moiety has 1 to 6 carbon atoms, halogen, nitro, cyano, $C_{1-6}$ alkyl substituted with 1 to 3 halogens, $C_{1-6}$ alkoxy substituted with 1 to 3 halogens, phenyl, heteroaryl containing 1 to 4 heteroatoms selected from N, O, and S as a ring-constituting atom, phenoxy, phenylalkyl in which the alkyl moiety has 1 to 3 carbon atoms, methylenedioxy, and $NR^8R^9$, wherein $R^8$ and $R^9$ independently represent hydrogen, $C_{1-6}$ alkyl, $C_{2-6}$ alkenyl, $C_{3-6}$ cycloalkyl, $C_{1-6}$ alkanoyl, or alkoxycarbonyl in which the alkoxy moiety has 1 to 6 carbon atoms, or $R^8$ and $R^9$ may form, together with the N atom to which they bind, a 4- to 7-membered ring which may further contain a heteroatom selected from N, O, and S.

2. The morphinan compound, a tautomer or stereoisomer of the compound, or a pharmaceutically acceptable salt thereof, or a solvate thereof according to claim 1, wherein:

$R^1$ represents hydrogen, $C_{1-6}$ alkyl, $C_{3-6}$ cycloalkyl, $C_{6-10}$ aryl, heteroaryl containing 1 to 4 heteroatoms selected from N, O, and S as a ring-constituting atom, aralkyl in which the aryl moiety has 6 to 10 carbon atoms and the alkylene moiety has 1 to 5 carbon atoms, heteroarylalkyl in which the heteroaryl contains 1 to 4 heteroatoms selected from N, O, and S as a ring-constituting atom and the alkylene moiety has 1 to 5 carbon atoms, cycloalkylalkyl in which the cycloalkyl moiety has 3 to 6 carbon atoms and the alkylene moiety has 1 to 5 carbon atoms, $C_{2-6}$ alkenyl, arylalkenyl in which the aryl moiety has 6 to 10 carbon atoms and the alkenyl moiety has 2 to 6 carbon atoms, heteroarylalkenyl in which the heteroaryl contains 1 to 4 heteroatoms selected from N, O, and S as a ring-constituting atom and the alkenyl moiety has 2 to 6 carbon atoms, cycloalkylalkenyl in which the cycloalkyl moiety has 3 to 6 carbon atoms and the alkenyl moiety has 2 to 6 carbon atoms, $C_{4-6}$ cycloalkenyl, cycloalkenylalkyl in which the cycloalkenyl moiety has 4 to 6 carbon atoms and the alkylene moiety has 1 to 5 carbon atoms, or cycloalkenylalkenyl in which the cycloalkenyl moiety has 4 to 6 carbon atoms and the alkenyl moiety has 2 to 6 carbon atoms, $R^2$ and $R^3$, which are the same or different, represent hydrogen, hydroxy, cyano, carbamoyl, $C_{1-6}$ alkoxy, $C_{6-10}$ aryloxy, or $C_{1-6}$ alkanoyloxy, $R^4$, $R^5$, and $R^6$, which are the same or different, represent hydrogen, $C_{1-6}$ alkyl, $C_{3-6}$ cycloalkyl, $C_{6-10}$ aryl, cycloalkylalkyl in which the cycloalkyl moiety has 3 to 6 carbon atoms, and the alkylene moiety has 1 to 5 carbon atoms, aralkyl in which the aryl moiety has 6 to 10 carbon atoms and the alkylene moiety has 1 to 5 carbon atoms, or heteroarylalkyl in which the heteroaryl contains 1 to 4 heteroatoms selected from N, O, and S as a ring-constituting atom, and the alkylene moiety has 1 to 5 carbon atoms, or $R^5$ and $R^4$ or $R^6$ may combine together to form a 4- to 7-membered ring, which may contain a heteroatom selected from N, O, and S as a ring-constituting atom other than the N atom to which $R^5$ binds, together with the N atom to which $R^5$ binds, X represents O or $CH_2$, Y represents C=O, C(=O)O, C(=O)$NR^7$, $SO_2$, or an atomic bond, wherein $R^7$ represents hydrogen, $C_{1-6}$ alkyl, aralkyl in which the aryl moiety has 6 to 10 carbon atoms and the alkylene moiety has 1 to 5 carbon atoms, heteroarylalkyl in which the heteroaryl contains 1 to 4 heteroatoms selected from N, O, and S as a ring-constituting atom and the alkylene moiety has 1 to 5 carbon atoms, cycloalkylalkyl in which the cycloalkyl moiety has 3 to 6 carbon atoms and the alkylene moiety has 1 to 5 carbon atoms, or the N atom to which $R^7$ binds and $R^1$ may combine together to form a 4- to 7-membered ring, which may contain a heteroatom selected from N, O, and S as a ring-constituting atom other than the N atom to which $R^7$ binds, and m and n, which are the same or different, represent an integer of 0 to 2, provided that m and n are not 0 at the same time, wherein the $C_{1-6}$ alkyl of $R^1$, $R^4$, $R^5$, and $R^6$, the 4- to 7-membered ring formed by $R^5$ and $R^6$, and the 4- to 7-membered ring formed by $R^5$ and $R^4$ may be substituted with a hydroxy group, and the aryl moiety of the $C_{6-10}$ aryl and the aralkyl in which the aryl moiety has 6 to 10 carbon atoms and the alkylene moiety has 1 to 5 carbon atoms of $R^1$, and the heteroaryl moiety of the heteroaryl containing 1 to 4 heteroatoms selected from N, O, and S as a ring-constituting atom and the heteroarylalkyl in which the heteroaryl contains 1 to 4 heteroatoms selected from N, O, and S as a ring-constituting atom and the alkylene moiety has 1 to 5 carbon atoms of $R^1$ may be substituted with at least one substituent selected from $C_{1-6}$ alkyl, $C_{1-6}$ alkoxy, $C_{1-6}$ alkanoyloxy, hydroxy, alkoxycarbonyl in which the alkoxy moiety has 1 to 6 carbon atoms, carbamoyl, alkylcarbamoyl in which the alkyl moiety has 1 to 6 carbon atoms, dialkylcarbamoyl in which each alkyl moiety has 1 to 6 carbon atoms, halogen, nitro, cyano, $C_{1-6}$ alkyl substituted with 1 to 3 halogens, $C_{1-6}$ alkoxy substituted with 1 to 3 halogens, phenyl, heteroaryl containing 1 to 4 heteroatoms selected from N, O, and S as a ring-constituting atom, phenoxy, phenylalkyl in which the alkyl moiety has 1 to 3 carbon atoms, methylenedioxy, and $NR^8R^9$, wherein $R^8$ and $R^9$ independently represent hydrogen, $C_{1-6}$ alkyl, $C_{2-6}$ alkenyl, $C_{3-6}$ cycloalkyl, $C_{1-6}$ alkanoyl, or alkoxycarbonyl in which the alkoxy moiety has 1 to 6 carbon atoms, or $R^8$ and $R^9$ may form, together with the N atom to which they bind, a 4- to 7-membered ring which may further contain a heteroatom selected from N, O, and S.

3. The morphinan compound, a tautomer or stereoisomer of the compound, or a pharmaceutically acceptable salt thereof, or a solvate thereof according to claim 1, wherein X is $CH_2$.

4. The morphinan compound, a tautomer or stereoisomer of the compound, or a pharmaceutically acceptable salt thereof, or a solvate thereof according to claim 1, wherein $R^4$, $R^5$, and $R^6$, which are the same or different, are hydrogen, $C_{1-6}$ alkyl, or cycloalkylalkyl in which the cycloalkyl moiety has 3 to 6 carbon atoms and the alkylene moiety has 1 to 5 carbon atoms.

5. The morphinan compound, a tautomer or stereoisomer of the compound, or a pharmaceutically acceptable salt thereof, or a solvate thereof according to claim 1, wherein $R^5$ and $R^4$ or $R^6$ combine together to form a 4- to 7-membered ring, which may contain a heteroatom selected from N, O, and S as a ring-constituting atom other than the N atom to which $R^5$ binds, together with the N atom to which $R^5$ binds.

6. The morphinan compound, a tautomer or stereoisomer of the compound, or a pharmaceutically acceptable salt thereof, or a solvate thereof according to claim 1, wherein $R^5$ and $R^6$ combine together to form a 4- to 7-membered ring, which may contain a heteroatom selected from N, O, and S as a ring-constituting atom other than the N atom to which R⁵ binds, together with the N atom to which R⁵ binds.

7. The morphinan compound, a tautomer or stereoisomer of the compound, or a pharmaceutically acceptable salt thereof, or a solvate thereof according to claim 1, wherein the sum of m and n is an integer of 1 to 3.

8. The morphinan compound, a tautomer or stereoisomer of the compound, or a pharmaceutically acceptable salt thereof, or a solvate thereof according to claim 1, wherein n is 1.

9. The morphinan compound, a tautomer or stereoisomer of the compound, or a pharmaceutically acceptable salt thereof, or a solvate thereof according to claim 1, wherein R⁶ is a hydroxy group.

10. The morphinan compound, a tautomer or stereoisomer of the compound, or a pharmaceutically acceptable salt thereof, or a solvate thereof according to claim 1, wherein R⁶ is $C_{1-6}$ alkyl substituted with hydroxy group.

11. The morphinan compound, a tautomer or stereoisomer of the compound, or a pharmaceutically acceptable salt thereof, or a solvate thereof according to claim 1, wherein Y is C=O, C(=O)NR⁷, or an atomic bond.

12. The morphinan compound, a tautomer or stereoisomer of the compound, or a pharmaceutically acceptable salt thereof, or a solvate thereof according to claim 1, wherein R¹ is aryl or heteroaryl which may have a substituent.

13. The morphinan compound, a tautomer or stereoisomer of the compound, or a pharmaceutically acceptable salt thereof, or a solvate thereof according to claim 1, wherein R² is hydrogen, and R³ is hydrogen, hydroxy, carbamoyl, $C_{1-6}$ alkoxy, or $C_{1-6}$ alkanoyloxy.

14. The morphinan compound, a tautomer or stereoisomer of the compound, or a pharmaceutically acceptable salt thereof, or a solvate thereof according to claim 1, wherein R² is hydrogen, and R³ is hydroxy.

15. The morphinan compound, a tautomer or stereoisomer of the compound, or a pharmaceutically acceptable salt thereof, or a solvate thereof according to claim 1, wherein R⁵ and R⁴ or R⁶ combine together to form an azetidine ring, a pyrrolidine ring, a piperidine ring, a piperazine ring, or a morpholine ring.

16. A morphinan compound selected from the following group, or a tautomer or stereoisomer of the compound, or a pharmaceutically acceptable salt or solvate thereof:
  [(1S,3aR,5aS,6R,11bR,11cS)-14-(2-aminoethyl)-10-methoxy-1,2,3a,4,5,6,7,11c-octahydro-3H-6,11b-(epiminoethano)-1,5a-methanonaphtho[1,2-e]indol-3-yl](phenyl)methanone,
  [(1S,3aR,5aS,6R,11bR,11cS)-14-(2-aminoethyl)-10-hydroxy-1,2,3a,4,5,6,7,11c-octahydro-3H-6,11b-(epiminoethano)-1,5a-methanonaphtho[1,2-e]indol-3-yl](phenyl)methanone,
  [(1S,3aR,5aS,6R,11bR,11cS)-10-hydroxy-14-[[(2S)-pyrrolidin-2-yl]methyl]-1,2,3a,4,5,6,7,11c-octahydro-3H-6,11b-(epiminoethano)-1,5a-methanonaphtho[1,2-e]indol-3-yl](phenyl)methanone, [(1S,3aR,5aS,6R,11bR,11cS)-10-hydroxy-14-[[(2S)-1-methylpyrrolidin-2-yl]methyl]-1,2,3a,4,5,6,7,11c-octahydro-3H-6,11b-(epiminoethano)-1,5a-methanonaphtho[1,2-e]indol-3-yl](phenyl)methanone,
  [(1S,3aR,5aS,6R,11bR,11cS)-14-(azetidin-2-ylmethyl)-10-hydroxy-1,2,3a,4,5,6,7,11c-octahydro-3H-6,11b-(epiminoethano)-1,5a-methanonaphtho[1,2-e]indol-3-yl](phenyl)methanone,
  [(1S,3aR,5aS,6R,11bR,11cS)-10-hydroxy-14-[3-(phenylamino)propyl]-1,2,3a,4,5,6,7,11c-octahydro-3H-6,11b-(epiminoethano)-1,5a-methanonaphtho[1,2-e]indol-3-yl](phenyl)methanone, (1S,3aR,5aS,6R,11bR,11cS)-14-(2-aminoethyl)-10-hydroxy-N-isopropyl-1,2,3a,4,5,6,7,11c-octahydro-3H-6,11b-(epiminoethano)-1,5a-methanonaphtho[1,2-e]indole-3-carboxamide,
  (1S,3aR,5aS,6R,11bR,11cS)-14-(2-aminoethyl)-3-(4,6-dimethylpyrimidin-2-yl)-2,3,3a,4,5,6,7,11c-octahydro-1H-6,11b-(epiminoethano)-1,5a-methanonaphtho[1,2-e]indol-10-ol,
  [(1S,3aR,5aS,6R,11bR,11cS)-14-(3-aminopropyl)-1,2,3a,4,5,6,7,11c-octahydro-3H-6,11b-(epiminoethano)-1,5a-methanonaphtho[1,2-e]indol-3-yl](phenyl)methanone,
  [(1S,3aR,5aS,6R,11bR,11cS)-10-hydroxy-14-[3-(methylamino)propyl]-1,2,3a,4,5,6,7,11c-octahydro-3H-6,11b-(epiminoethano)-1,5a-methanonaphtho[1,2-e]indol-3-yl](phenyl)methanone,
  [(1S,3aR,5aS,6R,11bR,11cS)-14-[3-(dimethylamino)propyl]-10-hydroxy-1,2,3a,4,5,6,7,11c-octahydro-3H-6,11b-(epiminoethano)-1,5a-methanonaphtho[1,2-e]indol-3-yl](phenyl)methanone,
  [(1S,3aR,5aS,6R,11bR,11cS)-14-(3-amino-2-hydroxypropyl)-10-hydroxy-1,2,3a,4,5,6,7,11c-octahydro-3H-6,11b-(epiminoethano)-1,5a-methanonaphtho[1,2-e]indol-3-yl](phenyl)methanone,
  [(1S,3aR,5aS,6R,11bR,11cS)-14-[(2R)-2-amino-3-hydroxypropyl]-10-hydroxy-1,2,3a,4,5,6,7,11c-octahydro-3H-6,11b-(epiminoethano)-1,5a-methanonaphtho[1,2-e]indol-3-yl](phenyl)methanone,
  [(1S,3aR,5aS,6R,11bR,11cS)-14-[(2S)-2-amino-3-hydroxypropyl]-10-hydroxy-1,2,3a,4,5,6,7,11c-octahydro-3H-6,11b-(epiminoethano)-1,5a-methanonaphtho[1,2-e]indol-3-yl](phenyl)methanone,
  (1S,3aR,5aS,6R,11bR,11cS)-3-(4,6-dimethylpyrimidin-2-yl)-14-[2-(methylamino)ethyl]-2,3,3a,4,5,6,7,11c-octahydro-1H-6,11b-(epiminoethano)-1,5a-methanonaphtho[1,2-e]indol-10-ol,
  (1S,3aR,5aS,6R,11bR,11cS)-14-[2-(dimethylamino)ethyl]-3-(4,6-dimethylpyrimidin-2-yl)-2,3,3a,4,5,6,7,11c-octahydro-1H-6,11b-(epiminoethano)-1,5a-methanonaphtho[1,2-e]indol-10-ol, and
  (1S,3aR,5aS,6R,11bR,11cS)-14-(3-aminopropyl)-3-(4,6-dimethylpyrimidin-2-yl)-2,3,3a,4,5,6,7,11c-octahydro-1H-6,11b-(epiminoethano)-1,5a-methanonaphtho[1,2-e]indol-10-ol.

17. A morphinan compound selected from the following group, or a tautomer or stereoisomer of the compound, or a pharmaceutically acceptable salt or solvate thereof:

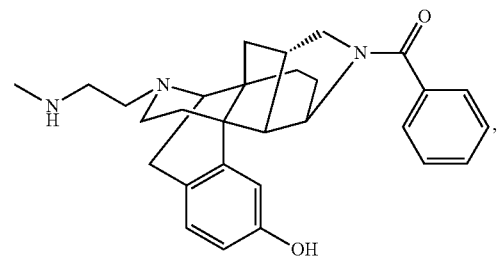

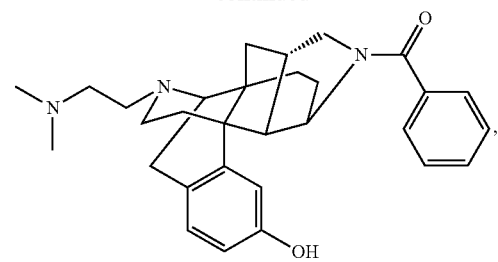
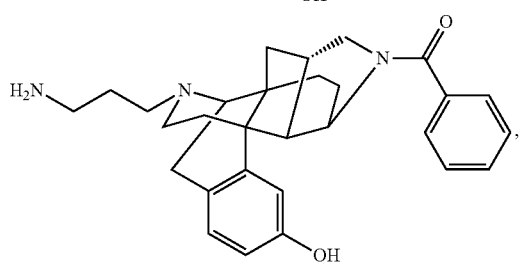
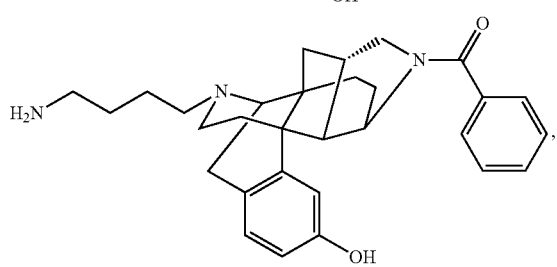
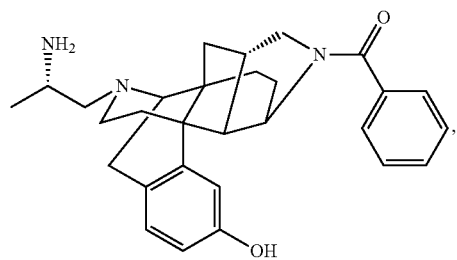
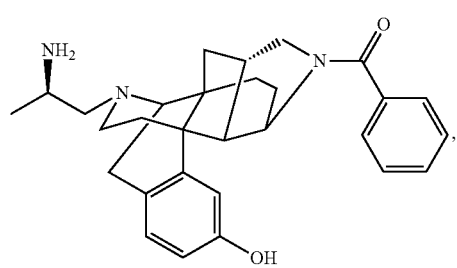
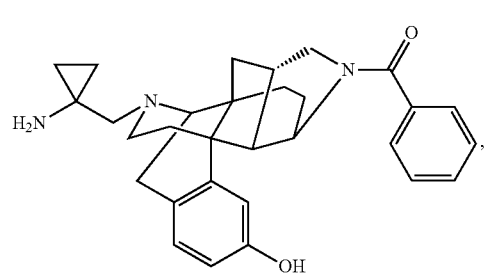
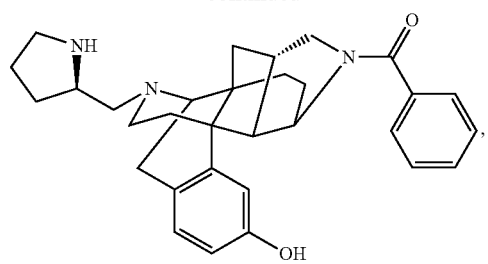
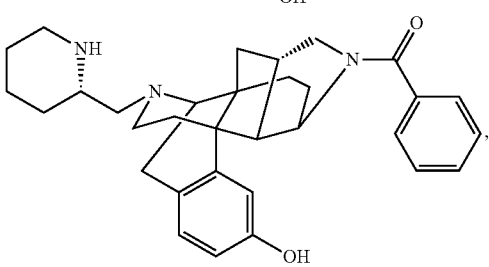
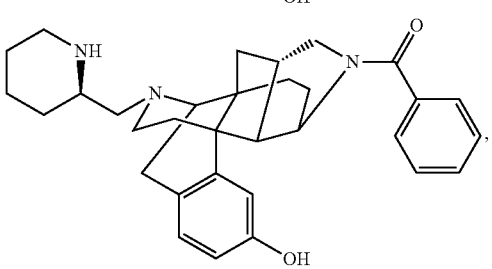
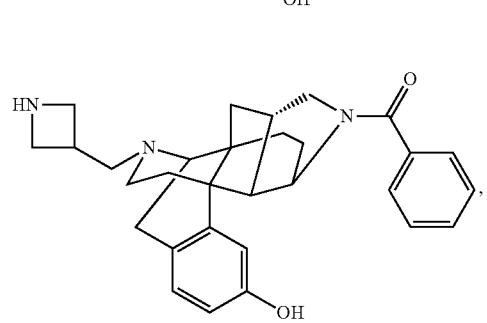
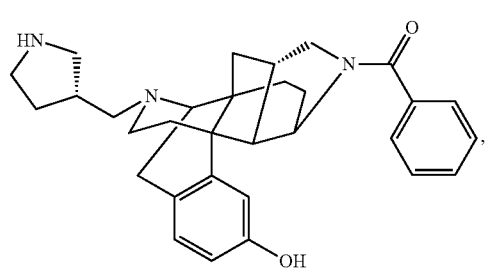
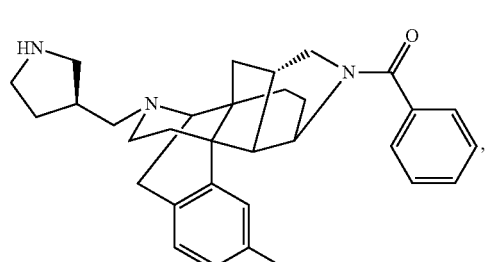

-continued

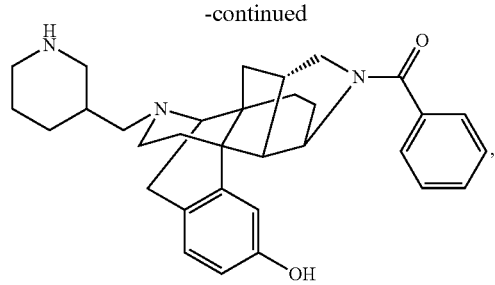

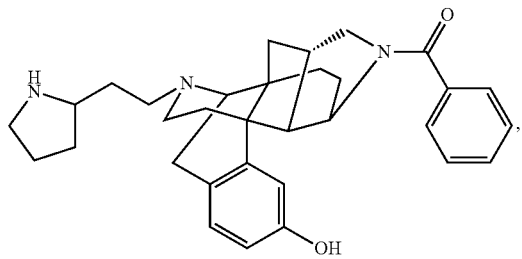

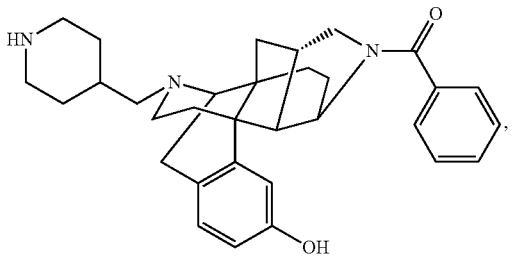

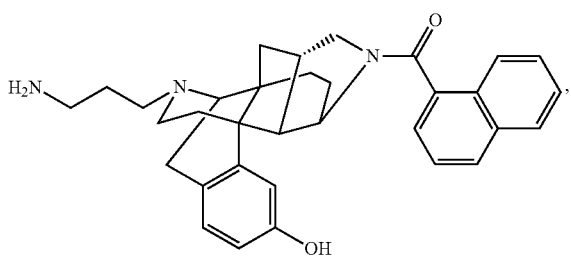

-continued

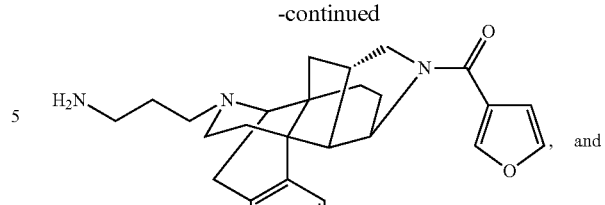

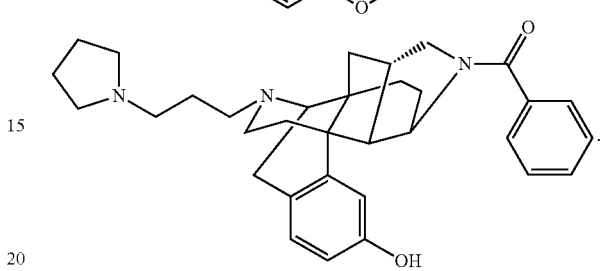

18. The morphinan compound, a tautomer or stereoisomer of the compound, or a pharmaceutically acceptable salt or solvate thereof according to any one of claim 1, 16, or 17, wherein the salt is an acid addition salt.

19. A pharmaceutical composition comprising the morphinan compound, a tautomer or stereoisomer of the compound, or a pharmaceutically acceptable salt or solvate thereof according to any one of claim 1, 16, or 17, and at least one pharmaceutical excipient.

20. A method of treating pain comprising administering the morphinan compound, a tautomer or stereoisomer of the compound, or a pharmaceutically acceptable salt or solvate thereof according to any one of claim 1, 16, or 17, to a patient in need of such treatment.

21. A method of treating anxiety comprising administering the morphinan compound, a tautomer or stereoisomer of the compound, or a pharmaceutically acceptable salt or solvate thereof according to any one of claim 1, 16, or 17, to a patient in need of such treatment.

22. A method of treating depression comprising administering the morphinan compound, a tautomer or stereoisomer of the compound, or a pharmaceutically acceptable salt or solvate thereof according to any one of claim 1, 16, or 17, to a patient in need of such treatment.

* * * * *